(12) United States Patent
Yamada et al.

(10) Patent No.: US 7,572,576 B2
(45) Date of Patent: Aug. 11, 2009

(54) METHOD OF PREDICTING GENETIC RISK FOR HYPERTENSION

(75) Inventors: Yoshiji Yamada, Nagoya (JP); Mitsuhiro Yokota, Nagoya (JP)

(73) Assignee: Nagoya Industrial Science Research Institute, Nagoya-shi (JP)

( * ) Notice: Subject to any disclaimer, the term of this patent is extended or adjusted under 35 U.S.C. 154(b) by 241 days.

(21) Appl. No.: 10/528,659

(22) PCT Filed: Sep. 22, 2003

(86) PCT No.: PCT/JP03/12052

§ 371 (c)(1),
(2), (4) Date: Oct. 5, 2005

(87) PCT Pub. No.: WO2004/029243

PCT Pub. Date: Apr. 8, 2004

(65) Prior Publication Data

US 2006/0099594 A1    May 11, 2006

(30) Foreign Application Priority Data

Sep. 25, 2002  (JP) .............................. 2002-280034

(51) Int. Cl.
*C12Q 1/68* (2006.01)
*C07H 21/04* (2006.01)
(52) U.S. Cl. ......................................... 435/6; 536/23.5
(58) Field of Classification Search ........................ None
See application file for complete search history.

(56) References Cited

U.S. PATENT DOCUMENTS

| 5,474,796 A | * | 12/1995 | Brennan | ..................... 472/2.13 |
| 5,827,730 A | | 10/1998 | Pedersen et al. | |
| 2002/0086297 A1 | | 7/2002 | Siffert | |
| 2006/0099590 A1 | | 5/2006 | Yamada et al. | |

FOREIGN PATENT DOCUMENTS

| EP | 0 955 382 A2 | 11/1999 |
| EP | 0 955 382 A3 | 11/1999 |
| JP | 2004-065203 | 3/2004 |
| WO | 94/29345 A1 | 12/1994 |
| WO | 97/43442 A1 | 11/1997 |
| WO | 00/15785 A2 | 3/2000 |

(Continued)

OTHER PUBLICATIONS

Izawa, H. et al. Hypertension 41:1035-1040 (Mar. 2003).*

(Continued)

*Primary Examiner*—Diana B Johannsen
(74) *Attorney, Agent, or Firm*—Edwards Angell Palmer & Dodge LLP

(57) ABSTRACT

It is intended to provide a means of predicting genetic risk for hypertension at a high accuracy and high prediction possibility. Namely, risk for hypertension is predicted by a method involving the following steps: (i) the step of analyzing two or more polymorphisms selected from among 4 gene polymorphisms having been revealed as relating to hypertension; (ii) the step of determining the genotype of a nucleic acid sample based on the polymorphism data obtained in the above step; and (iii) the step of predicting the genetic risk for hypertension from the genotype thus determined.

1 Claim, 11 Drawing Sheets

| Glycoprotein Ia (0 = AA = AG, 1 = GG) | Chemokine receptor 2 (0 = GG = GA, 1 = AA) | Apolipoprotein C-III (0 = CC = CT, 1 = TT) | G protein β3 subunit (0 = CC, 1 = CT = TT) | Odds ratio |
|---|---|---|---|---|
| 0 | 1 | 0 | 1 | 5.34 |
| 0 | 1 | 0 | 0 | 4.05 |
| 0 | 1 | 1 | 1 | 3.90 |
| 0 | 1 | 1 | 0 | 2.95 |
| 0 | 0 | 0 | 1 | 3.24 |
| 0 | 0 | 0 | 0 | 2.45 |
| 0 | 0 | 1 | 1 | 2.36 |
| 0 | 0 | 1 | 0 | 1.79 |
| 1 | 1 | 0 | 1 | 2.98 |
| 1 | 1 | 0 | 0 | 2.26 |
| 1 | 1 | 1 | 1 | 2.18 |
| 1 | 1 | 1 | 0 | 1.65 |
| 1 | 0 | 0 | 1 | 1.81 |
| 1 | 0 | 0 | 0 | 1.37 |
| 1 | 0 | 1 | 1 | 1.32 |
| 1 | 0 | 1 | 0 | 1.00 |

FOREIGN PATENT DOCUMENTS

WO 01/62796 A1 8/2001
WO 01/75065 A2 10/2001

OTHER PUBLICATIONS

Mettimano, M. et al. British Journal of Biomedical Science 60(1):19-21 (Apr. 2003).*
Gonzalez, P. et al. Genes and Immunity 2:191-195 (Jun. 2001).*
Groenendijk, M. et al. Journal of Lipid Research 42:188-194 (Feb. 2001).*
Peacock, R.E. et al. Genetic Epidemiology 14:265-282 (1997).*
Y. Yamada, et al.; "Prediction of the Risk of Myocardial Infarction from Polymorphisms in Candidate Genes;" *The New England Journal of Medicine*; vol. 347; No. 24; Dec. 12, 2002; pp. 1916-1923 and Supplementary Appendix (5 Sheets.)/Discussed in the specification.
Lifton R.P. et al. Molecular mechanisms of human hypertension. Cell. 2001; 104:545-556.
Xu X., et al. An extreme-sib-pair genome scan for genes regulating blood pressure. Am J Hum Genet. 1999;64:1694-1701.
Krushkal J. et al. Genome-wide linkage analysis of systolic blood pressure using highly discordant sibblings. Circulation. 1999;99:1407-1410.
Rice T. et al. Genome-wide linkage analysis of systolic and diastolic blood pressure: the Quebec Family Study. Circulation. 2000;102:1956-1963.
Jeunemaitre X. et al. Molecular basis of human hypertension: Role of Angiotensinogen. Cell. 1992;71:169-180.
Cusi D. et al. Polymorphisms of α-adducin and salt sensitivity in patients with essential hypertension. Lancet. 1997;349:1353-1357.
Siffert W. et al. Association of a human G-protein β3 subunit variant with hypertension. Nat Genet. 1998;18:45-48.
Bray M.S. et al. Positional genomic analysis identifies the $\beta_2$-Adrenergic receptor gene as a susceptibility locus for hypertension. Circulation. 2000; 101:2877-2882.
Pausova Z. et al. Role of tumor necrosis factor-α gene locus in obesity and obesity-associated hypertension in French Canadians. Hypertension. 2000;36: 14-19.
Frossard P.M. et al, A study of five human cytokine genes in human essential hypertension. Mol. Immunol. 2002; 38:969-976.
Zinman B. et al. Circulating tumor necrosis factor-α concentrations in a native Canadian population with high rates of type 2 diabetes mellitus. J Clin. Endocrinol. Metab. 1999;84:272-278.
Kahaleh M.B. et al. Effect of cytokines on the production of endothelin by endothelial cells. Clin. Exp. Rheumatol. 1997;15:163-167.
Winkler G. et al. Elevated serum TNF-α level as a link between endothelial dysfunction and insulin resistance in normotensive obese patients. Diabetic Med. 1999;16:207-211.
Bush E. et al. CC chemokine receptor 2 is required for macrophage infiltration and vascular hypertrophy in angiotensin II-induced hypertension. Hypertension. 2000;36:360-363.
Abe H. et al. Hypertension, hypertriglyceridemia, and impaired endothelium-dependent vascular relaxation in mice lacking insulin receptor substrate-1. J. Clin. Invest. 1998;101:1784-1788.
Andrioli G. et al, Study of platelet adhesion in patients with uncomplicated hypertension. J. Hypertension. 1996;14:1215-1221.
Dockrell M. E. et al. Platelet aggregation in young men contrasting predisposition to high blood pressure. Am. J. Hypertension. 1999;12:115-119.
Bereczki, Cs. et al. The roles of platelet function, thromboxane, blood lipids, and nitric oxide in hypertension of children and adolescents. Prostaglandins Leukot. Essent. Fatty Acids. 2000;62:293-297.
Murata M. et al. Coronary artery disease and polymorphisms in a receptor mediating shear stress-dependent platelet activation. Circulation. 1997;96:3281-6.
Kroll, H. et al. The impact of the glycoprotein la collagen receptor subunit $A_{1648}G$ gene polymorphism on coronary artery disease and acute myocardial infarction. Thromb Haemost. 2000;83:392-396.
Nicolas von Beckerath et al. "G Protein β3 subunit polymorphism and risk of thrombosis and restenosis following coronary stent placement" Atherosclerosis, 2000, 149, 151-155.
Juliano C. Padovani et al. "Gene Polymorphisms in the TNF Locus and the Risk of Myocardial Infarction" Thrombosis Research, 2000, 100, 263-269.
Douglas H. et al. "Platelet member glycoprotein Ibα gene -5T/C Kozak sequence polymorphism as an independent risk factor for the occurrence of coronary thrombosis" Heart, 2002, 87, 70-74.
M. K. Halushka et al., "Patterns of single-nucleotide polymorphisms in candidate genes for blood-pressure homeostasis," *Nature Genetics*, vol. 22, Jul. 1999, pp. 239-247.
A. Bonnardeaux et al., "Angiotensin II Type 1 Receptor Gene Polymorphisms in Human Essential Hypertension," *Hypertension*, vol. 24, No. 1, Jul. 1994, pp. 63-69.
X. Jeunemaitre et al., "Molecular Basis of Human Hypertension: Role of Angiotensinogen," *Cell*, vol. 71, Oct. 1992, pp. 169-180.
F. Navarro-López, "Bases genéticas de la enfermedad coronaria," *Revista Espanola de Cardiologia*, vol. 55, No. 4, Apr. 2002, pp. 413-431. English abstract only.
Sinan Tas, "Blood pressure, coronary artery disease, and glycaemic control in type 2 diabetes mellitus: relation to apollpoprotein-CIII gene polymorphism," The Lancet, vol. 343, May 14, 1994, pp. 1194-1195.

* cited by examiner

Fig.1

| gene | polymorphism | gene | polymorphism |
|---|---|---|---|
| Angiotensin converting enzyme | I/D in intron 16 | Insulin receptor substrate-1 | 3494G→A (Gly972Arg) |
| Angiotensin II type I receptor | -535C→T | Interleukin-10 | -1082G→A |
| Angiotensinogen | -6G→A | | -819T→C |
| Apolipoprotein A1 | -75G→A | | -592A→C |
| | 83C→T | | -889C→T |
| Apolipoprotein B | I/D in signal peptide | Interleukin-1α | -511C→T |
| Apolipoprotein C-III | -482C→T | Interleukin-1β | 3953C→T |
| | 1100C→T | Interleukin-6 | -634C→G |
| Apolipoprotein E | -491A→T | | -174G→C |
| | -219G→T | LDL receptor related protein | 766C→T |
| | 3932T→C (Cys112Arg) | Leptin | -1887C→A |
| | 4070C→T (Arg158Cys) | Lipoprotein lipase | 280G→A (Asp9Asn) |
| Apolipoprotein (a) | 93C→T | | 1127A→G (Asn291Ser) |
| | 121G→A | | 47C→T (Ala16Val) |
| | 11764A→C (Thr12Pro) | | 173T→C (Ile58Thr) |
| ATP-binding cassette transporter 1 | -477C→T | Manganese superoxide dismutase | -7G→A |
| | 1051G→A (Arg219Lys) | Matrix Gla protein | 7158A→G (Thr83Ala) |
| Atrial natriuretic peptide | 664G→A (Val7Met) | Metalloproteinase-1 (collagenase) | -1607G→GG |
| Atrial natriuretic peptide clearance receptor | -55A→C | Metalloproteinase-12 (macrophage elastase) | -82A→G |
| β2-adrenergic receptor | 46A→G (Arg16Gly) | Methionine synthase | 2756A→G (Asp919Gly) |
| | 79C→G (Gln27Glu) | Methylenetetrahydrofolate reductase | 677C→T (Ala222Val) |
| | 491C→T (Thr164Ile) | Monocyte chemoattractant protein-1 | -2518G→A |
| β3-adrenergic receptor | 190T→C (Trp64Arg) | NADH/NADPH oxidase p22 phox | 242C→T (His72Tyr) |
| β-Fibrinogen | -854G→A | Neuropeptide Y | 1128T→C (Leu7Pro) |
| | -455G→A | Paraoxonase | -107T→C |
| | 148C→T | | 172A→T (Met55Leu) |
| | 8059G→A (Arg448Lys) | | 584G→A (Gln192Arg) |
| CD14 receptor | -260C→T | PECAM1 (CD31) | 1454C→G (Leu125Val) |

Fig.2

| Gene | Mutation |
|---|---|
| Chemokine receptor 2 | 190G→A (Val64Ile) |
| Cholesterol ester transfer protein | 1061A→G (Ile405Val) |
| | 1163A→G (Asp442Gly) |
| | 1200G→A (Arg451Gln) |
| Coagulation factor V | 1691G→A (Arg506Gln) |
| Coagulation factor VII | 11496G→A (Arg353Glu) |
| Coagulation factor XII | 46C→T |
| Coagulation factor XIII A-subunit | 163G→T (Val34Leu) |
| Connexin 37 | 1019C→T (Pro319Ser) |
| Endothelial nitric oxide synthase | -786T→C |
| | 894G→T (Glu298Asp) |
| Endothelin-1 | 5665G→T (Lys198Asn) |
| E-selectin | 98G→T |
| | 561A→C (Ser128Arg) |
| | 1839C→T (Leu554Phe) |
| Extracellular superoxide dismutase | 5775C→G (Arg213Gly) |
| Fatty acid-binding protein 2 | 2445G→A (Ala54Thr) |
| Fractalkine receptor | 84635G→A (Val249Ile) |
| Glycoprotein Ia | 807C→T |
| | 873G→A |
| Glycoprotein Ibα | 1648A→G (Lys505Glu) |
| Glycoprotein IIIa | 1018C→T (Thr145Met) |
| Glycoprotein PC-1 | 1565T→C (Leu33Pro) |
| G-protein β3 subunit | 97A→C (Lys121Gln) |
| Hemochromatosis-associated protein | 825C→T (splice variant) |
| | 845G→A (Cys282Tyr) |
| Hepatic lipase | -480C→T |
| | -250G→A |
| PECAM1 (CD31) | 4428G→A (Ser563Asn) |
| Peroxisome proliferator-activated receptor-α | 696C→G (Leu162Val) |
| Peroxisome proliferator-activated receptor-γ2 | 34C→G (Pro12Ala) |
| | 344C→A (Pro115Gln) |
| Plasminogen-activator inhibitor-1 | -668/4G→5G |
| Platelet-activating factor acetylhydrolase | 994G→T (Val279Phe) |
| Prothrombin | 20210G→A |
| P-selectin | 76666A→C (Thr715Pro) |
| Scavenger receptor-BI | 4G→A (Gly2Ser) |
| | 403G→A (Val135Ile) |
| Serotonin 2A receptor | 102T→C |
| Stromelysin-1 | -1171/5A→6A |
| Thrombomodulin | -33G→A |
| | -10GG→TA |
| | 845G→A (Ala25Thr) |
| | 2136C→T (Ala455Val) |
| Thrombopoietin | 5713A→G |
| Thrombospondin 1 | 2210A→G (Asn700Ser) |
| Thrombospondin 4 | 1186G→C (Ala387Pro) |
| Tissue factor pathway inhibitor | 874G→A (Val264Met) |
| Transforming growth factor-β1 | -509C→T |
| | 869T→C (Leu10Pro) |
| Tumor necrosis factor-α | -863C→A |
| | -850C→T |
| | -308G→A |
| | -238G→A |
| von Willebrand factor | -1234C→T |
| | -1051G→A |

Fig.3

| Gene | SNP | Labels | Primers (5'→3') | Cycles | Probes (5'→3') | Formamide (%) |
|---|---|---|---|---|---|---|
| G protein β3 subunit | 825C→T | TxR | TCTGCGGCATCACGTXCG | 35 | | |
| | | FITC | TCTGCGGCATCACGTXTG | | | |
| | | Biotin | GAATAGTAGGCGGCCACTGA | | | |
| Apolipoprotein C-III | 1100C→T | Biotin | CCTTCTCAGCTTCATGCAGG | 35 | CAGCTTCATGCAGGGCTACA | 35 |
| | | FITC | GTCTTGGTGGCTGCTTCA | | CAGCTTCATGCAGGGTTACA | |
| Chemokine receptor 2 | 190G→A | TxR | GCAGTTTATTAAGAATGAGGXCG | 40 | | |
| | | Biotin | TTGCAGTTTATTAAGATGAGGXTG | | | |
| Glycoprotein Ia | 1648A→G | FITC | GGTGCTCCCTGTCATAAATTTGA | 40 | | |
| | | TxR | GAGTCTACCTGTTTACTATCAAXAA | | | |
| | | Biotin | GAGTCTACCTGTTTACTATCAAXGA | | | |
| Tumor necrosis factor-α | -850C→T | FITC | ACCAGTACTAAAGCAAATTAAACT | 35 | ACATGGCCCTGTCTTXGTAAG | 30 |
| | | TxR | TCTACATGGCCCTGTCTTXGT | | ACATGGCCCTGTCTTXATTAAG | |
| | | Biotin | CTCTACATGGCCCTGTCTTXAT | | | |
| Tumor necrosis factor-α | -238G→A | FITC | CTCTACATGGCCCTGTCTCTTTAT | 40 | | |
| | | TxR | CCCCATCCTCCCTGCTXCG | | | |
| | | Biotin | CCCCATCCTCCCTGCTXTG | | | |
| Insulin receptor substrate-1 | 3494G→A | FITC | AGTCAGTGGCCAGAAGACC | 40 | CACCTCCXGGGGCTGCTAG | 35 |
| | | TxR | GGGCCCTGCACCTCCXGG | | CACCTCCXAGGGCTGCTAG | |
| | | Biotin | GGGCCCTGCACCTCCXAG | | | |
| Glycoprotein Ibα | 1018C→T | FITC | GGGTAGGGCCTGCAAATGCTA | 40 | | |
| | | TxR | CCCAGGGCTCCTGXCG | | | |
| | | Biotin | CCCCAGGGCTCCTGXTG | | | |
| | | | TGAGCTTCTCCAGCTTGGGTG | | | |

Fig.4

| Gene | SNP | Gene | SNP |
|---|---|---|---|
| *Men* | | *Women* | |
| Angiotensinogen | −6G→A | Apolipoprotein C-III | −482C→T |
| Apolipoprotein C-III | −482C→T | Apolipoprotein E | 3932T→C |
| Apolipoprotein C-III | 1100C→T | Apolipoprotein E | 4070C→T |
| Apolipoprotein E | −219G→T | ATP-binding cassette transporter 1 | 1051G→A |
| Apolipoprotein E | 4070C→T | CD14 receptor | −260C→T |
| Chemokine receptor 2 | 190G→A | Connexin 37 | 1019C→T |
| Connexin 37 | 1019C→T | E-selectin | 561A→C |
| Endothelial nitric oxide synthase | −786T→C | Endothelial nitric oxide synthase | −786T→C |
| G protein β3 subunit | 825C→T | Endothelin-1 | 5665G→T |
| Glycoprotein Ia | 1648A→G | Fatty acid–binding protein 2 | 2445G→A |
| Interleukin-10 | −819T→C | Glycoprotein Ibα | 1018C→T |
| Interleukin-10 | −592A→C | Insulin receptor substrate–1 | 3494G→A |
| NADH/NADPH oxidase p22 phox | 242C→T | Interleukin-6 | −634C→G |
| Platelet-activating factor acetylhydrolase | 994G→T | Paraoxonase | 584G→A |
| Thrombomodulin | 2136C→T | Plasminogen-activator inhibitor–1 | −668/4G→5G |
| Thrombopoietin | 5713A→G | Stromelysin-1 | −1171/5A→6A |
| Thrombospondin 4 | 1186G→C | Tumor necrosis factor–α | −850C→T |
| Transforming growth factor–β1 | 869T→C | Tumor necrosis factor–α | −238G→A |
| Tumor necrosis factor–α | −863C→A | | |

Fig.5

|  | Men ($n$ = 1107) | | Women ($n$ = 833) | |
| --- | --- | --- | --- | --- |
|  | Controls ($n$ = 533) | Subjects with hypertension ($n$ = 574) | Controls ($n$ = 340) | Subjects with hypertension ($n$ = 493) |
| Age (years) | 56.3 ± 11.0 | 59.6 ± 10.1*1 | 56.8 ± 11.4 | 62.6 ± 10.5*1 |
| Body mass index (kg/m$^2$) | 23.2 ± 2.7 | 23.9 ± 2.7*2 | 22.2 ± 2.9 | 23.6 ± 3.4*1 |
| Smoking (%) | 58.5 | 47.6† | 10.6 | 8.5 |
| Systolic blood pressure (mmHg) | 121 ± 13 | 161 ± 27*1 | 118 ± 15 | 164 ± 26*1 |
| Diastolic blood pressure (mmHg) | 72 ± 10 | 92 ± 16*1 | 68 ± 10 | 90 ± 16*1 |
| Diabetes mellitus (%) | 15.6 | 19.5 | 12.1 | 16.6 |
| Hypercholesterolemia (%) | 29.8 | 34.7 | 41.8 | 54.6*2 |
| Hyperuricemia (%) | 13.9 | 21.1*3 | 6.5 | 13.0*3 |
| Serum creatinine (μmol/L) | 81.4 ± 19.5 | 90.2 ± 39.8*1 | 62.8 ± 16.8 | 64.6 ± 30.1 |

Fig.6

| Gene | SNP | Dominant | | Recessive | | Additive | |
|---|---|---|---|---|---|---|---|
| | | P | OR (95% CI) | P | OR (95% CI) | P | OR (95% CI) |
| *Men* | | | | | | | |
| Chemokine receptor 2 | 190G→A | 0.0471 | 1.3 (1.0–1.6) | 0.0151 | 1.8 (1.1–2.8) | 0.0077 | 1.9 (1.2–3.0) |
| G protein β3 subunit | 825C→T | 0.0235 | 1.4 (1.0–1.8) | 0.0342 | 1.4 (1.0–1.8) | 0.0075 | 1.6 (1.1–2.3) |
| Glycoprotein Ia | 1648A→G | 0.7058 | | 0.0266 | 0.6 (0.4–0.9) | 0.7037 | |
| Apolipoprotein C-III | 1100C→T | 0.5137 | | 0.0373 | 0.8 (0.6–1.0) | 0.1592 | |
| *Women* | | | | | | | |
| Tumor necrosis factor-α | −238G→A | 0.0054 | 0.3 (0.1–0.7) | 0.6903 | | 0.0349 | 0.3 (0.2–0.9) |
| Tumor necrosis factor-α | −850C→T | 0.3200 | | 0.0354 | 5.0 (1.4–32.2) | 0.0336 | 5.1 (1.4–32.9) |
| Insulin receptor substrate−1 | 3494G→A | 0.0462 | 2.5 (1.1–6.6) | 0.8127 | | 0.0631 | |
| Glycoprotein Ibα | 1018C→T | 0.0484 | 0.7 (0.5–1.0) | 0.3777 | | 0.0215 | 0.6 (0.4–0.9) |

Fig.7

| Gene | SNP | Genotype distribution (%) | | | | | |
|------|-----|---|---|---|---|---|---|
| | | Controls | | | Subjects with hypertension | | |
| *Men* | | | | | | | |
| Chemokine receptor 2 | 190G→A | GG (54.6) | GA (38.9) | AA (6.5) | GG (49.7) | GA (40.1) | AA (10.1) |
| G protein β3 subunit | 825C→T | CC (29.9) | CT (48.9) | TT (21.1) | CC (24.0) | CT (50.7) | TT (25.3) |
| Glycoprotein Ia | 1648A→G | AA (0.0) | AG (6.6) | GG (93.4) | AA (0.4) | AG (9.3) | GG (90.3) |
| Apolipoprotein C-III | 1100C→T | CC (15.1) | CT (44.6) | TT (40.3) | CC (16.7) | CT (49.3) | TT (34.1) |
| *Women* | | | | | | | |
| Tumor necrosis factor-α | −238G→A | GG (94.6) | GA (4.5) | AA (0.9) | GG (97.3) | GA (2.7) | AA (0.0) |
| Tumor necrosis factor-α | −850C→T | CC (75.3) | CT (24.1) | TT (0.6) | CC (71.9) | CT (24.5) | TT (3.6) |
| Insulin receptor substrate-1 | 3494G→A | GG (97.9) | GA (2.1) | AA (0.0) | GG (95.2) | GA (4.4) | AA (0.4) |
| Glycoprotein Ibα | 1018C→T | CC (74.5) | CT (23.7) | TT (1.8) | CC (79.7) | CT (18.4) | TT (1.9) |

Fig.8

| Gene | Chromosomal locus | SNP | Genetic model | Odds ratio | 95% CI |
|---|---|---|---|---|---|
| *Men* | | | | | |
| Glycoprotein Ia | 5q23–q31 | 1648A→G | GG versus AA + AG | 0.56 | 0.35–0.91 |
| Chemokine receptor 2 | 3p21 | 190G→A | AA versus GG + GA | 1.65 | 1.04–2.60 |
| Apolipoprotein C-III | 11q23 | 1100C→T | TT versus CC + CT | 0.73 | 0.57–0.95 |
| G protein β3 subunit | 12p13 | 825C→T | CT + TT versus CC | 1.32 | 0.99–1.74 |
| *Women* | | | | | |
| Tumor necrosis factor-α | 6p21.3 | −850C→T | TT versus CC + CT | 4.63 | 1.02–20.93 |
| Tumor necrosis factor-α | 6p21.3 | −238G→A | GA + AA versus GG | 0.28 | 0.12–0.66 |
| Insulin receptor substrate-1 | 2q36 | 3494G→A | GA + AA versus GG | 2.10 | 0.83–5.30 |
| Glycoprotein Ibα | 22q11.2 | 1018C→T | CT + TT versus CC | 0.74 | 0.51–1.09 |

Fig.9

| Glycoprotein Ia (0 = AA = AG, 1 = GG) | Chemokine receptor 2 (0 = GG = GA, 1 = AA) | Apolipoprotein C-III (0 = CC = CT, 1 = TT) | G protein β3 subunit (0 = CC, 1 = CT = TT) | Odds ratio |
|---|---|---|---|---|
| 0 | 1 | 0 | 1 | 5.34 |
| 0 | 1 | 0 | 0 | 4.05 |
| 0 | 1 | 1 | 1 | 3.90 |
| 0 | 1 | 1 | 0 | 2.95 |
| 0 | 0 | 0 | 1 | 3.24 |
| 0 | 0 | 0 | 0 | 2.45 |
| 0 | 0 | 1 | 1 | 2.36 |
| 1 | 1 | 0 | 0 | 1.79 |
| 1 | 1 | 0 | 1 | 2.98 |
| 1 | 1 | 1 | 0 | 2.26 |
| 1 | 0 | 1 | 1 | 2.18 |
| 1 | 0 | 0 | 0 | 1.65 |
| 1 | 0 | 0 | 1 | 1.81 |
| 1 | 0 | 1 | 0 | 1.37 |
| 1 | 0 | 1 | 1 | 1.32 |
| 1 | 0 | 1 | 0 | 1.00 |

Fig.10

| Tumor necrosis factor-α (0 = CC = CT, 1 = TT) | Tumor necrosis factor-α (0 = GG, 1 = GA = AA) | Insulin receptor substrate-1 (0 = GG, 1 = GA = AA) | Glycoprotein Ibα (0 = CC, 1 = CT = TT) | Odds ratio |
|---|---|---|---|---|
| 1 | 0 | 1 | 0 | 46.86 |
| 1 | 0 | 1 | 1 | 34.71 |
| 1 | 0 | 0 | 0 | 22.31 |
| 1 | 0 | 0 | 1 | 16.53 |
| 1 | 1 | 1 | 0 | 13.13 |
| 1 | 1 | 1 | 1 | 9.72 |
| 1 | 1 | 0 | 0 | 6.25 |
| 1 | 1 | 0 | 1 | 4.63 |
| 0 | 0 | 1 | 0 | 10.12 |
| 0 | 0 | 1 | 1 | 7.50 |
| 0 | 0 | 0 | 0 | 4.82 |
| 0 | 1 | 1 | 0 | 3.57 |
| 0 | 1 | 1 | 1 | 2.84 |
| 0 | 1 | 0 | 0 | 2.10 |
| 0 | 1 | 0 | 1 | 1.35 |
| 0 | 1 | 0 | 1 | 1.00 |

Fig.11
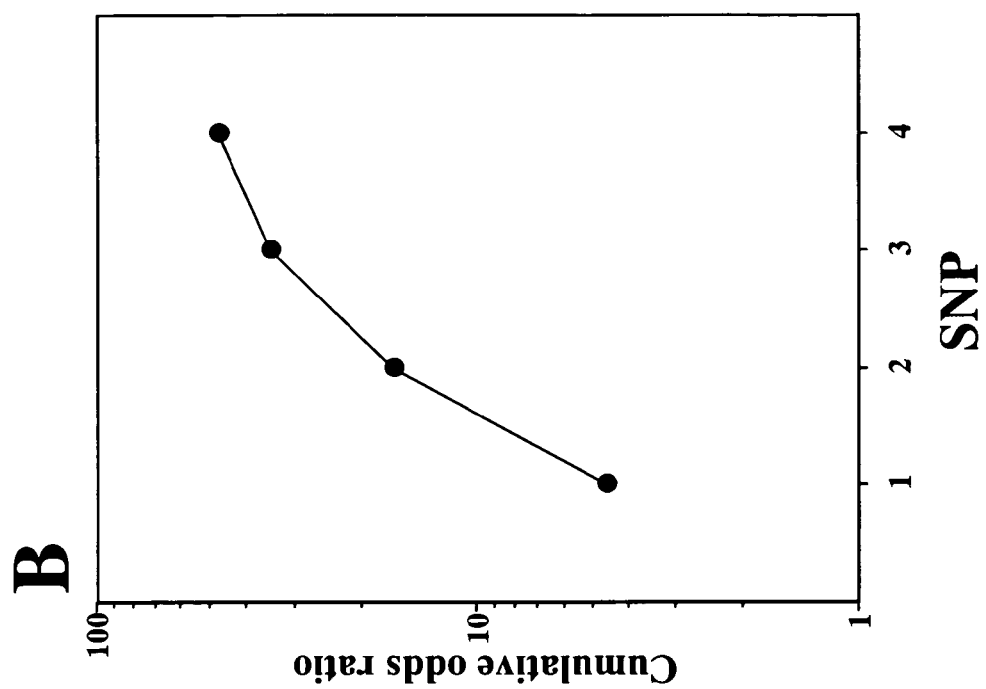
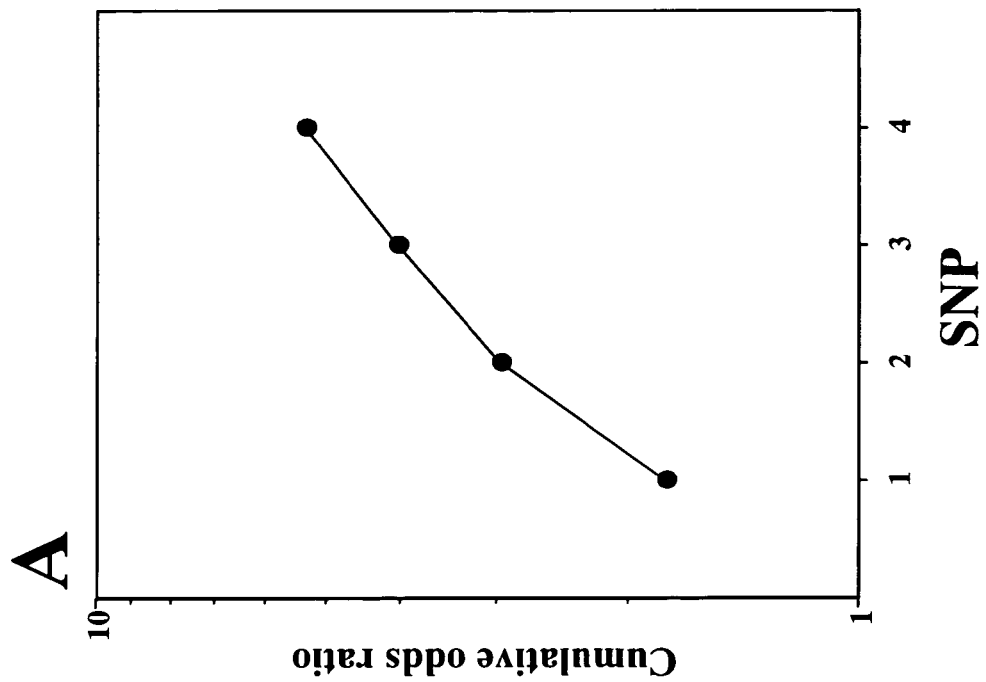

SEQUENCE LISTING

<160> NUMBER OF SEQ ID NOS: 36

<210> SEQ ID NO 1
<211> LENGTH: 5373
<212> TYPE: DNA
<213> ORGANISM: Homo sapiens

<400> SEQUENCE: 1

| | | | | | |
|---|---|---|---|---|---|
| gaattcctgc | aaacccagcg | caactacggt | cccccggtca | gacccaggat | ggggccagaa | 60 |
| cggacagggg | ccgcgccgct | gccgctgctg | ctggtgttag | cgctcagtca | aggcatttta | 120 |
| aattgttgtt | tggcctacaa | tgttggtctc | ccagaagcaa | aaatattttc | cggtccttca | 180 |
| agtgaacagt | ttgggtatgc | agtgcagcag | tttataaatc | caaaaggcaa | ctggttactg | 240 |
| gttggttcac | cctggagtgg | ctttcctgag | aaccgaatgg | gagatgtgta | taaatgtcct | 300 |
| gttgacctat | ccactgccac | atgtgaaaaa | ctaaatttgc | aaacttcaac | aagcattcca | 360 |
| aatgttactg | agatgaaaac | caacatgagc | ctcggcttga | tcctcaccag | gaacatggga | 420 |
| actggaggtt | ttctcacatg | tggtcctctg | tgggcacagc | aatgtgggaa | tcagtattac | 480 |
| acaacgggtg | tgtgttctga | catcagtcct | gattttcagc | tctcagccag | cttctcacct | 540 |
| gcaactcagc | cctgcccttc | cctcatagat | gttgtggttg | tgtgtgatga | atcaaatagt | 600 |
| atttatcctt | gggatgcagt | aaagaatttt | ttggaaaaat | ttgtacaagg | ccttgatata | 660 |
| ggccccacaa | agacacaggt | ggggttaatt | cagtatgcca | ataatccaag | agttgtgttt | 720 |
| aacttgaaca | catataaaac | caaagaagaa | atgattgtag | caacatccca | gacatcccaa | 780 |
| tatggtgggg | acctcacaaa | cacattcgga | gcaattcaat | atgcaagaaa | atatgcctat | 840 |
| tcagcagctt | ctggtgggcg | acgaagtgct | acgaaagtaa | tggtagttgt | aactgacggt | 900 |
| gaatcacatg | atggttcaat | gttgaaagct | gtgattgatc | aatgcaacca | tgacaatata | 960 |
| ctgaggtttg | gcatagcagt | tcttgggtac | ttaaacagaa | acgcccttga | tactaaaaat | 1020 |
| ttaataaaag | aaataaaagc | gatcgctagt | attccaacag | aaagatactt | tttcaatgtg | 1080 |
| tctgatgaag | cagctctact | agaaaaggct | gggacattag | gagaacaaat | tttcagcatt | 1140 |
| gaaggtactt | ttcaaggagg | agacaacttt | cagatggaaa | tgtcacaagt | gggattcagt | 1200 |
| gcagattact | cttctcaaaa | tgatattctg | atgctgggtg | cagtgggagc | ttttggctgg | 1260 |
| agtgggacca | ttgtccagaa | gacatctcat | ggccatttga | tctttcctaa | acaagccttt | 1320 |
| gaccaaattc | tgcaggacag | aaatcacagt | tcatatttag | gttactctgt | ggctgcaatt | 1380 |
| tctactggag | aaagcactca | ctttgttgct | ggtgctcctc | gggcaaatta | taccggccag | 1440 |
| atagtgctat | atagtgtgaa | tgagaatggc | aatatcacgg | ttattcaggc | tcaccgaggt | 1500 |
| gaccagattg | gctcctattt | tggtagtgtg | ctgtgttcag | ttgatgtgga | taaagacacc | 1560 |
| attacagacg | tgctcttggt | aggtgcacca | atgtacatga | gtgacctaaa | gaagaggaa | 1620 |
| ggaagagtct | acctgtttac | tatcaaaaag | ggcattttgg | gtcagcacca | atttcttgaa | 1680 |
| ggcccccgagg | gcattgaaaa | cactcgattt | ggttcagcaa | ttgcagctct | ttcagacatc | 1740 |
| aacatggatg | gctttaatga | tgtgattgtt | ggttccacac | tagaaaatca | gaattctgga | 1800 |
| gctgtataca | tttacaatgg | tcatcaggcc | actatccgca | caaagtattc | ccagaaaatc | 1860 |
| ttgggatccg | atggagcctt | taggagccat | tccagtacct | ttgggaggtc | cttggatggc | 1920 |
| tatgagatt | taaatgggga | ttccatcacc | gatgtgtcta | ttggtgcctt | tggacaagtg | 1980 |
| gttcaactct | ggtcacaaag | tattgctgat | gtagctatag | aagcttcatt | cacaccagaa | 2040 |

```
aaaatcactt tggtcaacaa gaatgctcag ataattctca aactctgctt cagtgcaaag    2100
ttcagaccta ctaagcaaaa caatcaagtg gccattgtat ataacatcac acttgatgca    2160
gatggatttt catccagagt aacctccagg gggttattta agaaaacaa tgaaaggtgc     2220 ctgcagaaga atatggtagt aaatcaagca cagagttgcc ccgagcacat catttatata    2280
caggagccct ctgatgttgt caactctttg gatttgcgtg tggacatcag tctggaaaac    2340
cctggcacta gccctgccct tgaagcctat tctgagactg ccaaggtctt cagtattcct    2400
ttccacaaag actgtggtga ggatggactt tgcatttctg atctagtcct agatgtccga    2460
caaataccag ctgctcaaga caacccttt attgtcagca accaaaacaa aaggttaaca     2520
ttttcagtaa cactgaaaaa taaaagggaa agtgcataca acactggaat tgttgttgat    2580
ttttcagaaa acttgttttt tgcatcattc tccctaccgg ttgatgggac agaagtaaca    2640
tgccaggtgg ctgcatctca gaagtctgtt gcctgcgatg taggctaccc tgctttaaag    2700
agagaacaac aggtgacttt tactattaac tttgacttca atcttcaaaa ccttcagaat    2760
caggcgtctc tcagtttcca agccttaagt gaaagccaag aagaaaacaa ggctgataat    2820
ttggtcaacc tcaaaattcc tctcctgtat gatgctgaaa ttcacttaac aagatctacc    2880
aacataaatt tttatgaaat ctcttcggat gggaatgttc cttcaatcgt gcacagtttt    2940
gaagatgttg gtccaaaatt catcttctcc ctgaaggtaa caacaggaag tgttccagta    3000
agcatggcaa ctgtaatcat ccacatccct cagtatacca agaaaagaa cccactgatg     3060 tacctaactg gggtgcaaac agacaaggct ggtgacatca gttgtaatgc agatatcaat    3120
ccactgaaaa taggacaaac atcttcttct gtatctttca aaagtgaaaa tttcaggcac    3180
accaaagaat tgaactgcag aactgcttcc tgtagtaatg ttacctgctg gttgaaagac    3240
gttcacatga aggagaata ctttgttaat gtgactacca gaatttggaa cgggactttc     3300
gcatcatcaa cgttccagac agtacagcta acggcagctg cagaaatcaa cacctataac    3360
cctgagatat atgtgattga agataacact gttacgattc ccctgatgat aatgaaacct    3420
gatgagaaag ccgaagtacc aacaggagtt ataataggaa gtataattgc tggaatcctt    3480
ttgctgttag ctctggttgc aatttttatgg aagctcggct tcttcaaaag aaaatatgaa   3540
aagatgacca aaaatccaga tgagattgat gagaccacag agctcagtag ctgaaccagc    3600
agacctacct gcagtgggaa ccggcagcat cccagccagg gtttgctgtt tgcgtgcatg    3660
gatttctttt taaatcccat atttttttta tcatgtcgta ggtaaactaa cctggtatttt   3720 taagagaaaa ctgcaggtca gtttggatga agaaattgtg gggggtgggg gaggtgcggg    3780
gggcaggtag ggaaataata gggaaaatac ctattttata tgatggggga aaaaagtaa    3840 tctttaaact ggctggccca gagtttacat tctaatttgc attgtgtcag aaacatgaaa    3900
tgcttccaag catgacaact tttaaagaaa aatatgatac tctcagattt taaggggaa    3960 aactgttctc tttaaaatat ttgtctttaa acagcaacta cagaagtgga agtgcttgat    4020
atgtaagtac ttccacttgt gtatatttta atgaatattg atgttaacaa gagggaaaa    4080 caaaacacag gttttttcaa tttatgctgc tcatccaaag ttgccacaga tgatacttcc    4140
aagtgataat tttatttata aactaggtaa aatttgttgt tggttccttt tataccacgg    4200
ctgccccttc cacacccat cttgctctaa tgatcaaaac atgcttgaat aactgagctt     4260
agagtatacc tcctatatgt ccatttaagt taggagaggg ggcgatatag agactaaggc    4320
acaaaatttt gtttaaaact cagaatataa catttatgta aaatcccatc tgctagaagc    4380
```

-continued

```
ccatcctgtg ccagaggaag gaaaaggagg aaatttcctt tctcttttag gaggcacaac    4440
agttctcttc taggatttgt ttggctgact ggcagtaacc tagtgaattt ttgaaagatg    4500
agtaatttct ttggcaacct tcctcctccc ttactgaacc actctcccac ctcctggtgg    4560
taccattatt atagaagccc tctacagcct gactttctct ccagcggtcc aaagttatcc    4620
cctcctttac ccctcatcca aagttccac tccttcagga cagctgctgt gcattagata     4680
ttagggggga aagtcatctg tttaatttac acacttgcat gaattactgt atataaactc    4740
cttaacttca gggagctatt ttcatttagt gctaaacaag taagaaaaat aagctagagt    4800
gaatttctaa atgttggaat gttatgggat gtaaacaatg taaagtaaaa cactctcagg    4860
atttcaccag aagttacaga tgaggcactg gaaaccacca ccaaattagc aggtgcacct    4920
tctgtggctg tcttgtttct gaagtacttt ttcttccaca agagtgaatt tgacctaggc    4980
aagtttgttc aaaaggtaga tcctgagatg atttggtcag attgggataa ggcccagcaa    5040
tctgcatttt aacaagcacc ccagtcacta ggatgcagat ggaccacact ttgagaaaca    5100
ccacccattt ctacttttg caccttattt tctctgttcc tgagccccca cattctctag     5160
gagaaactta gattaaaatt cacagacact acatatctaa agctttgaca gtccttgac     5220 ctctataaac ttcagagtcc tcattataaa atgggaagac tgagctggag ttcagcagtg    5280
atgcttttta gttttaaaag tctatgatct gatctggact tcctataata caaatacaca    5340
atcctccaag aatttgactt ggaaaaggaa ttc                                 5373

<210> SEQ ID NO 2
<211> LENGTH: 50000
<212> TYPE: DNA
<213> ORGANISM: Homo sapiens

<400> SEQUENCE: 2
aagcttcagt atgcaaattt tcaatgacat gtgcctgtgg attctgaaaa ttcacagatc      60
tgtctatcct tagctgagac tgaaggcatc tacttcccaa tgaccaaatc ctggtgctgt     120
ggcgacactg agcaggaact ccattagaat atcaatatca ctctgcagac attccatgat    180
gtaagctatg ttttctcttg ttgcaattac acttaattta ccaccagctg cttcaatgtc    240
atgggctatc ttgaaaaatg aagctccttt cgtagtcaaa ctggatgcaa gacacagcaa    300
atgagaagtt actaaattgt tggagtcctc atagctactg cctgctttaa tgaacaaacc    360
aattcttgat gcagggcata gttttccaaa ggagaaatca taaaccatt tggaaatttg     420 atgatctcaa ggtcctgatg atgtggagcc actcctatgg gggtagctgt ggctttaact    480
ttgggggcaa ctttgaggga ataaagtctc aaaaagaggg aataaagtct caagattgtt    540
cgtgacccat agtaacttct ggcttaaagg accattcggc aagttttaa atgtatttc      600 tataatttcc atgtagttct ttatattttc tatttcttat ttaaaacctc tattttagct    660
cgtttccttt gacactgctc tggcaggaa agggtggca ctgcctcatt actgccaggt       720
aggggtagaa gtccattatc cacttggtct ccattgatac ccaaagtggg gagaggctcc    780
tgttactgct ggtgagggtg ggagtccccc cactaagttt ctgctaatac tgtcctggtg    840
gcttgctact attcccatga agcctccact gatactacat tacttttggg tggtggcaaa    900
tgtcctgcct ctccactagc cctcctgctc taaaacaacc cgagtaggga gtgggaagga    960
agctttgtta ctggtaggtg ggagctgaag tccagacttg ccacattgtc ccactgatgc   1020
tacagggagg aggaagcggg ccacattact gcctgatagg gatgaaagcc ccagctccct   1080
acctggcctt cgctgatacc agcctgctac aggagtgaag agagatttga aggcctcaat   1140
```

```
atagcctgtc gagggtggaa gtcttgctcc caatgggcct ttagcagcat gggtgggtgt    1200
ggggccatag ctgtctctgt actgcttggc tagagtggag tatttgaggt ccaaaagttt    1260
tctgtctttc tagccctttg gttagaaaga gcagactttt gttggaagta ttttttttgtg   1320 tttacctgtt gtatttccag gttcctagct tctccagcac agtctgggat gtgtgagaca    1380
cagagaaaat ccagtgatgt tactaccgta tggtttcttg ggtcccaacg tctctagcta    1440
atctgctcca ccttttggag ttttcttatt tgttttagat cagggattta gtcatattta    1500
ataggagaaa tatggaaaaa tacttctact ctatcttcct ggaagttcct gtttattttt    1560
tatgtccttt tcctctggct agaccgtaag agacttacga aacaaacact tacacattct    1620
actaaactca atgtccaaag tttgtgaact tcttgaatat tgcttgttca tttccacccc    1680
cagtcactga ctgaatctcc ctgctgtctg tctacaatgc caatgagctt ctggttaact    1740
tcttctcatg catgcttagg caacaacttc ccagttttac tacacttgcc catccctagt    1800
tttgttgttg cttaatccct tggcctagtg ccaccatact cctccagcag agcaaccaat    1860
tcttacatta taggacagca catatccact aaaaacagtt catgccacac caaccacatt    1920
tccctttgtc aacaaaatta cttgatagat aattccagga atgcctgatg aagctgattg    1980
acaacaagat atttggcaga ctctctgctg cctatacata ccttagcatg tggaactcaa    2040
gtaatgagag gtccatttaa ttggattgaa ttgggctgga taggattgga ttgaatcctg    2100
tgggatggct aggctaaatt agaaatgaag actagtttaa cagcagtatc caaggatagt    2160
tgactaatga gttaattta ctctcaaaga cagtctttag tagtaagctg taatgcatta     2220
tatcaaacta ttttccagtc aatgatttat aagttacttg aataaggatg ctaaagatgt    2280
gccttattga aatggcaatt agcacaaagt tgggaatgaa atctaattag ttaaataaca    2340
gaatcacata aaaaggact tgaataaatg tagcatccta ccatgttcct ggatagaaag     2400
actgctatcg taaagatatt cattctcctc aggttaaatt ataaactcaa tgcaattcaa    2460
caggatttta aaaaactaga caaagtgatt ccaagtttac gtggaaaata aaatgtgagg    2520
gaccaaacaa tatttgaaaa agaaagagaa taaaatctca tccttccaga taccacaatg    2580
tattataaag caatagtaat taacatgagg gcagaaatga gcaagcaagt gaacaaaata    2640
agacagatag tcacaggaaa ctcatatatt tataggtgct ttgcgtataa tgaagatggt    2700
ccttcaaatc agttgggaaa agatgggtta ttcaataaat ggtgttgggt aaaattggtt    2760
atacattggt gagaaataaa gtgaaactcc tactttgtat catatgcaaa aaatagattc    2820
cagacagatg aaatatttaa atgtaaaaaa taaaattcta aaactactag aaaaaaaaga    2880
agaatatttt tattccttg aaatagaaaa ggtcttacta agcaaaacac agaagtaata    2940
aatgaataaa tgaagacaaa tatgataaaa ataagttaaa aatataagca atctttcttt    3000
gttttttttt cacctttcct agaaaaaaat atataggcaa cttgttaagc aaggtagatt    3060
acaagaaaat atttacaaca tttgacaggc cacagattat tatccagcct catctgataa    3120
gaaaacttca acataaagat atctgttttt tttcttataa ggttcctcaa agtgagccaa    3180
tcacttctta agctgaacaa aaaacaaaac agaagtgatc ttttccaata atgaaaacaa    3240
acattgacag agcagctgta ggatcctttc aggcaaatta tgaaaaggtg cccttttctca   3300 gaaaccacag ttaccattca gctttgtgac cagaggtttg actgtaccct agtccctact    3360
agcaacccaa ccacataacc aacttcaaag gtcctgaatg actgtgttgt acttaatggc    3420
agatgatcta tctcccattt ttgtcctaag gattttccaa gataatatat ttctgcattt    3480
```

```
gttttgctttt tacttcactc caaattgaaa tctatttgtg ggataagact aaagaaatgc   3540
ttataggaaa attgatagca ccaaattcct atcttaaaaa atgaaaaagg tttcaaatca   3600
atgacctcag cttttacttt aagaaaatag aaaaagcagg ataagctaaa gccaaagtaa   3660
acagaagaaa ggaaattata aagataagag cagaaatcaa tgaatagaaa acaaagaaa    3720 aaaatcaaac caaacagctg attcttttaag cagatctata aaattgataa aactctagcc  3780
agattgatca agtaaaaaag agagaagaca caaattacca gtattaagaa tgagagaggc   3840
aatatcacta cagatcctac agatataaaa agtataaggg catactttga ataattttat   3900
gactataaat taggcaactt agataaaaca aatttcttga aagacacaaa caaccaaagc   3960
tcacctaaaa tactcacaaa ttgaatagtc ttatagctat tacaaaattg aggccaggcg   4020
cagtggctca agcctttaat cccagcactt tgggagggct aggaaggcgg atcacgaggt   4080
caggagtttg agaccagcct gactaacatg gtgaaaccct gtctctacta aaagtacaaa   4140
aattagccag gcttggtggt gcgtgcctgt aatcccatct actcaggaga ctgaggcagg   4200
agaattgctt gaacctggga ggcaaagttg tggtgagccg agatcgcgcc actgcacttc   4260
agcctgggca acagaacaag actccgtctc aaaaaaaaaa aaaaaaaaaa aaattgaaat   4320
tatagttaaa agtcttccca caaagcaaac tctagaccca gatggcttca atggtaaatt   4380
ctactggaca atcaaacagg aaacagtaat aattctccac aatgtctttc ataaaattga   4440
tgcggaggag atactctcca actcattcta tgaaactagc attaccctga taccaaaatc   4500
atacagagac agtgtaggaa acaacagat cagtatcctt catgaacata aatgaagtac    4560
aatgcagtct tatgcataaa tcagagcttc attgttctac agataaggta atgtaggatt   4620
gttggttgcc cctccaggtc tgttaaattc acctccttcc ccagagagca tccttcttaa   4680
ggacagggag cctcaatatg tcagtcctca cagcacctcc ctcagtcttc agcacttacc   4740
agctcatcac cacaaccgat accacattgg ataatttcat gaattacttt agagcaaatg   4800
caagagaaaa aatggatttt tatataggag aagaaggagg aaattcttgt ggatttggta   4860
cagaataggg ccaagggaaa attacagatg taaaagaaa agtgtgtgaa atagtatcct    4920
tagtgctcac aaatacaatg atttcattgt ttttaaaaat aaaaaatgac aaatgtctaa   4980
tgcttggtgg taatgcttta ttgaatgtgt gttatacact ggttcctcat tcctgaagtt   5040
agaaataata ccttcctctt ttcatttggt tatgtttgct gaaacaaatc aaaggctgag   5100
attgaaacac atgctacttc aggtggatga ccttactact aagctcatca caacagcact   5160
tacagctgaa gaccccagag tcctacctaa ctttttgtcac aacccagatt ttggccatgt   5220
agttctgggc cttaccatta aagcagacag aagtcagagg aatgactcct ttccacttga   5280
agtgagctgc aggcttctag gaaaggcaag atgcacattt ccctcctgtg gagcataaag   5340
cctttgtaat tcaggactta ggacccatat ggatttgaaa tattatgaca ttggagctgg   5400
agtggttggg gacaacacca gtagtgttat aggccatgga atgtcaaaag aacatggaac   5460
cctgttaaaa tcattaaaca tcaaaactct cccctcctct ggtgatatgg tttggctgtg   5520
tccccatcca aatctcatct tgaactccca tgtgttgtgg gaggcaccca gtgggaggta   5580
attgaatcat gggggcaggt ctttcccatg ctgttttcac gatactgaat aagtctcaca   5640
agatctgatg gttttataaa ggggagcttc ctgcacaag ctctcttctc ttgtctgcca    5700
ccatgtgaga catgcctttc accttccgcc atgattgtga ggcctcccca accatgtgga   5760
acttttaagt tcattaaacc tcttcctttt gtaaattgct cagtctcaaa tatgtctttα   5820 tcagcaacgt gaaaacagac tatctgattt tctgtgggat gtggattatg accatggaca   5880
```

```
gagcataact gggacagagc tggaaaaaat attaattagg tgcttaaaaa tatttgttag   5940
aactatcttc atgaatgaga atcaatcctg tttccatggt gattcaccag gcatcaattc   6000
caagcatcca tgaatcagaa aagtcctatc ttctcttagt tatcatccag gactccaagg   6060
aaccataatt agccaacctg ttcacatttc cttttcattc actagcctcg aagtttccag   6120
gggacaggga ctctgtccta ttcatttctg taaccttacc acctgaccca gaatagctgt   6180
tccctgaaga tttggtggat tataaatgtg gatgtcttat ttctttgaaa gtgtgagctt   6240
caggtactga tcacgttatt ccaattatca atttagtatc tttcttcacc attaaactgt   6300
gaaattcttg agggaagaac ctatgactga tttatctctg taaactcatg ccaccagtat   6360
tcaaaatcac acctagcaca tagtaaacac tcaatgtttg ttgaatgact gaaggaatgg   6420
atgaaaatga acctccttgc ttctgaccag tggatgagtt gcttggccgt gttcctacag   6480
cctagagctc atcccctaaa gcatctgaag ttacccatta gtgcaatggt tcttgaacgc   6540
tggtgttgat cagaatcatc tggatgccca ggttctctga ataagatag ggtctaggca   6600 tttgtatttt taccaaggag gtgtgatgga gtcagatgca agaaggctag ttgaagaaac   6660
cacatgagag tttagtgtag tgtattagaa gactggtttg gctctgtcgc tagtggctac   6720
atcatcttgc tcaagtcatg ccagtctcag gacctcattc agtctcttca gctgtaatat   6780
gggtgggttg caccacataa ccagaaagat cccttccagc tctacccact tacaacatgg   6840
tcaaatttgg tctgattttt taaatcgtag tacaatatat atgacataaa attcaccatt   6900
ttagccactt taaatgtaca attctgtagc attaactaca ttcacattgt tgtgcaacca   6960
tcactaccgt ctacttccag aactcttcat cttgcaaaac tgaacctctg ttgtcattag   7020
tcactaacta ttcctctccc cccctccttc taggccctgg caatcaccat tctactttct   7080
gtcgctatga atttgactac tctaggtaac ttatataagt ggaatcacag catttgccct   7140
attatgactg gtttagttga cttagcacaa cctcctaagg ctcaaccaca ttttagcatg   7200
tgtcagaatt ttctttgttt ttaaggctga ataatattct gttgtatctg taaataacat   7260
ctttattcat ttgtccatca acagactgtt gagttcctcc catctttga ctattgtgaa   7320 aaatgctgct atgaacctga gtgtacagac atctggttga gtactgcttt caattcattg   7380
tttatatgga tcatatggta atttatgtt aattttttt ggaactgcta cattgttttc   7440
cacagtgtac atcattttac atttccatca gcaatgcaca aaggttccaa tttctccaca   7500
ttcttaccaa cattttttat tttctgtttc ttatttattt gttatttat tctgagacag   7560 agtctcactc tgtcacctag gctggagtgc agcagggtga tctcagctca ctgcaacctc   7620
tgcctcccat gttcaagtga ttctcctccc tcagcctccc aagtaaatgg aattacaggt   7680
gcccaccacc acgcccaggt aattttgca tttttttag tagtgatgag gtttcaccat   7740
gttggtcagg ctggtcttga actcctgacc tcaagtgatc cacccgcctc agcctcccaa   7800
agtgctggga ttacaggtat gaaccactgc acccaggcca ttttttgctt tttagataat   7860
agtcatccta gtgggtatga agtggtattt cattgtggtt tgatttata tttccctaat   7920 gatcagtgat attgagcatc tttcaagtgc ttattggcca ttttcttctt tggagaaatg   7980
tctatgcaag tcctttgctc attttttaat ccagttgctt tttgttattc ttttgattt   8040 gaaagtgttc tttataccte ttgtatacta atcccttatc agatatgatt tataaatatt   8100
ttcttctttt ccatggattg ccctttttac tctgttgata gtgttctttg atacaaaata   8160 attttttaatt tgaatgaagc ccaattaatc tatttttgtt tcttttgttg cctgtgcttt   8220
```

```
tggtgtccta tccaagaaac tgttgccaaa tccaatgtca taaagctttt tcccatgctt   8280
ccttctaaga gttttgtagt tacagctctt gtatttaggt atttgactat tttgagttaa   8340
tttttgtaca tcgtataaaa taagaatcca atttttattt tattttactt tttgtatgtg   8400
gatatccaat ttccccacca ccattcattg aaaagactgt cctttttccta tcgaatggtc   8460 ttggcaccct tgtaaaacat aatttgacca tatatgtgag ggtttatttc tgggctctct   8520
attctattct attctattct attctattct attctattct attctattct attctattct   8580
attggtccct atgtctttct ttattctagt accaccattt tgctcatcat aactttgtag   8640
taagttttga agtcaggaat cgtaagacct ccagctttgt tcattttcaa ggttgttttg   8700
attattcaag gtcccttgat agtccatatg aatttcagga tggattttc tatttctgca    8760 aaaaaaaaa aaaaaaaaa aaaaatcatt gaaattttta aacagattgc attaaatctg     8820
tagattgttt tgggtagtat tgacatttaa caacattaaa tcttccaatc aatgaactag   8880 gctatttta tttatttttt ctgtttcttt gagctacttt tgtagtttc agtgtataag     8940 tttttgctac ctggttaggt atacttctaa gtattttcta cttttgatg ctattgcaca    9000 ttgaatcgtt tcttaatttt ggtggtagcg gggattgtgc attgttagta cataaaaatg   9060
caactcattt tttgtgtgtt gattttgtat cctgcagctt taacaaattc atgttagttc   9120
taacagactt attctatgaa tcattagggt tttctacata aaagatcatg tcacctacaa   9180
acagagataa ttttactcca cccccttcccg ttgcaatgcc ttttatgtct ttttcttgcc   9240
taattgttct ggctaagact tccactacca tgttgaatag aagtggtgaa agtagacatc   9300
cttgtcttgt tccaatctta gagccaaagc tttcagtctt tcacggcctg aaagactttg   9360
taatatgttc tcaaggttaa agaacttcag aagttttcta agcaagagac cattttatta   9420
acttagttgg cagcaattct gagagattag aatgaaaaga tagaggataa gaagtatctg   9480
gcaggtataa tatattgagt gtgctgaata tacttttagt tttgtatagg tgttaaaaaa   9540
tggcaaagga ggccgggcgt ggtggctcac gcctgtaatc ccagcacttt gggaggccga   9600
ggcgggcaga tcatgaggtc aggagatcga accatcctg gctaaaacag tgaaacccta    9660
tctctactaa aaatacaaaa aactcgctgg gcatggtggt ggacacctgt agtcccagct   9720
actcgggagg ctgaggcagg agaatggtgt gaacctggaa ggtggagctt gcagtgagcc   9780
gagatcacgc cactgcactc cagcctgggc gacagagaga gactccgtct caaaagaaaa   9840
aaaaaatggc aaaggaaaga atgaaaaata agcaaggtc ccagaagagg ccaaaaatct    9900
taatcaaaat tgactgaaca ttacggaatg aaatggtttt ccttttactc caattaacga   9960
cttcacaaga agattccatc ctcgtttata agattaaccc aaaaccagca cttaaaacca  10020
gaagccttga aaggatggag tttggggacc cttctcatgt ctattcccag aagggggtct  10080
tcttctgggg tcctgtcccc taaagagcta ggcaaaaagt atgcttgcca catctgttga  10140
aagatagaaa gttggtctaa aaatacatga gagggaactg aaacatttca gagaaggcaa  10200
gactcagaag taagaaacca aaagaggaag gtaaaattct agttacaaag aaaagaggaa  10260
tggaaattaa attgtcttac agagaaaatc cagaactgcc ccctcttccc ttactactcc  10320
atcaaaaaag gggaaaaata gtcaatggga aagttttgag aaaaatagat ctctgcattc  10380
ttctggttga gaattcagac aacttgaact agagagctgg gtaatttctt gactaaaggt  10440
gtgttagatc tgaaagggtt tttcttaaaa ttgtctgtgt tcatccctcc catcttagag  10500
aggaacacag gataagagac ctctggagct cccccagggt caccgagcta ataggatcag  10560
agacaaagct acaaagtcat tttctgacat ctctccaggg ctctttttt ctggaccccc    10620
```

-continued

```
catatcaaca tgatgtattt attacattgg attagcaact ctccttgagc tttcctcagt   10680
accaggttta catctcagtc tgtgggtctc agagaaagta cccaatcagc agcaacatta   10740
cctggaaact catcagaagt gcccctcctc agccccaccc cagatctatg caatcagaaa   10800
ctctggaaat gcaggccagt cctaacaagc ccaccaggga attctggtgc actaaggttt   10860
gagatccact gatcaaagaa ataatattcc ttttcttcat tataatagca tgaataataa   10920
ctaacatgta tttcacaatt tacaaagag ctttatgctc ttgttaaatt tgagggtagt   10980
cttctcaaaa tctctgtgag gctagaaagt cagatattga aacacctgtt ttatgggttc   11040
aaagataggt tcaaaagaga gtaaatgatt gttggggtgg caggtccaga gagggcagga   11100
tcaaaactgc aattgagtct tctgccttat aaaccagcat agcttcccca aggcacgtca   11160
cttctcgata aaatggtgac aactagagtg tcctttcaga tcattcttag aagcatggag   11220
tgctaggtca attgtgtaat tgatgaggaa ataataatac taagaactcc catcttctac   11280
gtccttatat acaatcctgt caggtagaag ctgagtctca gagagaacaa gttgccctcc   11340
caggaccacc aggtaagctc ggcatagctg tgcttagaat gtaggctgtc tggcttctgg   11400
gcttgcctgc ccagggaggc tttgtgggtt ctacttggtc atccagatca cagaggggca   11460
gcactgactc ctacccagtg ctcttgactg tacatctaat actttctact aagaaaaccc   11520
cttctcttta gaccaatggt tttcaaatct tggtgtgcat tggaatcacc tggaaagctt   11580
gttaaaacac agattgtccc accccaagag tttctgattc tgtaggctgg ggtggggacc   11640
catgaaagtg catttctaat aaggtcccaa gtgatgctga tgccaccagt gtgtggacaa   11700 cccctttgagt ggtgaagctc tggacaccct aatttgcaag gctaatcagg catatgtggc   11760 aaaatgaatac gaactgaaat tctgactcca atatcttcac tgatattcct aatccatagc   11820
atacacacag tcccattcgt ttcccttta gcttttaatc tacatttatc ctttcttcct   11880
ctgccactgc cttctctcca gttagctcaa accaggtaac ataaccgc ctcctaactc   11940 atccgcccag ttggtttctt tggctttaat ctagacttct tatctccacc agatttgcct   12000
taccaaagca ccaatttctt aaggcagggt tagaattaaa aatcttctgt tcctcctcat   12060
tgcctaaaac tcctaaactt atgattcaag gtcttccatg accttcatgg accagtctaa   12120
cgttttagcc tgtcctaagt gacatgcctc caccacatac ttcatgcttt ccactttctt   12180
tctccatgtc tttgttcatg catttccatt tcttctacct gcgatgtcct ccttcgccat   12240
ctctgtagat ttaaaaatcc tacagggctc atctcaaatg cccttcctt catgaagcct   12300 ttcatgaaat ccccatcgag aggttttccc tcctctcagc tctccaaagc acagatgtct   12360
gcgtttgtgg ctattatctt acgttgtttt gtattaaat ttctccagct ttacacattt   12420
gtcatcctct taaggacaaa catcttatta tggtcaatgt gaagctatag aggataattt   12480
aatgaaatat tccaagggct agtcattaca catgactgat ttatctctgt aaactcatcc   12540
acactcatcc acctgatttt gattggccaa gttaatgaat cagagaggaa aagatggtaa   12600
aaatataata aaaatctcct aggtagtctc acatcccaca gagcccag taatgaaatg   12660 aggccctgag ataatacttt atgaacaata aaactccggg ttctattgac agtgaagcaa   12720
gacctgagag agaaggctaa attcccttgt gtctagctgc cacaatcttc tgagaataat   12780 ggccttctt cccgtctgcc ttctgaatca taggcaaatt tttctcttg tgatcccta   12840 atacagaaag gggaagtcaa ataaaatata tacaaggaga aggattctgg gagacagagt   12900
ttcttgattc ccttctgcat gctcctcctc aaaagccttt atgagcttac cttacatta   12960
```

```
aattcttttta aacaaggcat tatgtggtct ggtcttttcc agctccacac accttcacac    13020
tacattcccc ccagctaatt ctgctctggg aacactgacc ttcttttagt tctttgaaca    13080
cattgatttc tggtcaagat gactcagtaa cttcaacctt tgttgtgccc ttggtgctgt    13140
gaagatatag atatatatta accactgcac accagaaatc agaaatagca aacagagaa    13200
taaagtcatt gagccatctt ctgagctcca aaagacaaat tttctccaaa aagacaaatt    13260
caggctctaa aacaatacct taaggaacca gaagtggaat agaaaattaa ggtggtaagc    13320
agggctaaac cacatgcctg ttgagcccag gtttggaaga agacaatggc aggtaggaat    13380
gtggtttctg atgggtaata ggtactgttt tcatttactt tctgttgctt ataacagaat    13440
atctgaaact gggtgcttta taaagaaaag gaatttatgt cttgcagtta gggaaactga    13500
gaagtcaaaa gttgagggct gcaattgaca agtgccttct tgctggtggg gatactctga    13560
agagtcttga ggtggtatcg ggcataccac tctcagtgag gggactgagc atactaggtc    13620
aggtctttct tcctccttt ataaagctat cagtcccact cttatgataa cccattaatc    13680
cattaactga ttagccaatt aatccatgaa tggattaatt cattcatgag ggcagagcct    13740
tcctgaccca aacacctctt aaagactcca cctctcaata ctgccacatg ggggattaaa    13800
tttcagcatg agtttttgat gagacaaata ttccaatgat agcagttatt aaaagtacat    13860
gcttgagaga agggggattgg agtcagcctc agtgctaaaa ctcaaaagct aggatgaggc    13920
tctaacactc ctgaaagaag gagttgctgc tggctcctta ccagggctat atcttttaca    13980
gagcaggaga cctaaagagg caggaggacc cggacatcgt ttggaaacca agcactaaaa    14040
caggccatct gttataccc caatatcctc tcaggacaag tgttttgaac cactcacaca    14100
aggactagtc tgggcaagtg ggctagatga agaaaccaca aaatagctaa gtggggagag    14160
aaagaccaaa aatactattt tattcaaaat gaaaatacaa tccaaaattc catgattcat    14220
gaagaaatca aatggtatgt gttaggtggt tcttgcattg ctatagagaa atacctgaga    14280
ttgggtaatt tataaagaaa agaagtttaa ttggctcata attctgcagg cttcacagga    14340
agcatggtgc tggcatctgc tcagcttctg gagaggcccc aagaagattt gctcaaggca    14400
gaaggttaag ggagagctgg cacatcacat ggtgagaaag gaagctagag agagagtgca    14460
gggtgaggtg ccacaagtta ccacagccag atctcttgag aactcactta ctttcatgag    14520
gacagcacca agccataagg tgtagggagc caaagtccca tgggacatga ccaactcagc    14580
attccactgg aggctatatg atcaaacagc aaactgttta tcacgaatgc aggatgtgag    14640
caaactcaca actggtcctg ccaacagaag gtttgttgga ggcaatcact ccctggtgcc    14700
tgaggtaatc tactgcaaca tctagagaat gcagtcttgc aagcctactc tggacagggc    14760
agctggcacc ttattccatc ccccttctca ctatctttt ttgcctaata aatacagagg    14820
gctgtgtaaa gctcagggcc cttgtccact agaggcaagt tgcccctga ccccttcttc    14880
caaatatact cttttgtctc ttgtctttta ttctcacatt tgcccccttt gttcagttcc    14940
actaggtccg tgcgggttat atactggtgc cctgagcagc aacagaatca ggctctcaac    15000
aagtgtcatc cgaacatggg actttgagga catgaacgaa gaaggtctgc tggagcagag    15060
gaacagaaat tgacaaggtg aacagggacc ctgggacgag tctgccagca gcggatataa    15120
ggtcagttac ctaaagaggt actgatcagt gccctaaaga gatactggga gcagtgcttt    15180
aaagaagtac tgggaatggg aaattttctg aatcagggta acaagggga gaatttgtct    15240
attaaagaaa aacattatgt gcagttgctt aaagttgtat tggaacagtc tggagcttag    15300
gttaatttgc agacactaac tatcacatgc gtccgtgtga agagagtcca ccaacaggct    15360
```

```
ttgtgtgggc aataaagctt tttaatcacc ttggtgcagg tgggctgagt ccaaaaaagg    15420
agtcagcaaa gggagataga ggtggggcag ttttatagga tttgggtagg tagtggaaag    15480
ttacagttaa aagtggttat ctcttgtggg cagaggcagg ggtcacaagg tgctgggtgg    15540
ggaaatcatg agactctttt tctgggacag gagtgtcaca aggtcaattg atcagttggg    15600
gtggggcagg aacaaatcgc aatggtggaa tgtcatcact taaggcagga actgactatt    15660
tcacttcttt tgtggttctt cagttgtttc gggccatctg gatgtatagt gcagctcaca    15720
ggggatatga tggcttaggt tgggctcaga gacctgacat tcctatcttt ttatattaat    15780
aagaaaaaca aacaaaata gtggttaagt gttggggcag caaaaatttt ttggggtggt    15840
atgtagagat aagggcaat gtttctcagg gctgcttcaa gcacgatcac ggtggtgtgg    15900
gaatctagag tgggagagat taagctgaag aaaaattttg gggaaagggg tgatattctg    15960
gggttgttag aaggagcatt tgtcatatag aatgatgatg gcctggatgt ggttttgtat    16020
gaattgagaa actaaacgga agacacaagg tccaaataag agaaggagaa aaacaggcat    16080
taaaggatta agaattggga ggacacagga catccaatta gagagtgccc aaggggtcc    16140 agtgtaatta tttgcctgga caatgagttt tggggctcta ttaggttgtc ataaccagg    16200 ccagattgat ttaggtaaaa acaacactct tcatttaaaa tatacagagt cctccttttt    16260
tagcagtgag taagttgaga cctattcctg tcttcttata ttaataagta aaataaagca    16320
aaatagaggt gaagtgttgg tgtcatgagg ggaacaggaa gcagttcggt cctatttgca    16380
aattgatttt gggggggtaa agaaaactag tgtacctttg cctgtccaat taataagtag    16440
acacatgtag atggaggagc cacagaggaa gaagagaact ttgtaaggca aaactggaaa    16500
tgtaagggaa aaagatgaga gggagcacca aaagaggtgt cttgcaccca gactcaggga    16560
tctagtgaga gcagcagctg ttagaggttg taatggggat taatgggct actgggtaga    16620 gggggaggtt caacttttat ggtgtatgag aaagcgcata gtgtctacaa gcaacctttc    16680
attgctattc ataggattgg gtataagtaa acaagaaggg gggctagga ggagagtctg    16740 aagaacaagg ggaaggtagc caaggatgga gtgaaatgta gggcaaatgt cttaaaggaa    16800
atgagaggtt ctaagaggag ggctagtggc ttgtaaccca catggaagag gttacgaaag    16860
gatgataaga tggaatgagc ctgtgaggct ggaaggagga ttttccttg gtccaagaac    16920 catttgcctt gtgtgggaag agtttgatag gtggaagttt cagtgggagg gtaggcggga    16980
gtgactgatg agaaggagaa aaactggcca taagggacag aagttggaat gctagctgct    17040
cctttagcta ccttatcagc ataagctttg ccctgagtga tgggatctga tgccttttga    17100
tggcgcttgc agtgaatgac cctagcttcc ttggaagtag agcagcttta agaagagttt    17160
ttatgaagaa ggcattaata atggaggacc ctcgtatagt gaggaaacct ctttcaggcc    17220
atataacaga atggaggtgg agaatatgga aggcatatt agagtcagta taaatactga    17280
cacacaatcc tttttgcaaga gtgagggctc gagttaaggc aatgagttcg gcttgctgag    17340
agggagtgga gtggggcaga gtggtagcct caatgataga tgtgaaagat actatagcgt    17400
agcctgcctt tgctggtgag tggtgattag gcctagtgga actgccatca ataaaccaag    17460
tgtgatcaga gtgaggaaca ggaaagaagg aaatatggga aaatgagtg aatgctaggt    17520 ggatcagaga gatacagtca tggggatcag gtgtggtatc aggaataatg tgggaggcca    17580
gattgaagtc caggccagga acaatggtaa ttgtgggaga ctcaacaaag agtgagttca    17640
actgaaggag ccgggggagg gggagagcgg cagaaagtat atgcatcagg tgtgaggaag    17700
```

```
aaaatacatt ttgaaagtta tgagaactgt agagagtgag ttgatcatag tttgtgattt    17760
tgagggcctt taaaagtatt aaagcagtgg cagctgccac acacagacat gagagccagc    17820
ctaaaacagt aaggtcaatc tgtttagaca gaaaggctgc agggcactgt ccaagctctt    17880
gtgtaaggat tctgaccgca cagccttgta ctttggctgt gtgtaatgaa aagggttggg    17940
atgagttagg gagagctagt gtgggagtag cttctagggc tgtttttaag gaacataaag    18000
aggagtgggg aaaggattta ggatctatgg ggtcagctag gtttccttttt gtgagtttat    18060 gtaatggttt agtcaggatg gcaaaaccag gtatccaaag gtgaaagtac ccaaccatgt    18120
ctaggaagga aaggatttgt tgctttgtag aagggattgg ggtttgggag attagccgga    18180
cacagatcag gagggagagc acttgtattt ttatgaagaa ttatgccgat aggtaacgga    18240
tgaggaagaa atttgggctt tggagggggga tacacgatat tcccttgaga atagatgttg    18300
gaggagcagg agggtgtcct gttgggaaga ttcataggag gggctataaa gtagaaggcc    18360
atcaaaatat tgaataaggt gacaagcaga tggacagaaa agtaaattat gagaaagggc    18420
ttgactgaag taatggaggc tgtccctgaa gccttgtggc agtacagccc aggtaagttg    18480
ctgagactga tgggtgtcag ggtcagtcca agtgtaagtg aagagaggct ggggtgaaga    18540
gtgcaaagga atagtaaaga aagcatcttc aagatccaga acagaataat gggttgtgga    18600
gggaggtatt gaggatagga gagtatatgg gtttggcacc acagagtgga taggcaagac    18660
aatttggttg ataagctgaa gatcctggac aggctttagt cccttcaaag cctgttgtgg    18720
gatgggatac tggcattgag caggataagg gtaattaggt tttaatggga tggtagggtt    18780
gcgtgatcgg tcaccaagga gggagtagag gtatcccata cttgtgggtt aagatagggga    18840 gtcaggaggg gaggttgtga aggaggcttt gaactgggga aaagggtggc aatgaggtgt    18900
ggctgtagcc caggaatagt cagggaagca gataatttag ttaaaatgtc tcaatttaat    18960
aagggagctg ggcaggtggg aataactaaa aaggagtgca taaagaatg ttgtccaagt    19020 tggcaccaga gttggggagt tttaagaggt ttagcagcct gaccatcaat aaccacaaca    19080
gttatggagg caagggaaac aggcccttga aaggaaagta atatggagtg ggtagcctcc    19140
atattgatta agaaagggac agacttaccc tccactgtaa gagttaccca aagtgtctgt    19200
gatgatccag gaggcttctg aggtgatcag gcagtgtcag tcttcagctg ctaagctgag    19260
aagatctggg aaggagtcag tcagagagcc ctgggccaga gttccagggg ctctgggagt    19320
ggctgacggg caagttggac agtccgattt ccaatgcggt cccacacaga tgggatacag    19380
tttaggagga atcctgggct gtaggcattc cttggcccag tggccagatt tctagcactt    19440
gaagcaagat cctggaggaa tgcctgacca cagtggttta ggtgttttga agttcttgtg    19500
tgctggagat gtggctgagg tttttctcac agcagaggca agtaattgca actcagaaat    19560
acattgccac ttggctgtct cttctctatt attgtacacc ttgaaggtga ggttaattaa    19620
gtcctgttgt ggggtttgag ggccataatc taattttga agcttttta atgttgggag    19680 tggattgggt aataaaatgc atattgagag taagacagcc ttctggcccc tctgaaccta    19740
gggcagtaaa atgtctaaga gttgttgcca aagggaccat ggactgggct gcgttttcat    19800
atttgatgaa aaaaaagag cctaaatgct aactaatttg ggagaggtca gataaagtaa    19860
aaggaacatt aatcttgact atgccttcag ctcttgccac ctctctaaga ggaaattgtt    19920
gggcaagtgg aggagtgcta gtcgtggaat gaaaccataa gctggactgg gtgtgaggag    19980
gggaggtgat agaaggatta cagcgtaggg gagtagaggc tgaggaagaa ttgggacctg    20040
gctcagcctg gtgaggagtg gcctggtgag gagcagcctg gggaggagga gagaggttag    20100
```

-continued

```
atgggttcgt agaaaagaag gattcaaagg actcggagct tggtgaggag actgaaggaa   20160
cagacaggag agaaagaaga aagatttggg acaagtcgca ttgggagcag agactaggaa   20220
gggagtgatg tgtaaagaat gcctggacat caggcacctc agaccatttg cccattttat   20280
gacaaaaatt atctaagtct tgtagggtgg agaaatcaaa agtgccattt tctggccatt   20340
tggaacaatt atcgagtttg tattggggcc aaatggtgtt gcagaagaaa ataagatgct   20400
taggttttag gtcaggtgag agttgaagag gttttaggtt ttttagaaca caggctaagg   20460
cagaagaagg aggaatggag ggtggaaggc tgcccataat aaaaaggtaa gtttagagaa   20520
aagagaggat agagacacag agagaggggg tggtggtact catcagccag gggaggtggt   20580
acttgccacc aaggtgatgg atcaaggcag tcatccccac ggtgatcaga cacctctgaa   20640
atgtgggtga ataatcaggc aggtgtccct gcagtgatta gacaccaagg ggagactgtc   20700
ttcccgagtc cgtgaccggt gctggagttt tgagttcaca gataaaacac atctcctctg   20760
tctctaccag aaagggaaag gaactgaaat taaggaaggg agagattgaa gggtggagag   20820
atagcaagag agttggaaaa gagaataaaa agaggccact tactcaattt aaaattggtg   20880
agatgttcct tgggctgatc tgaggaccca aggttgtagg tggatctcct cacggaatga   20940
gggtgaggac aggggactgg tctccagaag gagttcccga gtcctggatc ttcagcacca   21000
aatgtcatgt gcatccatgt gaagagagtc caccaacagg ctttgtgtta tcaataaagc   21060
ttttaatca ccttggtgca ggtgggctga gtctgaaaaa ggagtcagca aagagagata   21120
ggggtgggtc agttttataa gatttgggta ggtagtggaa agttacagtt agaggtggtt   21180
atctcttgag ggcagaggtg ggggtcacaa ggtgctgggt ggggaaatcc tgagacttat   21240
catccaggga aggagtgtca caaggtcgat tgatcagttg gggtggggca ggaacaaatc   21300
gcatggtgga atgtcatcag ttaaggcagg aactcactat ttcacttctt ttgtggttct   21360
tcagtttctt caggccatct ggatgtacac gtgaaggtta cggggatata tgatggctta   21420
gcttgggctc agaggcctga cactaacctc ctgcagaagc cacaaaaggt tattacacat   21480
aaaccatggt ttccacaggc aggcactctt gatgtgaaaa attgggatag agcaggatta   21540
aaacaagctc atcaaaaagg tcttaaagtt gattcttcag ttttctccac ttggagttta   21600
gttcatactg tacttctgcc attatctcct tattattctg cggaacagca ggctgaatct   21660
aaaaattgga agaatttgt tgtcctactc acagctccaa ttgaatataa aaaacaggag   21720
agggaggata aaaattggcc tataccgcct cctccagatg cagaaacatc tgtaccatct   21780
ccttcagtgg cagaaataga gatcccagta caaagaattt tatgctctgc tgtcatagct   21840
ggagagccct taggaccttg tgcttttcct atttctgtaa ggcctgatcc aaataatcca   21900
cagcagttta ttcatgaaca ctctccacta gaatttaagt tgttgaagga attaaaaact   21960
agtgtggtca ataatggagt acaaagccaa tggttcctgg aggaaggaat gctagacata   22020
gaactttggg agcaagtggg gagaaatctt aaacaacacc aggcacaaag gcatcaggtc   22080
ccagtaaaat ctttatgtt aggggcttg agtagagcag ccctggttgt tacacacaaa   22140
agagcctaaa aagggaaagg aggaggaaat gtcacctgcc ttatcacctc cccttccctc   22200
agtgccaata tcactgggcc aaaataacaa agaggaaatg gaggtcttac ctaagcttcc   22260
tcctccaata gataggaaga aggacagagg atacgctaca gctatcagtc cctgtcttaa   22320
gcaggcagca ttagaaggag agctcttagc cgggtgcagt ggctcatgcc tataatccca   22380
gcactttggg aggccgaggc aggcagatca tgaggtcagg agatccagac catcctagct   22440
```

```
aacatggtga aacccegtct ccactaaaaa tacaaaaaat tagccaggca tgttggtggg   22500
cacctgtagc cccagctact tgggaggctg aggcaggaga atggcatgaa cccaggaggt   22560
ggagcttgga gctttcagtg acctgagatt gcaccactgc actacagcct gggcaacaga   22620
gcaagactcc atctaaaaaa agaagaagaa ggagagctct taacctgctc agtaatgcaa   22680
aatcggcaag gcaatcaggt gtatgtttat aaaagataa  gaaaaaggca ttagaagcca   22740
aaaccacgtg gccaagcagg cagtgggcag gagaaaatgc tcagaggcag aaaagctcac   22800
agcgacaaag ccaacaaggt ctgcccagga cggcagcatc cctctggcaa aggagcaagg   22860
gagcagcaca gacacaggca aagcctaaac aagtacaatg tggccacctc ccaggacctg   22920
caccactgcc ctctggctct gtgggcagcc cattgcaaaa tttcatgtgt tacatctcag   22980
gctatgattc tctgctaaga tgtaagtaaa atgtaagaat ttgaaaagca tcttttctaa   23040
taatggccac tattgtcatc tctctcctat ccctgatgta gctttccaaa ttcaatttaa   23100 gtaaacagt  aacctttgaa gggaagagaa ttacagaggg cccatgaatt agttgaagag   23160
taattaaaag ctaggcatgt aaaaccacac attacgcttt aaagaagaaa tttaaaccta   23220
attaaatgat atttgttaaa ttagaaggta aaaatgttgt gccctgttgg gaacaggccc   23280
ccaaatctgg ccataaactg gccccaaaac aggccataaa caaaatctct gcagcaccat   23340
gacatgtttg tgatggccat gatgcccacc ttgaaggttg ttggtttact ggaatgaggg   23400
caaggaacac ctggcccacc cagggcagaa aattccttaa aggcattccc aaaccactaa   23460
tgatagcatg agcaatctgt gccttaagga catgttcctg ctgcagacag ctagccgag   23520 cccatccctt tgttttggcc catcccttg  tttcccataa ggaatgcttt cagttaatct   23580
atgatctata gaaacgatgc ttatcactgg cttgctgtca ataaatatgg gagtaaaact   23640
ctgttcaggg ctttcagctc agaaagccat aagcccctg  atttcccact tcccacccct   23700
tatttctgtg tgtgtgtctt gaattcctct agcgcctctg ggttatggtc tccacaacca   23760
cgctggtctt ggcagtgccc ttctcagaaa gtgaaaaaga gttgtatgta agtgtagtga   23820
aaacataagc atgaatcact gtcttaaccc actgattaga tagtctttga tttgtacttg   23880
ctaaaagagt cctaaattga gttcctcagc tagtgagtca ctgttttcaa gactgtttgc   23940
cagattgaag tccataaact tggtcagccc gaaaactcaa ttacaagatc taagctattc   24000
tgcctgtggc tttaagcaca tggttaaagt atattattta agtctctcct tctagatatg   24060
ctttcagatt ttcttttaa  acttcttgtt acttatttca gctttccata ttgataatta   24120
atgcagtcaa ttgctcagtt atgactgtga tatcatcagg attcctttaa gtaaaaggca   24180
attcaaagcg gtattgcact cccccatacc taatgcttta acactgttta ctgatgggtc   24240
tggtaaacat ggaaaagctg cagtctagta gagaccacat aattcaatca ctcgatctga   24300
gttcactagc actcagagag ctaaggttac tctgtttatt tattaaagaa ttttacaac   24360 cttaagctca ctctggactt tccagcctta tgtggcaaat gtagccatca atttatggg   24420 tcaagactta cttacagcat gggatatgag gcttacaaat gagactttga tacccagga   24480 ttttaaatgt tgaagaacac gggatatcag agtgaaaaag gttagggaa  aattctgaca   24540 agggaaaatt ctaacctgat atcaataact ggaaagacag gttaaaccct gcaaggggat   24600
acattgacat ttttcttcc  tcacttgctc ttttctgctg tctgaatatg ggcatgaggg   24660
caagagtcat tttagaccac caagtgacct tgaggataga agccttatac tagaggtggt   24720 gggaagaaa  aaacagaagg actcataaag aaaaaaataa taaacctcag tattaagatg   24780
gaaaaattcc cccaattggt ctataggttg aacttcatct ctattaaatt tcagctatgt   24840
```

```
tttttgcagaa tttgatatgc tgatcataaa atttatatga aaatgcaaga gacacagaat   24900
agtcaaaact ttgaaaagaa gaaagttgga ggacttacac ttgttgattt taaggctttt   24960
tacaaagcta taataatcaa gacaatgtgt tactgacata atgatagaca tattgatcaa   25020
tatagacaat ggatgaatgg agtagaattg acagtctaga aataaaacct tatatatatg   25080
gtcaatttat ttctttatgt attctgtcat ccagaataca taaagaacac cttcaactca   25140
ataacaacaa taccaacaag ggtgccaaga ccaatcaatg gaggaaataa tagtcttttc   25200
aagaaatttt gctgagacaa ctaagtattt atatgcaaaa taatgagttt gaatggctac   25260
catatacaaa aattaactca aatggactat attaggtcag tgcaacagta attgcagttt   25320
accaccatta cttgttttt ttttttggtt ttttttttg agacagagtc ttgctctgtc   25380
acccagacca gagtgcagtg gcatgatctc agctcactgc aagctccact tcctgagttc   25440
acgccattct ccttcctcag cctcctgagt agctgggact acaggcatct gggtaatttt   25500
tttgtatttt tagtggagat ggagtttcac catgttagcc aggatggtct caatctcttg   25560
acctcgtgat ctgcccacct cagcctccca aagtgctggg attacaggca tgagccacca   25620
cgcctggcct accattactt ttaatggcaa aaatgcagtt acttttgcac caccctaata   25680
gaactaaatg taagagctaa aactacaaaa ctgttagaag aaagcatagg agcaaatctt   25740
aatgacatga gagttggcaa ttgttttta gatatgacac caaaagcatc aaggacaaaa   25800
gaaaaaaatg gataaattgg acttcctcca aattaagaga acttttgtcc tgcaagcaat   25860
actattaaga aagtgaaaag acaagtcaca aaatgggaga acattttttgc acataatata   25920 tttaataata ggctgacatc cagaatacat aaataccttac aactcaatac caaaaagaca   25980
gcccaattta aaaatgggcc aaggatatga ataaacattt ctctaaagaa gatacaaaaa   26040
tggtcaatat gcacatgaaa agatgctcaa tatcaatatc tattaggaaa atacaaaatta   26100 aaacacaaaa tataaaacac aagatatcaa tttacactca ccaggatggc tgttatcaaa   26160
aagacagata acaagtattg gcaaggattt ggggaaattg taaccttcat acattgctgg   26220
taggaatata aaatttgcag caggttttgga aaacagttta gcagtttctc aaaaagcctg   26280
ggcatggtgg ctcatgccta caatcccagt gctttaggga gctgaggtga gaggattgct   26340
tgagcccagg agttggagac cagcctgagt aacacagtga gacctctttt ctaccaaaaa   26400
gaagagagtt aaacataggg taccatataa gccagcaatc catctcctag atatgtaccc   26460
aagaaagttg aaaacatata ctgacacaaa aacttacata tgaatcttca tattagcctt   26520
ataataatag ccaaaaagta gaaacaaccc aaatacccat caactaatta aaatatggtg   26580
tatctataca tattatttgg ccataaaagg aagtactgat acatgtcata acacaaatga   26640
accttggaag cactatgatc tctgtattag tcagctcttg tattgctata aagaactacc   26700
tgagactggg taacttataa agaaaaaggc ttaattgagt cacagttcca caggctgcac   26760
agggatcatg gcccaggaga cctcaggaaa cacagttatg atggaaggaa gagagtgaag   26820
gaggaggtgc tacatacttt taaaccacca gatcttgtga gaagtcactc actatcatga   26880
gaacagcaag ggagaagtcc acccccatga tccagtcagc cccagccagg ccccaactcc   26940
aatattgggg attacaattc cacatgagat ttgggtgggg acactaatcc aaacaatatc   27000
attctgcccc agcccctccc aaatcctgtg tccttctcac attggaagat acaatcatcc   27060
cttctcaaca gtttcatttc agtattaact caaaaatcca aagtctcatc tgagacaaga   27120 caagtcccctt ccacctatga gcctataaga tcaaaaagaa gttagttact tccaagatac   27180
```

```
aatggaggta caggcattgg gcaaatatat ccattccaaa agggaaaaat tagccaaaac    27240
aaagggccca caggccccac gcaagtccaa aatcaagcag ggaaatcatt aaatcttaaa    27300
gcttcaaaat gatatccttt gactccatgt ctcacatcca ggccacacca atgcaaggag    27360
tgtgctccca aggccttggg cagctctacc ctgttgctct acagggtata gcccccatgg    27420 ctgcttttcac aggctggcat tgagtgcctc cagcttttcc aggtacacag tgcaagctgt    27480
tagtggatct accattctag ggtctggaag attgtggccc tcttctcata gctccagtag    27540
acagtgcccc agtggggaat ctgtatgggg gctgcaaccc cacatttctc ctctgcactg    27600
cccaatagag gttctccatg agggctccat tcctgtagca tacttctacc tggacatcca    27660
ggtgttttca tacatcctct aaaatctagg taggggctcc caagccttaa ctcttgccct    27720
ctgcacatcc gcaggcttaa taccacatgg aaaccaccaa tgcttatggc ttgcacccta    27780
tgaagcagta gtctgagaca tatctgggcc ttttggcca tggctgggat gcagggaaca    27840
gtgtcctgaa gtggcacagg gcagcgggc catgggcctg gcccatgaaa ccttctttcc    27900
tcctaggcct ccagacctgt gatgggaggg tctgcctcga cggtctctag aatgtgtttg    27960
aggcatattc ctcattgtct tggctattaa tatttggctc ctctttactt atgcaaattt    28020
ctacagcctg attaattcct ttccaaaaaa atggggtttt cttttctact acatggtcag    28080
gtcacaaatt ttccaaactt ttacgcttcc ctttgaaatg taagttccag ttgcaggtca    28140
tttctttgat cacaaatata agcatatatt tgtagaatca gccaggccac atcttgaatg    28200
ttttgctgct tagaaactgc ttccaccaga taccctaaat cattgctatc aggttcaaaa    28260
ttctacatat ctcagggca agggcacaat gcctccaaga cctttgctaa tgcataagaa    28320
aattgacctt tgctccagtt cccaataagt tccccatctt catctgaggt ctccttagcc    28380
tggacttcat tgtccatatc agtatcagca ttttcatcac aataatttaa ctagtctcta    28440
agaagttcca aactttccct tatcttccta tcttcttctg agccctccaa actgctccaa    28500
cctctgccca ttacccgggt tccaaagctg cttccacatt ttcggtatct ttatagcaat    28560
gctccattcc tgataccaat tttctgtatt agtctcttct cgcactcctg taaagaacta    28620
cctgagactg ggtaatttat aaagaaaaga ggtttaattg actcacagtt ccacaagctg    28680
tataggaagc atggttcaga aggccacagg aaacttacaa tcatggagga aggcgaagag    28740
aaagaaggca cgtcttacgt ggctggagta ggaggaagag agtgaagggg gaggtgttac    28800
acacttttaa acaaccagat cttgtgagaa ctcactcact atcatgagaa cagcaaggga    28860
gaggtctgcc tccatgatcc aatcacctcc taccaggctc ctcctccaac attgggatt    28920 atgatttgac atgagatttg ggtagggaca caactccaaa ccatatcaat cccatttata    28980
tgaaatgtcc acaatagata aatctataga gacataaaat agattggtgc ttgcctagtg    29040
ctggacgtga caggagggtg tgagtaaaag aggcaatgga gtgataggta cagggtttct    29100
ttttggggtg atgaaaatat tataaaatta gattgtggtt atagttgtat aactcttgaa    29160
tatcctaaaa atatattgaa ttttccattt ccatttttaaa tgggtgaatc ttatggtatg    29220
tgaattatat ctcaataaaa ctgcaaaaaa tgcacaattt gcaattgcaa aaatatggaa    29280
ccagtccaaa tgcccatcaa tgagtggata aaggaactgt ggtatatata tatatatata    29340
tatatatata tatatatata tatatatata tatataca cacacacaca caccatgaa    29400 tactactcag ccataaaagg gaataaaaca atggcattct cagcaacctg gatggaattg    29460
gagaccatta ttcttaagtga aataactcag taatggaaaa ccgaatatca tacattctca    29520
ctcataagtg ggagctaagc tatgaggatg caaaggcata agaatgatat aatggacttt    29580
```

```
gggaactcag ggaaagggtg agagagggt gaggaataaa aggctaccca ttgggtacag   29640
tgtacactgt tcaagtgatg gctgcaccaa aatctcagaa atcaccacta aagaacttat   29700
ttacataacc aaataccacc tgtttctcaa aaacctattg aaattaatta attttaaaa   29760 actgctgaaa tcaatagtga aaggatggac tattcaataa tgacacagtt aattgaatat   29820
catattttaa aaattagatc cttacctcac actataacat aacaataaat tccaggtgaa   29880
ttatagacca aatatgaaaa gcaaaatttt aatattttag aagacaattt ttatgacctt   29940
aagttagaaa atgatttta aaaacaggat gcaaaaacac taatcataaa gagatatttt   30000
aggccaagca tggtggctca cacctgtaat cctagtactt tgggaagctg aggcaggtgg   30060
atcacttgag gtcaggagtt caagacaagc ctggccaata gggtgaaaca tgtctctact   30120
aaaaatacaa aaattagctg gaaatcgctc gaacccagga ggcagaggtt gcagtgagct   30180
gagattgtgc cactgcactc cagcctgggt gacagagaga gactccacct caaaaaaata   30240
aataaataaa aataaagaga gatttttaata aggtgcatta aaataaaaaa ctatccatca   30300
aagacaccat gaataagtt aaaataggcc acaatgagaa tatatttgcc atgaatttt   30360 tcttttttt tgagatggag tcttgctctg tcacccaggc tggagtgcag tggtgcaatc   30420
tcggcttact gcaaacttca cctcccaggt tcaagcaatt ctcctgcctc agcctcctga   30480
gtagctggga ttacaggtgt gtgccaccat gcctggctaa tttttgtatt ttttgtagac   30540
acggggtttc accatgttgg tcaggctgag ctcaaacccc tgacctcgtg atccaccttc   30600
ctcagcctcc caaagtgctg ggattacagg catgagccac cgtgcctggc ctaccatgaa   30660 tatttttta aaggtagcat ccagaattaa taatcttctc caacaaattt cattagtagt   30720
cagggaactg caaattaaaa tcaaagtaaa atactacttt ccactcatta gactaaaatc   30780
cattcaagtc tgataatacc tagtactgag ttggagtaat agaaactgct aatgggacag   30840
ttagttggtc atcactttgg agagaaatta gtcagtatct agtaaaagtt agtgatacac   30900
cttccatttt catctgttct gtgctgctac caaagaatac ctgagactag gtaatttata   30960
aataatagaa atgtatttct aatggttcta gaggctgaga agtccaagat tgaagggcca   31020
gcctctgcag agagccttct tgctgtgtca tgccatggca gaaagggcaaa gagagggcaa   31080 gagagagcaa aagcaaattc acagcatcaa tccctttat aatcagcatt actctattaa   31140
tgagggcaag accctcatgg cctaatcacc tctaaaaggt cacacctctt aatactattg   31200
caatggtaat taagtttcta atacatactt tttgggagac attttcaaac tatagcacct   31260
accctatagc ccaacatttc tactcctagg agtatgccct agagaaattc tgcataaata   31320
tctaaagaga ggccattgtt gcattgttag gtactggaaa attggaatca attactatgt   31380
ctaccagcag cagaagatgg ctttttaaaa gttttggttt attcatgaaa tggaatattg   31440
cataaagtat gctccatctc accagatgaa aacatttttc actaggacta tttcaaaagt   31500
agtcttatca ctgggcttct ctattatgca taaaaatttt aagtgaacat gttctttgac   31560
ctagtactcc tacttttagg aatttgccca aaagggacaa ttatactact gggataaatc   31620
tttgaatcat aaagtaagtt gtaaatggta caagcagtat gtcttatttt tatttaaagc   31680
acattaacaa tattcacat atagtaaaaa ataaataaat aaaacatgtg aataataaac   31740 acccaatta gaacaagtgt tgacagtgga gagggaaaga gagagaaaga aggagaaatg   31800
gggagtggga gcgggtacac aaggaaattt tagttgcagc tccaaatttt tacttttac   31860 acaatgaagc gaatatggca aaataagatt tgttaaagtt gggcagcagg tacacagata   31920
```

```
ttctatcatt atcctttgaa tatttctgta gatttaagtt gtccattaaa aaaataaaat   31980
acacacataa ttttttaagat tagttttttc tatttcctgg ccttcgcatg cactgttaac   32040
tttacctgga attctttatg cagtaattaa gagcaaaggt gtagagcaag actgcttgag   32100
cttggatccc agcactgagt tgatttaggg agaataactt aatctcttaa tcccaagaga   32160
aaatatgata taatagtttt gagctcataa agttttcata agcattaaat gtgacctata   32220
tatgtaaagc aatctaacag tgcctatagt atttataagt gtctgcatta ccaaattcat   32280
cattatcatg gcatgtcatg tcaccatcca ctacattacc atcactgtca ccatcatcat   32340
catcaccacc accatcatca ttaactccct tgtctagtc aattcatatt tgttcttcgt   32400
attttagata cctgttaaaa tattttttca aagatgtcta ctctgattct tcagtacaaa   32460
tttgatttaa taagatccta tcattttgtc caaatactta taaaaatttg tagttctata   32520
tttaatgtgt tttgtttgtt taacatctct ctcctacatt gtgttaagtt ttttaaagag   32580
aaggtaaggg ttaaagagag acatagagag agaaagagag acagagagag agagagagcg   32640
gttctacagc aatacaggta tattagaaaa acctgcaaag gtggggacca gcttaatgcc   32700
agagcccccc actgcttata ggctggggta cttataggtc tgggggtact ataggcctg    32760 ggtgggtggg gtctgagcag tatggcttgc tgcccaagaa gatgttgata agacgttccc   32820
atgatgaggc agtttggtcc ttgcttccat agagtgtgat gcttcttgca cttttttccca  32880 gcagaatgtg gtagggatgt tccttcaggt gggcctttgc ctggcagggt atgataagga   32940
tgttcctgtg ccttggaatc aggtagttag acaggatgtt tctcacagcc tgaaccccca   33000
tggaatgttt cactttgacc agggtctgcg aaatagcagg gggcttacaa aatggtgtag   33060
tttggactaa caccttggaa cacaaaagtt tcttggggcc aaggctggcg tattagtctg   33120
ttttcatgct gctagtaaag acatacctga gactgggtaa tttataaaga gaaagaggt    33180 ttaatggact cacaattcca catggctgga ggcctcacaa tcatgaggga ggcaaaggag   33240
gagcaaaggc acgtcttaca tggtggtagg caagagaacg tgtgcagggg aactgccctt   33300
tataaaacca tcagatcttg tgatacttat tcactatcaa aagaacagca cgggaaaaat   33360
ctgcctccat gattcaatta cctcccacca gattcctccc atgacatgtg gtaattatgg   33420
gaactacaat tcaagatgaa atttgggtgg ggacacagtc aaaccatatc agctgggtat   33480
gttttattca cctttttata cccattgtca tgtcttctgg acaaacaatg gatgtaaaat   33540
ggtatagact cctgagtact catttgttga atgacaaatc tatgaaccat ttgaccagta   33600
tgcagcagcc attaaaatta tgtttatgaa taatttacag catggaaaaa tttgggggttg  33660 ctagtagaaa aacaaaaagg tacaaaagga tatatataat aagcctacaa tgccatataa   33720
acaatactaa cagcaaaaac aaacctataa attgggggaa gatgggcag atagaagtaa    33780 cctaaaatac taacatgttg ttttgggggtc atgaaattat aaatgattat gcacccctta   33840 attttttactt tctatgtttg attttttctat ggtaaatgca ttttttattga ggtggaattc   33900 acataacatg aaatgaaaaa tttagtggca tttattatat tcacaatatt gtacaaccac   33960
tagctctact tccaaaacat tttcatcact ccaaaataaa accttgtacc cattaagcag   34020
ttactcccca ttatttcctc tcttagctcc tagcaaccac caacctgctt tctgtctcta   34080
gggatttatt tattctggat attccataaa aatggaggca caatatgtac cttttatgtc   34140
tggcttcttt caccaagcat gttttttgagg ctaatccaca ttgcagcatg tatcagtact   34200
tcatttcttt ttatgaataa ctgtatacag accacaattt gttatccatt ttttggttta   34260
tggacatttg ggttgtttcc atctctcaac tattgtgaat agtgctgcta tgtatatttg   34320
```

```
tgtacaagaa tttggttacc tattttcaat tcttttatgt atatatctaa gatgaaattg   34380
cagggttata tgctaatcct atgtttagca tttttttta ggaaccatta aactgttttc   34440
caaatctgat gccccatttt atattcctac tagcaatgta agcaagttcc aatttctcca   34500
tatcctcaac aacacttgtt attttctatt tttgttatag ccattctaat gagtgtaaag   34560
tgatatatca ttgtggtttt ctttgcattt tccttatgaa cattgatgtt gagtaccttt   34620
tcatgtactt tttggtcatt tatatatcat ctttggagaa atgcctcttc gtgtatgttt   34680
tgcccatttt aaaactagat tgtctttgtt gttgacatgc atgcattctt taaatattct   34740
gcatactagg cccttatcag atatatgatt tgcaaatgtt ttttctcatt ttactggctg   34800
tcttttcact ttattgataa tgtcctttga tgcccaaaag ttgtttattt tgatgaagca   34860
tatttatcaa tttatttctt ttattgctca tgcttttgat gtcacctcta agaatttata   34920
accaaatcag aggtaatgaa ggtttacccc tctattttct tctaagagtt ttatagtttt   34980
gactcattta cttaggtcgc tgattcattt ttagttaatt tttgcatatg atgtgaggaa   35040
gaggtccaac tttactcatt tgcatgtgga tattcagctg tgccagcacc atttgtgaag   35100
agtctatcat ctcctcattt aataatagta ttgacacctt tgttgaaagt caattgataa   35160
taaatgtatg agtttatttc tggaatctaa attctattcc attgatctac atgtctatcc   35220
ttgtatcagt atcacactat cttgattact gtagatttgt agtaagtttt gaaactagaa   35280
agtgtgagta ctgcaatatt cttcttttc ttttttaaag attgtcaggg cctcttgcaa   35340
tttaataggg atatgaggat tgacttttct attctacaaa attaaaattt tgttagagat   35400
tgcattgaca ctgtaggtag ctttcagtaa cattgccatc tcaacaattt taagtattct   35460
aatacatgaa tatgagcttt ctttctcttt atttaggtct tctttaattt ctttcagcag   35520
tgttttgtag ttttggggta caagtctttc acctttaaat tttggtgaaa tttattccta   35580
ggtattgcat tttttatgc tattgtaaat aaaattattt tctcaatttc ctgttggatg   35640
ttcattgcag gtgtatagaa actcaactga ttctttgtgt tgatcttatg ctgagaccag   35700
ctcagttggg gagaccctaa cctagaagca ctagaggaat taaagacaca aacacagaaa   35760
tatagaggtg taaagtggga aatcaggcgt ctcacagcct tcagagctga gagcttcaaa   35820
cagagattta cccacatatt tattaacagc aagccagtca ttagcattgt ttctatagat   35880
attagattaa ctaaaagtat cccttatggg aaacgaaggg aagggctgaa ataaagggat   35940
gggttgggct agttatctgc agcaggagca tgtccttaag tcatagatca ctcatgctat   36000
tgtttgtggt ttaagaatgc ctttaagcgg ttttctgccc tgtgtgggac aggtgttcct   36060
tgccctcatt ccggtaagcc cacaaccttc cagcgtgggc attatggcca tcatgaacat   36120
gtcacggtgc tgcagcggtt tttatggcca gttttggggc cagtttatgg ccagattttg   36180
gggggcctgt tcccaacaat cttataccct gcaattttgc tgaatttgct tgttaacttt   36240
gatagttttt ttgaggatta tttgggattt tctacatatc atgtcatctg tgaataaaga   36300
tagttttgct tctttctttc tcatttggat gcctttatt tccttttctt gcctaatttc   36360
cctggctaga acttccagta tgatgttgaa taaccatggt gaaatgggca ttcttgtctt   36420
tttcctgatg ttagagagaa attttcagt ctttaaccat tgagtataat gttagctgtg   36480
ggttttttac aaatatcttt tatcatgttg aggaagttcc ttcctactcc tacttcttgg   36540
agtgtttttg atataaaggg tatttaattt gtcaaatgct ttttctgtgt cagttgagat   36600
tatcatgtga gatttttttt ccttcattct attagtgttg atgttacatt ggttgatttt   36660
```

```
ttatgttgta ctacatttgc attctttata taaatttcac ttggtcatgg tgtataaccc   36720
ttttaatatg ccattggatt tagtttgcta gtattttgtt tagagttttt gcatctatat   36780
tcataagcaa tatcagtcca caggttttt gtggtttatt tgtctggctt tgctataatg   36840
gtaatgctgt cttcttagaa tgaatgaggg agtgttttct cctctttcat tttttaaacg   36900
tttgagaagg agtgatatta attttcttt aaatgtttgg tagaacttac cagtgaagcc   36960
gtctggttct taacattttt ctgtgttggg aggtttctga ttaccaattt gatctcttta   37020
atttttacag atcttttcag attttctatt tcttcttgag taacttttta gcaatttatg   37080
tattttagaa atttgttcat ttaatctagg ttatttaatt tattggtgtg cattttttca   37140
tagtattatc ttataatctt ttaattttg taaagttgat aatgtcccca ccttacctga   37200
tcttagttat ttgtgtcttc tctgtattct ttttgtcttc ttcttctgtc ttagcatagc   37260
taaaggtttg tcaactttgt tgatctttta aagagtcaac ttttgctttc agcatgcatt   37320
acttttaaa tagaaatata tacacctaag ttgcattaca aaggagttgt cctccacaca   37380
cttattcttt cccaccatca gaggtttatg gtccccgcaa aagtcaccat cagttgggct   37440
caactccaat cagtcatggt aggtcagggt ccatctcatt gtctccatca ctcatgccca   37500
cccagggtaa gtctaatcat gttcaccaat cagaacctct gccacatcag ctctgtgggt   37560
ttcctctcat gccatctgta ccaacaatga gcacagtctg ggtttcctga tgttttctat   37620
agcatggtgc ccctccctgg gacacctcag aagccacaat gatattcatt aaacttcttc   37680
ctgcaagtac tccctctatt gctccttcta ctcaccaagc ttagtgtcag ggaatatgct   37740
ggtggggagt atgaatctta gcttctcact cccagactcg gctcccaacc tgctgttgcc   37800
aagtcttggg gacatctata aatgccttct aaatacctgt cttggcctat ccccagccac   37860
agattcctcc ctagagcagg ctacctctga ggcatctata ctgagatctt aatcacagag   37920
acatttaaaa catctaggct acaaaagaat tcctactata gggttcaaat gaatttcttt   37980
ccgtcacttg agacagcttt ttagcaagta catgtattaa agattctgat ttcccctttt   38040
ttctcctaca gtttgtttgg cctaaaggta tgacatctaa tctgctgcat ttacactcta   38100
agtcaaaatt accatttgt tctttaatt tctatttcta atcatacatt cttgtctact   38160
cctggttcat ctggagacaa agttgaactt agaagatgga ggagaaattc ttatctgccc   38220
tctgctagtt gacacttcct ttccaagaat catttgcagt tgctgggctt tcttgctgtg   38280
actctatgcc ctgttgtgtt acttttcat ttgtgacaaa aacagtggta atagtttgct   38340
tcattttat tatgaagact tgaccaggat aggtaggaac ataattactg cttttctgt   38400
gggcatcata ttggtccaga tcatgtttaa ccagaattga agatgtaaaa tcctagaact   38460
cactaatcta ttttagtagg tcacaggaag catgcaaacc ataaaaaccg caatgaacca   38520
aaagcatctg tgttgacaag aggcaagaat ttctctattt tctaaaggca ctaactgaac   38580
aaatctattg cccattactt aggaaattgc taagggcatc gttaaagtac ttcaggctgt   38640
tgaaaaacct tttctgtctt cttgccccac caccaattct ctctagctat gctttctctc   38700
acatgttctt gccatccatg gagtggcaga gaggttctga gtacaactct aactttcagt   38760
ttcaatggcc taatccccaa ctcaactgct gaccttgagt gtaaaaataa acaagatctt   38820
aaacatctta gggccagcat tctgggtctt cttttgttat tgggagca taaactattc   38880
tcatatcatt ggcttgcaga aaaattgagc ttctcctctt ccttgcccca tgtcaccttg   38940
aggtgaccac agccctgcct tctatgtaat cctgcttggt cagcaggcac atcagagctc   39000
agtggcttgt gacatacttt ccttcaagcc tgctcgaagg gccatactca tcattgagac   39060
```

```
tgggaacctt agaaaccatg aacccagtgc caatgggtag atacagaatt ctcaaactca   39120
tgaaaaaaca tccttttttaa ctctctccgt gtgcataaag aattctaaga tgtactgatc   39180
aagattccca attttctaac tatctattaa tatatggacg aggtaagaag aaagttgcaa   39240
gaaaaaaatt tgtttgactt gacggttgtg tggttatttg ccacactccc ccagatccac   39300
tctgagtccc aggatgctga ttttaggggc tacattgcct agactgtcca ttattccctc   39360
ttcccatctg gttcagtcac tgggaagcac tggtaggagg tcagagtggg agaaggaggt   39420
taggatactt tctgcccctg ctgtcctact gctttgctga acttctagca gtggctgagc   39480
catcaacctg cagctctcaa ttccagctgt ctgtagcact caagtggtat tgtttattct   39540
tttgatcctt ctagctgtta aggaagaaaa aaataatttt ttcctcaatg ctcataagtt   39600
cttggaatgg acccctgtaa caaaagacag attaacacga gaaagttta ttaacgtaca   39660 tattttatac gtacatagga gctatccagg gaatgaataa ttcttaaaaa ggtgactttg   39720
aattccagct catatagcat cttcaacaaa gttcagtaac attttagaga tatgacaaga   39780
caaagaaaat gaactttgag cctctaggga cagtgacttg taggaaggca aaaggaataa   39840
atggaggtaa aggctggtta gtaatacttg ttaatgaaga ttcctctggt gccatctcca   39900
ggtccacaag gatttaaatt tgtcttcagt ggtgaacctt tgttcaccct ggcagaaggt   39960 gtggagggg gtgcagatcc gttttgtctt tgtaagtcta tatcctgctt ttagacaaat   40020
aaagggaggg aaaagagctt tccttcatct gcttcttaat tgccttcagc tcaacaatcc   40080
ttatgcaaaa gaggtacatt ttagggtgtc aaattctggt ctcccacaaa gcatagggat   40140
gacagaccac ctcaccatcc ctgttgcttc ttttaagcct gctcacccct ccaaaaatat   40200
tttcattcta tactgtctct tcaaaatctc agcggagggt gccctctgtt atcctgccct   40260
ctgtgtcagt ataagccaaa ggtttgaatc ctggctctgc aactatctac ctctgtgcct   40320
ctccttgttt atgaaattac agggctggag acaaagatca caatgtgaag acaaaattgg   40380
agagcggtcc taatcagcca gagcaaaatt tctggctctt gctcttcccc atcctgggtt   40440
gaatcatagg aacaggtggc aagatgccag ggtcaggaga ttccagaagt ggcagcaagc   40500
tcagtgttac caggtcaggg atgacctgtc ttattattga aatctcagag atatgctcca   40560
attccggccc agagacacat tgagagacaa ctggggaact tgctatgttc ctgaacaggc   40620
aatgagctgt cttccaagaa aaaacctgag acccttcaag tctcaggtct tacttagcac   40680
atataccagg tcttacacag gacacatggt tacaactgac tgaaatctgg gctgggtgta   40740
ggagctcaca cctgtaatcc cagcccttca ggaggctgag gcaggcagat tgcctgagcc   40800
caggagttcg agaccagccc gggcaacatg acaaaacccc atctctacaa aaaatagtca   40860
ggcatggtgg catgcacctg tagtctcagc tacttgggag gctgagatga gaggattgct   40920
tgaggttgag actgcagtga agcatgatca tgccaccgca ctccagccta ggcaacagag   40980
caagatcttg tcgcaaaaga aagcaaaaac acaacataac acaacaacaa caacaacaac   41040
aacaacagca aaaagccaa cttcttgaaa tctggaaagg acacctggac tgccctgagc   41100
atttgattgt tgttggctct agcagtggat gcatccttca acctctggca ctctgcaggg   41160 ctcgactgt tctgttctgt ttgttacctg tggagtgcct gccagaccct gctctagctg   41220
ctttaggtcc atttacccctc atagaccccc agtcttgtta ttcatatttc atatttggga   41280
aatggaaact tagaaacttg ccaagtccac agcatgagat cctgcctccg gtgtctgctg   41340
gattccagaa agtgccaggg gccaacttag atgacaccat gttctctgca caatcttagg   41400
```

```
aatgctccta gtctgatgtc cccattgcaa aatttacatt atcttttaac aaaacgtctt    41460
tccaaggagg ggcatttaaa ataactgagg ttcttcttgc taaggacgtt cctgacacaa    41520
gagataattt agcatttcct tttcattaaa aagtttgaaa tcctgtaatt tgtgataatg    41580
tggatgaacc tagaggatgt taagtgaaat aagccacaca cagatagaca aataccacgt    41640
gatctcactc ttatgtggaa tttttttta aataagttgc ttagccgggc atgatggcac     41700
acacctgtaa tcctagctac tcaggaggct gaggtgggag gatggcttga actcagaagg    41760
tggaggtagc agtgagctga gactgtgcca gtgcactccg gtctgggtga cagaatgaaa    41820
cccaatttaa aaaaaaaaa aagttgcta tcttagaaaa agacagtaga gcagtggtta      41880
ccagagactg gggaggaaag agaggaggtg agaatgggca gcagttgatc aacgggtaca    41940
aagttaccat gagataggag aaacaagtgc tggtgctctg ctccaagtag ggtgacggta    42000
gttaataatg aattctgtat atataaatag ctagaagaga gggttttcaa tatcattatt    42060
atttcaaaag aaatgataaa tgtttcagag gatggatatg taattaccct gatttgatca    42120
ttgcacaatg tatacatgta gcaaaacatc acattgtgtc ccataaatat atacaattat    42180
tatgtgaatt aaataaaaaa aaattttaaa gtcttatcta aatgaaattt ctaaccagat    42240
tctgaatcca tgataccact gaaaccagca cacatgatcg cagtaaaacc tcattatact    42300
tcctccacta tcaccaatac cctttattct ctggaacatg aaacattctg ttgtgctcat    42360
atcatgcaaa ttatcactag taggagagca gagagtggaa atgttccagg tataaagacc    42420
cacaagataa agaagctcag agtcgttaga aacaggagca gatgtacagg gtttgcctga    42480
ctcacactca aggttgcata agcaagattt caaaattaat cctattctgg agacctcaac    42540
ccaatgtaca atgttcctga ctggaaaaga agaactatat ttttctgatt ttttttttca    42600
aatctttacc attagttgcc ctgtatctcc gccttcactt tctgcaggaa actttatttc    42660
ctacttctgc atgccaagtt tctacctcta gatctgtttg gttcagttgc tgagaagcct    42720
gacataccag gactgcctga gacaagccac aagctggtga gttgtaggca ttttttccat    42780
tactttctga ttcataggct caacgcacct caaagctgga aatgccgggt ctgggtacac    42840
cctggggaac tgcaaagcct gcacacttgg gggaaatgat caagatgaga ggcagggtg     42900 gggatggcat gtgcaccagg agatgttaga gaaaccctga ggaagagcag cgtgcagcag    42960
gtgatggggg agagtgggca gcaagcgagg ccaggacagc cactctgctc agtcaccagt    43020
ccacacaccc aggggctcac tctgcccctc tgagcaccca aggacgttaa agagctggaa    43080
ctgttagtct aaatatagga ccatccaagc tctgaaccaa aatgtgtccc ttgcctcaac    43140
tcaggagatc cacagaggca gaagtaagga atttattttc tgaaagatag atttctatca    43200
gttctgggtg acatgttctg acacttgaaa tgacacctag gacagcacat ttcaggcatc    43260
ttgctcattg ttcactgtag tagaagctac atgctagcca gttgtaaaaa tgaaattaag    43320
taatgtgtgc acagcattta acatagcatc tgagcttcag gagcactcaa ttaatgacca    43380
cagttgtgat tctttaggca gatgcatttt tttccaactt tgatcagagg tcttatttag    43440
cttctccaga tttcaagaat ctggctcagt gatatgaaat acaagacttg tgaaaagtgt    43500
caattgcaag agaaatggaa ggataaagta tacaggtggg tggaaaagaa attcacagtc    43560
actgccagaa aaaaaattct tgagaatcaa gtcctgatga tgttagggct tatagttctt    43620
attataaaga gttttatgta ctcattcagt gaacatttat tggtgcctcc tttagccagg    43680
tactatcata agagctgaaa ataaaagcat aatccagtcc ttgatcttga ggaacatgct    43740
gtgtgtagca gataacataa taagtgctta tctagatgca tgcagtgtta tgtgataaga    43800
```

```
gtaatatgac agaggataca gattaggctt cacagagaag ggggatttga gcaggaggta    43860
ttgaagggtg aatagaagct caccaatcat tttgggcaga ggggcaagga cctgcaaaac    43920
cactgaagca tgaaggaaat ggtgagttta gggaaaatga agagaagatg gctgtgactg    43980
aagcacagga tttgggattg gagaagggac tggaggtgag gctgagaaga ggcaaactca    44040
gaaaagatgt tgtgctgggc agtctggaca ttatctttga agcccaccac atataagtca    44100
tagggctact ggaggtttta agctaaaagt gactattcaa tttcaactta agagaagata    44160
ggttgagagg gaacatggct tgagatgagc catgagcaaa ggaaagacta caacaaagcc    44220
aggagtgagg agtgtgtgaa gcaagaaagt gacagttgaa agcagtgcag aggggatgaa    44280
tctgagaggc atctatgagg tggaactcaa atgacatgat aataatacag gcatttctc     44340 tgtgtcagat gctgtcctaa gtccttactc cattgatctt cacagcaact cagcatagtt    44400 aatatttat gcataaagaa atcggcactt gaaggagtaa ttggcccag attacactgc       44460 ctataaggat tcaaatccag gtttgtttgg ctccaaaaac tggctcctaa ttttcagaag     44520
gagaagcgac ccagggcaat gcccaatttt gcttcttagg caatggagga atccacaatc    44580
ggaaggagtt ttcagcagtg ccccatttgg ggtgggttga atttgaggtc cctgcatgat    44640
acccactttg ctcacttcag tgcctaaaac tgagtatggt tcatagtagg tgttcaataa    44700
gtgttgatgc agtgaataca tgcatgggga gatatgcatc aggcaatggg aaattcaact    44760
ctaaggctta ggggaaagct ggagcttgaa gacagagctt tagaaaacag tagcatagaa    44820
gggagtagga accatgagtt tagacaatac aattcaggaa gaactttgta gcaaggataa    44880
agaggcaaaa aattaaagag gtgagagcta agtgtggtgc ctggggaatc ttaaggtgtg    44940
ggcacgggga ggagatgcca gcaaagaaca tgaataaaaa gcggtagcac agcccctccc    45000
atctggaagc caaaagaat tgtaaatgga ggaagttagc agaaggatca aatacttgaa     45060
gagggtggaa ttggaataaa accagggcat ttgaaaaatt ggttgtcac tgcaatctta     45120 acaagagaag tttggcagg atgatggagg cagaaagctg agagaatcat cagttagaac    45180 gttttgact tcagagaaca gaaaatgcag ttcataatgg cttaaaaaca ggggcttgtt     45240
tttctcccag caatttgaga ggccaaggcg ggtgcatcag gaggtcaaga gaccgagacc    45300
atcctggcca acatggtgaa tccccatctc tactaaaaat acaaaaatta gcggggcatg    45360
gtggtgcacg cctatagtcc catctactca ggaggctgag gcaggagaat cacttgaacc    45420
caggaggtgg aggttgcagt gagctgagat catggccact gcactatagc ctggagacac    45480
agcgagactc cgtctccaaa aaaaaaaaaa aagaaggcag aaggtgaata gttcaagggt    45540
gggtttagga ctcagtgata ataggattct gcctggcttc tcatggttct ctaggtcttc    45600
cattcatggc accatgccct cactaggcat gctgccagag caggagggc aggtggaggg     45660 ttctcttgtg tctgtcttat cagggaagaa gagctttctc agaagccccc agcagactcc    45720
cttttcatat tatggtccag caatgagtca cagacctatg caccacctgc aaaggagcca    45780
gagaaaacaa acgcccagcg ctttagcct gaaaatgaga atctggttg ctggggaaga      45840 taagggtgt cggaaaatgg ctgttgggta aatcattgat gtctgccact aggaatgaaa     45900
ggcaaatcag gaactggcac acatgctttc agggagatgg ctgcaaggga gagggcaaag    45960
actgggaagt tgcttatgtg gtgccagact atttggaaga tcatggattg cggtgtttgt    46020
gttgtgtggt catcattttg ttctttgttt acagaacaga gaaagtggat tgaacaagga    46080
cgcatttccc cagtacatcc acaacatgct gtccacatct cgttctcggt ttatcagaaa    46140
```

```
taccaacgag agcggtgaag aagtcaccac cttttttgat tatgattacg gtgctccctg    46200
tcataaattt gacgtgaagc aaattggggc ccaactcctg cctccgctct actcgctggt    46260
gttcatcttt ggttttgtgg gcaacatgct ggtcgtcctc atcttaataa actgcaaaaa    46320
gctgaagtgc ttgactgaca tttacctgct caacctggcc atctctgatc tgcttttttct   46380 tattactctc ccattgtggg ctcactctgc tgcaaatgag tgggtctttg ggaatgcaat    46440
gtgcaaatta ttcacagggc tgtatcacat cggttatttt ggcggaatct tcttcatcat    46500
cctcctgaca atcgatagat acctggctat tgtccatgct gtgtttgctt aaaagccag     46560 gacggtcacc tttggggtgg tgacaagtgt gatcacctgg ttggtggctg tgtttgcttc    46620
tgtcccagga atcatcttta ctaaatgcca gaaagaagat tctgtttatg tctgtggccc    46680
ttattttcca cgaggatgga ataatttcca cacaataatg aggaacattt tggggctggt    46740
cctgccgctg ctcatcatgg tcatctgcta ctcgggaatc ctgaaaaccc tgcttcggtg    46800
tcgaaacgag aagaagaggc ataggcagt gagagtcatc ttcaccatca tgattgttta    46860 cttttctcttc tggactccct ataacattgt cattctcctg aacaccttcc aggaattctt    46920
cggcctgagt aactgtgaaa gcaccagtca actggaccaa gccacgcagg tgacagagac    46980
tcttgggatg actcactgct gcatcaatcc catcatctat gccttcgttg gggagaagtt    47040
cagaaggtat ctctcggtgt tcttccgaaa gcacatcacc aagcgcttct gcaaacaatg    47100
tccagttttc tacagggaga cagtggatgg agtgacttca acaaacacgc cttccactgg    47160
ggagcaggaa gtctcggctg gtttataaaa cgaggagcag tttgattgtt gtttataaag    47220
ggagataaca atctgtatat aacaacaaac ttcaagggtt tgttgaacaa tagaaacctg    47280
taaagcaggt gcccaggaac ctcagggctg tgtgtactaa tacagactat gtcacccaat    47340
gcatatccaa catgtgctca gggaataatc cagaaaaact gtgggtagag actttgactc    47400
tccagaaagc tcatctcagc tcctgaaaaa tgcctcatta ccttgtgcta atcctctttt    47460
tctagtcttc ataatttctt cactcaatct ctgattctgt caatgtcttg aaatcaaggg    47520
ccagctggag gtgaagaaga gaatgtgaca ggcacagatg aatgggagtg agggatagtg    47580
gggtcagggc tgagaggaga aggagggaga catgagcatg gctgagcctg acaaagaca    47640 aaggtgagca aagggctcac gcattcagcc aggagatgat actggtcctt agccccatct    47700
gccacgtgta tttaaccttg aagggttcac caggtcaggg agagtttggg aactgcaata    47760
acctgggagt tttggtggag tccgatgatt ctcttttgca taagtgcatg acatattttt    47820
gctttattac agtttatcta tggcacccat gcaccttaca tttgaaatct atgaaatatc    47880
atgctccatt gttcagatgc ttcttaggcc acatcccct gtctaaaaat tcagaaaatt     47940
tttgtttata aagatgcat tatctatgat atgctaatat atgtatatgc aatatatata    48000
ggctcttgct tgatctctcc aggaggtagt gattatgaga aggggtgga gaatgatgag    48060 ttccttcacc aggagcaaag gacggggatc gtgtggaacc actgcagaac tatttccgga    48120
atcaactaag tggagagagc caggaaggct gcatcagaac ccagtaaagc ttcttgtctg    48180
gatctgagct ggtttgtttt gtgcttgctt ttccctgcct tgccactccc ctcactcttc    48240
tcttttcccc acagccttt tcacatagct cttggctgta ggattgcccc actccaaaaa    48300
ccagtgtgtg gaggtccagg agtgagacca ggaaagaatg tgaaagtgac tacacaagga    48360
ctcctcgatg gtcgtggaaa aggaaagtca attggcagag cccctgaagc cagtcttcag    48420
gacaaagaag gagcctagag acagaaatga cagatctctg ctttggaaat cacacgtctg    48480
gcttcacaga tgtgtgattc acagtgtgaa tcttggtgtc tacgttacca ggcaggaagg    48540
```

```
ctgagaggag agagactcca gctgggttgg aaaacagtat tttccaaact accttccagt    48600
tcctcattt tgaatacagg catagagttc agactttttt taaatagtaa aaataaaatt    48660
aaagctgaaa actgcaactt gtaaatgtgg taaagagtta gtttgagtta ctatcatgtc    48720
aaacgtgaaa atgctgtatt agtcacagag ataattctag ctttgagctt aagaattttg    48780
agcaggtggt atgtttggga gactgctgag tcaacccaat agttgttgat tggcaggagt    48840
tggaagtgtg tgatctgtgg gcacattagc ctatgtgcat gcagcatcta agtaatgatg    48900
tcgtttgaat cacagtatac gctccatcgc tgtcatctca gctggatctc cattctctca    48960
ggcttgctgc caaaagcctt ttgtgttttg ttttgtatca ttatgaagtc atgcgtttaa    49020
tcacattcga gtgtttcagt gcttcgcaga tgtccttgat gctcatattg ttccctattt    49080
tgccagtggg aactcctaaa tcaaattggc ttctaatcaa agcttttaaa ccctattggt    49140
aaagaatgga aggtggagaa gctccctgaa gtaagcaaag actttcctct tagtcgagcc    49200
aagttaagaa tgttcttatg ttgcccagtg tgtttctgat ctgatgcaag caagaaacac    49260
tgggcttcta gaaccaggca acttgggaac tagactccca agctggacta tggctctact    49320
ttcaggccac atggctaaag aaggtttcag aaagaagtgg ggacagagca gaacttttcac   49380
cttcatatat ttgtatgatc ctaatgaatg cataaaatgt taagttgatg gtgatgaaat    49440
gtaaatactg tttttaacaa ctatgatttg gaaaataaat caatgctata actatgttga    49500
taaaagattt aaaaacaact ggctgttttt ttacactgtg gtgtggaaga ttgtgttgtg    49560
ttcacaactt ttcacttctt cccctgtgtg attacacaca cctgccctg tggtgtgact    49620
tgcagtgcgc cctacaggcc acacaacccc atgccctcca ccactggctc tgctgctgga    49680
atgtgagcag aagtgacatc tgcctcatcc aagcagagcc tcttgctcag ccacaggaag    49740
gcccattcca gatcacaccc gtcagcccgt gcgccctggt gaatgagaag acacagggag    49800
ctgcagccac atataacatg agcaagaagt ctgtgtttgc tgtgataagc cactgagttt    49860
tagggggttgt ttgttaagaa gcacaaaaac cgattaagac atgtggtata tagtgacttc    49920
atatatagaa tctggaaaac tatccattta ttttcaatca tggaattcaa tatgacaagc    49980
atcccggagg gtctacctat                                                50000
```

<210> SEQ ID NO 3  
<211> LENGTH: 6065  
<212> TYPE: DNA  
<213> ORGANISM: Homo sapiens  
<220> FEATURE:  
<221> NAME/KEY: misc_feature  
<222> LOCATION: (5763)..(5763)  
<223> OTHER INFORMATION: n stands for any base  
<220> FEATURE:  
<221> NAME/KEY: misc_feature  
<222> LOCATION: (5834)..(5834)  
<223> OTHER INFORMATION: n stands for any base

<400> SEQUENCE: 3

```
ctggcgggac agcagcgtgg actcagtctc ctagggattt cccaactctc ccgcccgctt      60
gctgcatctg gacaccctgc ctcaggccct catctccact ggtcagcagg tgacctttgc     120
ccagcgccct gggtcctcag tgcctgctgc cctggagatg atataaaaca ggtcagaacc     180
ctcctgcctg tctgctcagt tcatccctag aggcagctgc tccaggtaat gccctctggg     240
gaggggaaag aggaggggag gaggatgaag aggggcaaga ggagctccct gcccagccca     300
gccagcaagc ctggagaagc acttgctaga gctaaggaag cctcggagct ggacgggtgc     360
```

```
cccccacccc tcatcataac ctgaagaaca tggaggcccg ggaggtgtca cttgcccaaa    420
gctacatagg gggtggggct ggaagtggct ccaagtgcag gttcccccct cattcttcag    480
gcttagggct ggaggaagcc ttagacagcc cagtcctacc ccagacaggg aaactgaggc    540
ctggaagagg gccagaaatc acccaaagac acacagcatg ttggctggac tggacggaga    600
tcagtccaga ccgcagtgcc ttgatgttca gtctggtggg ttttctgctc catcccaccc    660
acctcctttg ggcctcgatc cctcgccgct caccagtccc ccttctgaga gcccgtatga    720
gcaggagccg gcccctactc cttctggcag acccagctaa ggttctacct taggggccac    780
gccacctccc cagggagggg tccagaggca tggggacctg gggtgcccct cacaggacac    840
ttccttgcag gaacagaggt gccatgcagc cccgggtact ccttgttgtt gccctcctgg    900
cgctcctggc ctctgcccgt aagcacttgg tgggactggg ctggggcag ggtgaggca     960
acttggggat cccagtccaa tgggtggtca agcaggagcc ccagggctcg tccagaggcc   1020
gatccacccc actcagccct gctctttcct caggagcttc agaggccgag gatgcctccc   1080
ttctcagctt catgcagggc tacatgaagc acgccaccaa gaccgccaag gatgcactga   1140
gcagcgtgca ggagtcccag gtggcccagc aggccaggta cacccgctgg cctccctccc   1200
catccccccct gccagctgcc tccattccca cccgcccctg ccctggtgag atcccaacaa   1260
tggaatggag gtgctccagc ctcccctggg cctgtgctct tcagcctcct ctttcctcac   1320
agggcctttg tcaggctgct gcgggagaga tgacagagtt gagactgcat tcctcccagg   1380
tccctccttt ctcccggagc agtcctaggg ccgcgccgtt ttagccctca tttccatttt   1440
cctttccttt cccttctttt ctctttctat ttttctttct ttctttcttt ctttctttct   1500
ttctttcttt ctttctttct ttcctttctt tctttccttt ctttcttct tttctttctt   1560
tctctttctt tctttcttc cttttctttt cttccctct cttcctttct ctctttcttt   1620
cttcttcttt ttttttaat ggagtctccc tctgtcaccc aggctggagt gcagtggtgc   1680
catctcggct cactgcaacc tccgtctccc gggttcaacc cattctcctg cctcagcctc   1740
ccaagtagct gggattacag gcacgcgcca ccacacccag ctaattttg tattttagc    1800
agagatgggg tttcaccatg ttggccaggt tggtcttgaa ttcctgacct cagggatcc    1860
tcctgcctcg gcctcccaaa gtgctgggat tacaggcacg agccactgcg cctggcccca   1920
ttttcctttt ctgaaggtct ggctagagca gtggtcctca gccttttggg caccagggac   1980
cagttttgtg gtggacaatt tttccatggg ccagcgggga tggttttggg atgaagctgt   2040
tccacctcag atcatcaggc attagattct cataaggagc cctccaccta gatccctggc   2100
atgtgcagtt cacaataggg ttcacactcc tatgagaatg taaggccact tgatctgaca   2160
ggaggcggag ctcaggcgta ttgctcactc acccaccact cacttcgtgc tgtgcagccc   2220
ggctcctaac agtccatgga ccagtaccta tctatgactt ggggttggg gaccctgggc    2280
taggggtttg cctgggagg ccccacctga cccaattcaa gcccgtgagt gcttctgctt    2340
tgttctaaga cctggggcca gtgtgagcag aagtgtgtcc ttcctctccc atcctgcccc   2400
tgcccatcag tactctcctc tccctactc ccttctccac ctcaccctga ctggcattag    2460
ctggcatagc agaggtgttc ataaacattc ttagtcccca gaaccggctt tggggtaggt   2520
gttattttct cactttgcag atgagaaaat tgaggctcag agcgattagg tgacctgccc   2580
cagatcacac aactaatcaa tcctccaatg actttccaaa tgagaggctg cctccctctg   2640
tcctaccctg ctcagagcca ccaggttgtg caactccagg tggtgctgtt tgcacagaaa   2700
acaatgacag ccttgacctt tcacatctcc ccaccctgtc actttgtgcc tcaggcccag   2760
```

```
gggcataaac atctgaggtg acctggagat ggcagggttt gacttgtgct ggggttcctg   2820
caaggatatc tcttctccca gggtggcagc tgtgggggat tcctgcctga ggtctcaggg   2880
ctgtcgtcca gtgaagttga gagggtggtg tggtcctgac tggtgtcgtc cagtggggac   2940
atgggtgtgg gtcccatggt tgcctacaga ggagttctca tgccctgctc tgttgcttcc   3000
cctgactgat ttaggggctg ggtgaccgat ggcttcagtt ccctgaaaga ctactggagc   3060
accgttaagg acaagttctc tgagttctgg gatttggacc ctgaggtcag accaacttca   3120
gccgtggctg cctgagacct caatacccca agtccacctg cctatccatc ctgccagctc   3180
cttgggtcct gcaatctcca gggcttcccc tgtaggttgc ttaaaaggga cagtattctc   3240
agtgctctcc tacccacct  catgcctggc ccccctccag gcatgctggc ctcccaataa   3300
agctggacaa gaagctgcta tgagtgggcc gtcgcaagtg tgccatctgt gtctgggcat   3360
gggaaagggc cgaggctgtt ctgtgggtgg gcactggaca gactccaggt caggcaggca   3420
tggaggccag cgctctatcc accttctggt agctgggcta gtctctgggc tcagtttct   3480 tcatctctaa ggtaggaatc ccctccgta  ccctgcct tc cttgacagct ttgtgcggaa   3540
ggtcaaacag gacaataagt ttgctgatac tttgataaac tgttaggtgc tgcacaacat   3600
gacttgagtg tgtgccccat gccagccact atgcctggca cttaagtgtc atcagagttg   3660
agactgtgtg tgtttactca aaactgtgga gctgacctcc cctatccagg ccacctagcc   3720
ctcttaggcg cacgtgaagg gaggaggccg gatgggctag aggttggagt aagatgcaac   3780
gaggcactat tcttggctcc accacttgat atcagcctca gtttcttaca tgtaaagtgg   3840
atacaaccgt accccctcca ccgtaggttt gccgtgagat tgaaatgaga gagcgttcga   3900
accgtttggc acagcacctg cacgtaaaga tgcttgatca atgttgtcat gattacagtt   3960
gagctgactg ggcccttggg accggactgg agtggtgggg ggcagtgtcc tgggaccaaa   4020
aagaagcaca aggtctccca atagaggctg cttcctttgt gtccccacca cccgaaagat   4080
gtcaggtcag agagcccgag agctgcagat ggcttgagta gggctccact cttcagatca   4140
aaaaactgtg gcccggagag gcgaaggcac ttggccagca tcacagagcc agcacgtggc   4200
agggccagac cttgagccca ggtcagctgc gtgtattctg ctcagttggt gcagaaaaca   4260
gttttgtcac tcctatgtca ggtgttaggg actcctttac agatctcagt ggcatcagta   4320
catccagccc cacctggaga ctgctttctc tctgaaaatt ccccagggct tctctctggg   4380
ctgagagatc tcagcacccg tatctagaaa atgttcccac ccagacctgg ctggatgact   4440
gctgttgtag ctctggaagg ttaggaacta aaaagcccac tcctttacct agggtagcta   4500
agatacactg gagatgggga catggggatg ggccgattac tccaggggcc tgcatgaggg   4560
ggcaaaaggc cctgcagaga gagggtaggg aaggcactgc cagatctgtg aagccatgtg   4620
cgtgcagcgg ggacattcag acatgagtgc aaggagggac cgtgagcagg gaggtcatgt   4680
gagaatacac aggcatgcct gcacacccat gtgaacttga gtgccaggcc acacactctt   4740
tttttttttt tttttttttt tagctggagt cttgctccgt cgcccaggct ggagtgcagt   4800
ggcatgattt cggctcactg tgacctctgc ctcccaggtt caagcgattc tcctgcctca   4860
gccttcctag tagctgggat tacgggtgca agccaccatg ccagctgatt ttttttttgt   4920 attttttagta gagacagggt ttcaccatat tggccaggct ggtctcaaac tcctggccct   4980
gaagtgatac gcccacctca gcctcccaaa gtgctgggat tacaggcttg agccaccgca   5040
cccgacccgc acactctttt caataatcat ggatggccag gggtgcaggg tctaaaaagc   5100
```

-continued

```
gctgcctagc ccatcctgct gttcactggg caagcgacgt cacaggtcca ggcttcagtg    5160
tcctcatcca tgctctgcgt ctgatggcaa tctagccagg atgtggggaa gggaggatgc    5220
agtgagagca cagatatgag agcatcttgg aaataaaaat gtacctgcaa gaggtggtgg    5280
tgaattttct tactcaggcc agcttctgcc agggctggca gaaagagggg gtggcatggc    5340
atggagccgc aggggtggag ggactggctt ccactgctgt gcctgaggaa gccgcggctg    5400
tttctgggcg ggatgggagt agtgggaggg ggatactggc cttgtgagaa gaaaagggaa    5460
gtgtctgttt gagaggtttt tgaattagta aggaggaca ggcgcaaact ccaagcgctt     5520
cacttgcacc cgggaccaaa ccccaatccc agtggctggc tccctgaggc gccccgctcc    5580
gtcccgcccg ctgacagcgg ctgggctgga aaggctcta tacggacaca cctctgggga    5640
cggggaaccc gactgctccc agctaaagca accgctgttt cctggcccgc tcagacagg    5700 ctgcaggcct tgtttgagcc cctttcaggg cacctggcct tggattgtct gtggctttgc    5760
ctngtccgct gtgacttcct ttctacttga gccttgctaa gcagactct actccctcac     5820 tcgtaagcag ccangcgtcc agcaggtcct ccaacgtcga tcttggccct aagacgtcca    5880
gtctgggcac ggagttgttg agatccggca ggaagtccct gctccagggc caaaggcccc    5940
tcccgggctc ccccggatgt ccccgcaccc ccctctattc tcccaaaaga agaagctgc     6000 ttcccacttt ggaaacgttt attctgagca ccgggaaggg gggcggcggc gggcgcctca    6060
ctggg                                                                6065
```

```
<210> SEQ ID NO 4
<211> LENGTH: 1523
<212> TYPE: DNA
<213> ORGANISM: Homo sapiens

<400> SEQUENCE: 4
```

```
gggtcgatgg gggagatgga gcaactgcgt caggaagcgg agcagctcaa gaagcagatt      60
gcagatgcca ggaaagcctg tgctgacgtt actctggcag agctggtgtc tggcctagag     120
gtggtgggac gagtccagat gcggacgcgg cggacgttaa ggggacacct ggccaagatt     180
tacgccatgc actgggccac tgattctaag ctgctggtaa gtgcctcgca agatgggaag    240
ctgatcgtgt gggacagcta caccaccaac aaggtgcacg ccatcccact gcgctcctcc    300
tgggtcatga cctgtgccta tgccccatca gggaactttg tggcatgtgg ggggctggac    360
aacatgtgtt ccatctacaa cctcaaatcc cgtgagggca atgtcaaggt cagccgggag    420
ctttctgctc acacaggtta tctctcctgc tgccgcttcc tggatgacaa caatattgtg    480
accagctcgg gggacaccac gtgtgccttg tgggacattg agactgggca gcagaagact    540
gtatttgtgg gacacacggg tgactgcatg agcctggctg tgtctcctga cttcaatctc    600
ttcatttcgg gggcctgtga tgccagtgcc aagctctggg atgtgcgaga ggggacctgc    660
cgtcagactt tcactggcca cgagtcggac atcaacgcca tctgtttctt ccccaatgga    720
gaggccatct gcacgggctc ggatgacgct tcctgccgct gtttgacct gcgggcagac     780 caggagctga tctgcttctc ccacgagagc atcatctgcg gcatcacgtc cgtggccttc    840
tccctcagtg gccgcctact attcgctggc tacgacgact tcaactgcaa tgtctgggac    900
tccatgaagt ctgagcgtgt gggcatcctc tctggccacg ataacagggt gagctgcctg    960
ggagtcacag ctgacgggat ggctgtggcc acaggttcct gggacagctt cctcaaaatc   1020
tggaactgag gaggctggag aaagggaagt ggaaggcagt gaacacactc agcagccccc   1080
tgcccgaccc catctcattc aggtgttctc ttctatattc cgggtgccat tcccactaag   1140
```

-continued

```
ctttctcctt tgagggcagt ggggagcatg ggactgtgcc tttggaggc  agcatcaggg    1200 acacaggggc aaagaactgc cccatctcct cccatggcct tccctcccca cagtcctcac    1260
agcctctccc ttaatgagca aggacaacct gccctcccc  agcccttgc  aggcccagca    1320 gacttgagtc tgaggcccca ggccctagga ttcctcccc  agagccacta cctttgtcca    1380
ggcctgggtg gtatagggcg tttggccctg tgactatggc tctggcacca ctagggtcct    1440
ggccctcttc ttattcatgc tttctccttt ttctacctt  ttttctctcc taagacacct    1500
gcaataaagt gtagcaccct ggt                                            1523
```

<210> SEQ ID NO 5
<211> LENGTH: 1178
<212> TYPE: DNA
<213> ORGANISM: Homo sapiens
<220> FEATURE:
<221> NAME/KEY: misc_feature
<222> LOCATION: (881)..(881)
<223> OTHER INFORMATION: n stands for any base

<400> SEQUENCE: 5

```
ggggaagcaa aggagaagct gagaagatga aggaaaagtc agggtctgga ggggcggggg      60
tcagggagct cctgggagat atggccacat gtagcggctc tgaggaatgg gttacaggag     120
acctctgggg agatgtgacc acagcaatgg gtaggagaat gtccagggct atggaagtcg     180
agtatcgggg acccccctt  aacgaagaca gggccatgta gagggcccca gggagtgaaa     240
gagcctccag gacctccagg tatggaatac aggggacgtt taagaagata tggccacaca     300
ctggggccct gagaagtgag agcttcatga aaaaaatcag ggaccccaga gttccttgga     360
agccaagact gaaaccagca ttatgagtct ccgggtcaga atgaaagaag aaggcctgcc     420
ccagtggtct gtgaattccc gggggtgatt tcactccccg gctgtccca  ggcttgtccc     480 tgctacccc  acccagcctt tcctgaggcc tcaagctgcc accaagcccc cagctccttc     540
tccccgcaga cccaaacaca ggcctcagga ctcaacacag cttttccctc caacccgtt      600 ttctctccct caaggactca gcttctgaa  gcccctccca gttctagttc tatctttttc     660
ctgcatcctg tctggaagtt agaaggaaac agaccacaga cctggtcccc aaaagaaatg     720
gaggcaatag gttttgaggg gcatgggac  ggggttcagc ctccagggtc ctacacacaa     780
atcagtcagt ggcccagaag accccccctcg gaatcggagc agggaggatg gggagtgtga    840
ggggtatcct tgatgcttgt gtgtccccaa ctttccaaat nccgccccc  gcgatggaga     900 agaaaccgag acagaaggtg cagggcccac taccgcttcc tccagatgag cttatgggtt     960
tctccaccaa ggaagttttc cgctggttga atgattcttt cccgccctc  ctctcgcccc    1020 agggacatat aaaggcagtt gttggcacac ccagccagca gacgctccct cagcaaggac    1080
agcagaggac cagctaagag ggagagaagc aactgcagac ccccctgaa  aacaaccctc    1140 agacgccaca tcccctgaca agctgccagg caggttct                            1178
```

<210> SEQ ID NO 6
<211> LENGTH: 6152
<212> TYPE: DNA
<213> ORGANISM: Homo sapiens

<400> SEQUENCE: 6

```
tggtatttgg gcggctggtg gcggcgggga ctgttggagg gtgggaggag gcgaaggagg      60
agggagaacc ccgtgcaacg ttgggacttg gcaacccgcc tccccctgcc caaggatatt     120
```

-continued

```
taatttgcct cgggaatcgc tgcttccaga ggggaactca ggagggaagg gggcgcgcgc      180
tcctggaggg gcaccgcagg gacccccgac tgtcgcctcc ctgtgccgga ctccagccgg      240
ggcgacgaga gatgcatctt cgctccttcc tggtggcggc ggcggctgag aggagacttg      300
gctctcggag gatcggggct gccctcaccc cggacgcact gcctcccgc cgggcgtgaa       360 gcgcccgaaa actccggtcg ggctctctcc tgggctcagc agctgcgtcc tccttcagct      420 gccccctcccc gcgcggggg cggcgtggat ttcagagtcg gggtttctgc tgcctccagc     480
cctgtttgca tgtgccgggc gcgggcgagg agcctccgcc ccccaccggg ttgttttttcg     540 gagcctccct ctgctcagcg ttggtggtgg cgtggcagc atggcgagcc ctccggagag       600
cgatggcttc tcggacgtgc gcaaggtggg ctacctgcgc aaacccaaga gcatgcacaa      660
acgcttcttc gtactgcgcg cggccagcga ggctggggc ccggcgcgcc tcgagtacta       720
cgagaacgag aagaagtggc ggcacaagtc gagcgccccc aaacgctcga tccccccttga    780 gagctgcttc aacatcaaca agcgggctga ctccaagaac aagcacctgg tggctctcta     840
caccccggac gagcactttg ccatcgcggc ggacagcgag gccgagcaag acagctggta     900
ccaggctctc ctacagctgc acaaccgtgc taagggccac cacgacggag ctgcggccct     960
cggggcggga ggtggtggtg ggggcagctg cagcggcagc tccggccttg gtgaggctgg    1020
ggaggacttg agctacgtg acgtgccccc aggacccgca ttcaaagagg tctggcaagt     1080
gatcctgaag cccaagggcc tgggtcagac aaagaacctg attggtatct accgcctttg    1140
cctgaccagc aagaccatca gcttcgtgaa gctgaactcg gaggcagcgg ccgtggtgct    1200
gcagctgatg aacatcaggc gctgtggcca ctcggaaaac ttcttcttca tcgaggtggg    1260
ccgttctgcc gtgacgggc ccggggagtt ctggatgcag gtggatgact ctgtggtggc     1320
ccagaacatg cacgagacca tcctggaggc catgcgggcc atgagcgatg agttccgccc    1380
tcgcagcaag agccagtcct cgtccaactg ctctaacccc atcagcgtcc ccctgcgccg    1440
gcaccatctc aacaatcccc cgcccagcca ggtgggcctg accgcgat cacgcactga      1500 gagcatcacc gccacctccc cggccagcat ggtgggcggg aagccaggct ccttccgtgt    1560
ccgcgcctcc agtgacggcg aaggcaccat gtcccgccca gcctcggtgg acggcagccc    1620
tgtgagtccc agcaccaaca gaacccacgc ccaccggcat cggggcaggg cccggctgca    1680 cccccccgctc aaccacagcc gctccatccc catgccggct tcccgctgct cccgttcggc    1740
caccagcccg gtcagtctgt cgtccagtag caccagtggc catggctcca cctcggattg    1800
tctcttccca cggcgatcta gtgcttcggt gtctggttcc cccagcgatg gcggtttcat    1860
ctcctcggat gagtatggct ccagtccctg cgatttccgg agttccttcc gcagtgtcac    1920
tccggattcc ctgggccaca ccccaccagc ccgcggtgag gaggagctaa gcaactatat    1980
ctgcatgggt ggcaaggggc cctccaccct gaccgccccc aacggtcact acatttttgtc    2040 tcggggtggc aatggccacc gctgcacccc aggaacaggc ttgggcacga gtccagcctt    2100
ggctggggat gaagcagcca gtgctgcaga tctggataat cggttccgaa agagaactca    2160
ctcggcaggc acatccccta ccattaccca ccagaagacc ccgtcccagt cctcagtggc    2220
ttccattgag gagtacacag agatgatgcc tgcctaccca ccaggaggtg gcagtggagg    2280
ccgactgccg ggacacaggc actccgcctt cgtgcccacc cgctcctacc agaggaggg     2340 tctggaaatg caccccttgg agcgtcgggg ggggcaccac cgcccagaca gctccaccct    2400
ccacacggat gatggctaca tgcccatgtc cccaggggtg gccccagtgc ccagtggccg    2460
aaagggcagt ggagactata tgcccatgag ccccaagagc gtatctgccc cacagcagat    2520
```

```
catcaatccc atcagacgcc atccccagag agtggacccc aatggctaca tgatgatgtc   2580
ccccagcggt ggctgctctc ctgacattgg aggtggcccc agcagcagca gcagcagcag   2640
caacgccgtc ccttccggga ccagctatgg aaagctgtgg acaaacgggg tagggggcca   2700
ccactctcat gtcttgcctc accccaaacc cccagtggag agcagcggtg gtaagctctt   2760
accttgcaca ggtgactaca tgaacatgtc accagtgggg gactccaaca ccagcagccc   2820
ctccgactgc tactacggcc ctgaggaccc ccagcacaag ccagtcctct cctactactc   2880
attgccaaga tcctttaagc acacccagcg ccccggggag ccggaggagg gtgcccggca   2940
tcagcacctc cgcctttcca ctagctctgg tcgccttctc tatgctgcaa cagcagatga   3000
ttcttcctct tccaccagca gcgacagcct gggtggggga tactgcgggg ctaggctgga   3060
gcccagcctt ccacatcccc accatcaggt tctgcagccc catctgcctc gaaaggtgga   3120
cacagctgct cagaccaata gccgcctggc ccggcccacg aggctgtccc tgggggatcc   3180
caaggccagc accttacctc gggcccgaga gcagcagcag cagcagcagc ccttgctgca   3240
ccctccagag cccaagagcc ggggggaata tgtcaatatt gaatttggga gtgatcagtc   3300
tggctacttg tctggcccgg tggctttcca cagctcacct tctgtcaggt gtccatccca   3360
gctccagcca gctcccagag aggaagagac tggcactgag gagtacatga agatggacct   3420
ggggccgggc cggagggcag cctggcagga gagcactggg gtcgagatgg cagactggg   3480 ccctgcacct cccggggctg ctagcatttg caggcctacc cgggcagtgc ccagcagccg   3540
gggtgactac atgaccatgc agatgagttg tccccgtcag agctacgtgg acacctcgcc   3600
agctgcccct gtaagctatg ctgacatgcg aacaggcatt gctgcagagg aggtgagcct   3660
gcccagggcc accatggctg ctgcctcctc atcctcagca gcctctgctt ccccgactgg   3720
gcctcaaggg gcagcagagc tggctgccca ctcgtccctg ctgggggcc cacaaggacc   3780 tgggggcatg agcgccttca cccgggtgaa cctcagtcct aaccgcaacc agagtgccaa   3840
agtgatccgt gcagacccac aagggtgccg gcggaggcat agctccgaga ctttctcctc   3900
aacacccagt gccaccccggg tgggcaacac agtgcccttt ggagcggggg cagcagtagg   3960
gggcggtggc ggtagcagca gcagcagcga ggatgtgaaa cgccacagct ctgcttcctt   4020
tgagaatgtg tggctgaggc ctggggagct tgggggagcc cccaaggagc cagccaaact   4080 gtgtgggget gctggggggtt tggagaatgg tcttaactac atagacctgg atttggtcaa   4140
ggacttcaaa cagtgccctc aggagtgcac ccctgaaccg cagcctcccc cacccccacc   4200
ccctcatcaa cccctgggca gcggtgagag cagctccacc cgccgctcaa gtgaggattt   4260
aagcgcctat gccagcatca gtttccccgaaa gcagccagag gaccgtcagt agctcaactg   4320
gacatcacag caggtcgttt catggtgaca aagtcagaag acaaaactgc ttttaacctt   4380
gtccttgaat tctgttcttc gcctctgccc cttcctgttc tttcccactg cttcctcagg   4440
gagaatgcac ttacattctc agggcataca agatgctcac ccacactgac attggcagag   4500
agtcaaacaa acatgtagga gcagccacag gagggctttt tcgtttgagg aattcccaag   4560
tgaagtagtt actgcagtat ttttaaacat atatcctatg ccagttctgc gttttgtaga   4620
gttcctccgt aagaagcttg atttgtttgt tgaagttttc ttttcactat atatttaggt   4680
cagcccctgg aaggacagtt ctacaaaaaa taccggttaa cacaggggct aaacccttcc   4740
ttatcttaaa ctatcttaat agtttctggg agccctaagg ggtgatctta tcaagttgtt   4800
ctctgtactt ttgttctgtg atttcataat actagggcaa cataaacagc agcgggaagc   4860
```

```
attgatttct attcatcctg ccctaaaaag atcaggagta agagcttttt agaaatatgt    4920
atttagagag aagtacctat ctattttgtg atctctcaag aaagtaatta tgggtgacgt    4980
tctccttttg ttcatgtacc aggatttgtg aaatattatt cacacaaccg acccaccatc    5040
ccacgggcct ggcctctctt gtacaggata tgcaggaaac tctgtatgtg tctgggaccc    5100
attattaaga gttatgggag ttcatcctag gatgtctgcc ttatagttat ctcttcttct    5160
tgcactgaga cattacagat atcatttggg ggctactata tatcttctgt aaaattactt    5220
ttatttgttg aagaagaatg catactaagt caggaacatg ccttaatttg ttttgttttg    5280
caattgagta gaagggctaa actgtatccc tccacttta gggttatttg cctgtgtgcc    5340
tttaagttca aaagtagaca ccacagtaaa tgctgaaagt tggctttagg tcttctgtgg    5400
ctaatgccgt attaaaaatg aaaaacattt gtggtagaaa ttagcctgcc cttcgttctg    5460
ttgatcctgt tttctggtgg tcataattgt gggtagaaga gagtacagtt tgcaaataat    5520
gtgatgagtt ggcaatgcag aagtttccag catttggaaa cactttactc tgacaaactg    5580
attatcttgt gaattttatc tatgctccac agaatgagct tttaaaagca ctgattttc    5640 ttaatttgtg tccattcata agaaattaat ctgtgccctg gtttcctatt gacaggtatt    5700
tatttatcat gtgttcatag tcttcttaat tctgtttcca atatttgatc catataattc    5760
tctattttat aaagcaagaa aaaggtatat gaacactcaa atgaagattt tgggtgatat    5820
gttacaaaaa gcatttattt gatcagtatt tacttcaaca tttattttca tcattcacta    5880
gaagaaagat ttaattgtgt atatcaacat cagtagtaca aatcttgtta tatcaaatga    5940
tgtttttggg agttcagaat ccctcaacac tttaagcatt tgtattataa agtgcctcat    6000
tggtaaaata atgagaattt gaagaaaacc agcccagcag aactaaaatt ttggttttaa    6060
aggagataaa gagaataagt ttttcttact tgtcatctta atttgtttag gtttcttttt    6120
atagagtaga ataaatgatg tttgctctga ag                                  6152
```

<210> SEQ ID NO 7
<211> LENGTH: 2480
<212> TYPE: DNA
<213> ORGANISM: Homo sapiens

<400> SEQUENCE: 7

```
gacgctctgt gccttcggag gtctttctgc ctgcctgtcc tcatgcctct cctcctcttg     60
ctgctcctgc tgccaagccc cttacacccc cacccatct gtgaggtctc caaagtggcc    120
agccacctag aagtgaactg tgacaagagg aatctgacag cgctgcctcc agacctgccg    180
aaagacacaa ccatcctcca cctgagtgag aacctcctgt acaccttctc cctggcaacc    240
ctgatgcctt acactcgcct cactcagctg aacctagata ggtgcgagct caccaagctc    300
caggtcgatg ggacgctgcc agtgctgggg accctggatc tatcccacaa tcagctgcaa    360
agcctgccct gctaggca gacactgcct gctctcaccg tcctgacgt ctccttcaac    420 cggctgacct cgctgcctct tggtgccctg cgtggtcttg gcgaactcca agagctctac    480
ctgaaaggca tgagctgaa gaccctgccc ccagggctcc tgacgcccac acccaagctg    540
gagaagctca gtctggctaa caacaacttg actgagctcc ccgctgggct cctgaatggg    600
ctggagaatc tcgacaccct tctcctccaa gagaactcgc tgtatacaat accaaagggc    660 ttttttggt cccacctcct gcctttttgct tttctccacg ggaacccctg gttatgcaac    720
tgtgagatcc tctattttcg tcgctggctg caggacaatg ctgaaaatgt ctacgtatgg    780
aagcaaggtg tggacgtcaa ggccatgacc tctaacgtgg ccagtgtgca gtgtgacaat    840
```

```
tcagacaagt tcccgtctca caaatacccca ggaaaggggt gccccaccct tggtgatgaa    900
ggtgacacag acctatatga ttactaccca gaagaggaca ctgagggcga taaggtgcgt    960
gccacaagga ctgtggtcaa gttccccacc aaagcccata caaccccctg gggtctattc   1020
tactcatggt ccactgcttc tctagacagc caaatgccct cctccttgca tccaacacaa   1080
gaatccacta aggagcagac cacattccca cctagatgga ccccaaattt cacacttcac   1140
atggaatcca tcacattctc caaaactcca aaatccacta ctgaaccaac cccaagcccg   1200
accacctcag agcccgtccc ggagcccgcc caaacatga ccaccctgga gcccactcca   1260
agcccgacca ccccagagcc cacctcagag cccgcccca gcccgaccac cccggagccc   1320
accccaatcc cgaccatcgc cacaagcccg accatcctgg tgtctgccac aagcctgatc   1380
actccaaaaa gcacattttt aactaccaca aaacccgtat cactcttaga atccaccaaa   1440
aaaaccatcc ctgaacttga tcagccacca aagctccgtg gggtgctcca agggcatttg   1500
gagagctcca gaaatgaccc ttttctccac cccgactttt gctgcctcct ccccctgggc   1560
ttctatgtct tgggtctctt ctggctgctc tttgcctctg tggtcctcat cctgctgctg   1620
agctgggttg ggcatgtgaa accacaggcc ctggactctg gccaaggtgc tgctctgacc   1680
acagccacac aaaccacaca cctggagctg cagaggggac ggcaagtgac agtgccccgg   1740
gcctggctgc tcttccttcg aggttcgctt cccacttttcc gctccagcct cttcctgtgg   1800
gtacggccta atggccgtgt ggggcctcta gtggcaggaa ggaggccctc agctctgagt   1860
cagggtcgtg gtcaggacct gctgagcaca gtgagcatta ggtactctgg ccacagcctc   1920
tgagggtggg aggtttgggg accttgagag aagagcctgt gggctctcct attggaatct   1980
agttggggt tggagggta aggaacacag ggtgataggg gaggggtctt agttccttt    2040
tctgtatcag aagccctgtc ttcacaacac aggcacacaa tttcagtccc agccaaagca   2100
gaagggtaa tgcatggac ttggcgggg gacaagacaa agctcccgat gctgcatggg   2160
gcgctgccag atctcacggt gaaccatttt ggcagaatac agcatggttc ccacatgcat   2220
ttatgcacag aagaaaatct ggaaagtgat ttatccaggat gtgagcactc gttgtgtctg   2280
gatgttacaa atatgggtgg ttttatttc ttttccctg tttagcattt tctagttttc   2340
ttatcaggat gtgagcactc gttgtgtctg gatgttacaa atatgggtgg ttttatttc   2400
ttttcccctg tttagcattt tctagttttc cactattatt gtatattatc tgtataataa   2460
aaaataattt tagggttggg                                                2480
```

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (23)..(23)
<223> OTHER INFORMATION: n stands for any base

<400> SEQUENCE: 8
gagtctacct gtttactatc aanaa                                            25

<210> SEQ ID NO 9
<211> LENGTH: 25
<212> TYPE: DNA
<213> ORGANISM: Artificial Sequence
<220> FEATURE:

```
<223> OTHER INFORMATION: Description of Artificial Sequence:Primer
<220> FEATURE:
<221> NAME/KEY: misc_feature
<222> LOCATION: (23)..(23)
<223> OTHER INFORMATION: n stands for any base

<400> SEQUENCE: 9
gagtctacct gtttactatc aanga                                           25

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:Primer

<400> SEQUENCE: 10
accagtacta aagcaaatta aact                                            24

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (20)..(20)
<223> OTHER INFORMATION: n stands for any base

<400> SEQUENCE: 11
gcagtttatt aagatgaggn cg                                              22

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (22)..(22)
<223> OTHER INFORMATION: n stands for any base

<400> SEQUENCE: 12
ttgcagttta ttaagatgag gntg                                            24

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 13
ggtgctccct gtcataaatt tga                                             23

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 14
ccttctcagc ttcatgcagg                                                 20
```

```
<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:Primer

<400> SEQUENCE: 15
gtcttggtgg cgtgcttca                                                19

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 16
tctgcggcat cacgtncg                                                 18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 17
tctgcggcat cacgtntg                                                 18

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 18
gaatagtagg cggccactga                                               20

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (19)..(19)
<223> OTHER INFORMATION: n stands for any base

<400> SEQUENCE: 19
tctacatggc cctgtcttng t                                             21

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence:Primer
<220> FEATURE:
```

```
<221> NAME/KEY: misc_feature
<222> LOCATION: (20)..(20)
<223> OTHER INFORMATION: n stands for any base

<400> SEQUENCE: 20
ctctacatgg ccctgtcttn at                                              22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 21
ctctacatgg ccctgtcttt at                                              22

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (17)..(17)
<223> OTHER INFORMATION: n stands for any base

<400> SEQUENCE: 22
ccccatcctc cctgctncg                                                  19

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (17)..(17)
<223> OTHER INFORMATION: n stands for any base

<400> SEQUENCE: 23
ccccatcctc cctgctntg                                                  19

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 24
agtcagtggc ccagaagacc                                                 20

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 25
gggccctgca cctccngg                                                   18
```

```
<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (16)..(16)
<223> OTHER INFORMATION: n stands for any base

<400> SEQUENCE: 26
gggccctgca cctccnag                                                 18

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 27
gggtaggcct gcaaatgcta                                               20

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (14)..(14)
<223> OTHER INFORMATION: n stands for any base

<400> SEQUENCE: 28
cccagggctc ctgncg                                                   16

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (15)..(15)
<223> OTHER INFORMATION: n stands for any base

<400> SEQUENCE: 29
ccccagggct cctgntg                                                  17

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence:Primer

<400> SEQUENCE: 30
tgagcttctc cagcttgggt g                                             21

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:Probe
```

-continued

```
<400> SEQUENCE: 31
cagcttcatg cagggctaca                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence:Probe

<400> SEQUENCE: 32
cagcttcatg cagggttaca                                              20

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence:Probe
<220> FEATURE:
<221> NAME/KEY: misc_feature
<222> LOCATION: (16)..(16)
<223> OTHER INFORMATION: n stands for any base

<400> SEQUENCE: 33
acatggccct gtcttngtta ag                                           22

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence:Probe
<220> FEATURE:
<221> NAME/KEY: misc_feature
<222> LOCATION: (16)..(16)
<223> OTHER INFORMATION: n stands for any base

<400> SEQUENCE: 34
acatggccct gtcttnatta ag                                           22

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence:Probe
<220> FEATURE:
<221> NAME/KEY: misc_feature
<222> LOCATION: (8)..(8)
<223> OTHER INFORMATION: n stands for any base

<400> SEQUENCE: 35
cacctccngg ggctgctag                                               19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence:Probe
<220> FEATURE:
<221> NAME/KEY: misc_feature
<222> LOCATION: (8)..(8)
<223> OTHER INFORMATION: n stands for any base

<400> SEQUENCE: 36
cacctccnag ggctgctag                                               19
```

METHOD OF PREDICTING GENETIC RISK FOR HYPERTENSION

This application is the national state of PCT/JP03/12052, filed Sep. 22, 2003.

TECHNICAL FIELD

The present invention relates to a detection method using genes associated with hypertension. More particularly, it relates to a detection method using a plurality of gene polymorphisms associated with hypertension and to a kit used for the method. The present invention can be used for diagnosing a risk of development of hypertension.

BACKGROUND ART

Hypertension is a complex multifactorial and polygenic disorder that is thought to result from an interaction between an individual's genetic background and various environmental factors (see non-patent document 1). Given that hypertension is a major risk factor for coronary artery disease, stroke, and chronic renal failure, prevention of hypertension is an important public health goal. One approach to preventing the development of hypertension is to identify susceptibility genes. Linkage studies (see non-patent documents 2 to 4) and association studies with candictae genes (see non-patent documents 5 to 8) have implicated various chromosomal loci and genes in predisposition to hypertension. Although genetic epidemiological studies have suggested that certain genetic variants, including polymorphisms in the genes encoding angiotensinogen (non-patent document 5), α-adducin (non-patent document 6), the β3 subunit of G proteins (non-patent document 7) and the β2-adrenergic receptor (non-patent document 8), etc. increase the risk for hypertension, the genes that contribute to genetic susceptibility to hypertension remain to be identified definitively. In addition, because of ethnic divergence of gene polymorphisms, it is important to construct a database of polymorphisms related to hypertension in each ethnic group.

Non-patent document 1: Lifton R P, Gharavi A G, Geller D S. Molecular mechanisms of human hypertension. Cell. 2001; 104: 545-556.

Non-patent document 2: Xu X, Rogus J J, Terwedow H A, Yang J, Wang Z, Chen C, Niu T, Wang B, Xu H, Weiss S, Schork N J, Fang Z. An extreme-sib-pair genome scan for genes regulating blood pressure. Am J Hum Genet. 1999; 64: 1694-1701.

Non-patent document 3: Krushkal J, Ferrell R, Mockrin S C, Turner S T, Sing C F, Boerwinkle E. Genome-wide linkage analysis of systolic blood pressure using highly discordant siblings. Circulation. 1999; 99: 1407-141.

Non-patent document 4: Rice T, Rankinen T, Province M A, Chagnon Y C, Pérusse L, Borecki I B, Bouchard C, Rao D C. Genome-wide linkage analysis of systolic and diastolic blood pressure: the Québec Family Study. Circulation. 2000; 102: 1956-1963.

Non-patent document 5: Jeunemaitre X, Soubrier F, Kotelevtsev Y V, Lifton R P, Williams C S, Charru A, Hunt S C, Hopkins P N, Williams R R, Laouel J-M, Corvol P. Molecular basis of human hypertension: role of angiotensinogen. Cell. 1992; 71: 169-180.

Non-patent document 6: Cusi D, Barlassina C, Azzani T, Casari O, Citterio L, Devoto M, Gloriso N, Lanzani C, Manunta P, Righetti M, Rivera R, Stella P, Troffa C, Zagato L, Bianchi G. Polymorphisms of a-adducin and salt sensitivity in patients with essential hypertension. Lancet. 1997; 349: 1353-1357.

Non-patent document 7: Siffert W, Rosskop D, Siffert G, Busch S, Moritz A, Erbel R, Sharma A M, Ritz E, Wichmann H-E, Jakobs K H, Horsthemke B. Association of a human G-protein β3 subunit variant with hypertension. Nat Genet. 1998; 18: 45-48.

Non-patent document 8: Bray M S, Krushkal J, Li L, Ferrell R, Kardia S, Sing C F, Turner S T, Boerwinkle E. Positional genomic analysis identifies the β2-adrenergic receptor gene as a susceptibility locus for hypertension. Circulation. 2000; 101: 2877-2882.

SUMMARY OF THE INVENTION

As mentioned above, many association studies have previously examined the relations between gene polymorphisms and hypertension. The results of most of these studies, however, remain controversial, with no consensus on their implications, mainly because of the limited population size of the studies, the ethnic diversity of gene polymorphisms, and complicating environmental factors. Furthermore, even though associations with respect to hypertension have been detected, the relative risk (odds ratio) has tended to be low in large populations.

The present invention was made on the basis of the above-mentioned background, and the object thereof is to provide a means of diagnosing genetic risk for hypertension with high accuracy and high predictability so as to contribute primary prevention of hypertension.

To achieve the above-mentioned objects, the present inventors have extracted 71 genes which were estimated to be associated with coronary arteriosclerosis, coronary artery spasm, hypertension, diabetes mellitus, hyperlipidemia, etc., and mainly selected 112 polymorphisms which were predicted to be associated with functional changes of genes by the use of a plurality of public databases. Then, as to 112 polymorphisms of 71 genes, association study with respect to myocardial infarction was carried out in 445 myocardial cases and 464 controls. As a result, the present inventors have identified 19 and 18 single nucleotide polymorphisms (SNPs) related to myocardial infarction in men and women, respectively (Yamada Y, Izawa H, Ichihara S, et al. Prediction of the risk of myocardial infarction from polymorphisms in candidate genes. N Engl J Med. in press). However, these SNPs also include candidate determinants of the susceptibility to hypertension. Then, the present inventors therefore performed a large-scale association study for these SNPs and hypertension. As a result, the present inventors succeeded in identifying four and four SNPs related to hypertension in men and women, respectively. In addition, analysis of the combination of these polymorphisms revealed maximal odds ratios of 5.34 for men and 46.86 for women, respectively, on the basis of the stepwise forward selection method. In the analysis, the odds ratios were maximum among the odds ratios which had been reported in the past. Based on these results, it was possible to obtain findings that by selecting a plurality of SNPs from these SNPs and using the combination of the results of analysis of each SNP, diagnosis of hypertension can be carried out with high reliability and high predictability. The present invention was made based on the above-mentioned findings and provides the following configuration.

[1] A method for detecting the genotype in a nucleic acid sample, the method comprising the following step (a):
(a) analyzing two or more polymorphisms selected from the group consisting of the following (1) to (4) in a nucleic acid sample:
(1) a polymorphism at the base number position 1648 of the glycoprotein Ia gene;
(2) a polymorphism at the base number position 190 of the chemokine receptor 2 gene;
(3) a polymorphism at the base number position 1100 of the apolipoprotein C-III gene; and
(4) a polymorphism at the base number position 825 of G-protein β3 subunit gene.

[2] A method for detecting the genotype in a nucleic acid sample, the method comprising the following step (b):
(b) analyzing two or more polymorphisms selected from the group consisting of the following (5) to (8) in a nucleic acid sample:
(5) a polymorphism at the base number position −850 of the tumor necrosis factor-α gene;
(6) a polymorphism at the base number position −238 of the tumor necrosis factor-α gene;
(7) a polymorphism at the base number position 3494 of the insulin receptor substrate-1 gene; and
(8) a polymorphism at the base number position 1018 of the glycoprotein Ibα gene.

[3] A method for diagnosing the risk for hypertension, comprising the following steps (i) to (iii):
(i) analyzing two or more polymorphisms selected from the group consisting of the following (1) to (4) in a nucleic acid sample:
(1) a polymorphism at the base number position 1648 of the glycoprotein Ia gene;
(2) a polymorphism at the base number position 190 of the chemokine receptor 2 gene;
(3) a polymorphism at the base number position 1100 of the apolipoprotein C-III gene; and
(4) a polymorphism at the base number position 825 of G-protein β3 subunit gene.
(ii) determining, based on the information about polymorphism which was obtained in the step (i), the genotype in the nucleic acid sample; and
(iii) assessing, based on the genotype determined, a genetic risk for hypertension.

[4] A method for diagnosing the risk for hypertension, comprising the following steps (iv) to (vi):
(iv) analyzing two or more polymorphisms selected from the group consisting of the following (5) to (8) in a nucleic acid sample:
(5) a polymorphism at the base number position −850 of the tumor necrosis factor-α gene;
(6) a polymorphism at the base number position −238 of the tumor necrosis factor-α gene;
(7) a polymorphism at the base number position 3494 of the insulin receptor substrate-1 gene; and
(8) a polymorphism at the base number position 1018 of the glycoprotein Iba gene.
(v) determining, based on the information about polymorphism which was obtained in the step (iv), the genotype in the nucleic acid sample; and
(vi) assessing, based on the genotype determined, a genetic risk for hypertension.

[5] A kit for detecting the genotype, comprising two or more of nucleic acids selected from the group consisting of the following (1) to (4):
(1) a nucleic acid for analyzing a polymorphism at the base number position 1648 of the glycoprotein Ia gene;
(2) a nucleic acid for analyzing a polymorphism at the base number position 190 of the chemokine receptor 2 gene;
(3) a nucleic acid for analyzing a polymorphism at the base number position 1100 of the apolipoprotein C-III gene; and
(4) a nucleic acid for analyzing a polymorphism at the base number position 825 of G-protein β3 subunit gene.

[6] A kit for detecting the genotype, comprising two or more of nucleic acids selected from the group consisting of the following (5) to (8):
(5) a nucleic acid for analyzing a polymorphism at the base number position −850 of the tumor necrosis factor-α gene;
(6) a nucleic acid for analyzing a polymorphism at the base number position −238 of the tumor necrosis factor-α gene;
(7) a nucleic acid for analyzing a polymorphism at the base number position 3494 of the insulin receptor substrate-1 gene; and
(8) a nucleic acid for analyzing a polymorphism at the base number position 1018 of the glycoprotein Iba gene.

[7] Fixed nucleic acids comprising the following two or more nucleic acids selected from the group consisting of the following (1) to (4) fixed to an insoluble support:
(1) a nucleic acid for analyzing a polymorphism at the base number position 1648 of the glycoprotein Ia gene;
(2) a nucleic acid for analyzing a polymorphism at the base number position 190 of the chemokine receptor 2 gene;
(3) a nucleic acid for analyzing a polymorphism at the base number position 1100 of the apolipoprotein C-III gene; and
(4) a nucleic acid for analyzing a polymorphism at the base number position 825 of G-protein β3 subunit gene.

[8] Fixed nucleic acids comprising the following two or more nucleic acids selected from the group consisting of the following (5) to (8) fixed to an insoluble support:
(5) a nucleic acid for analyzing a polymorphism at the base number position −850 of the tumor necrosis factor-α gene;
(6) a nucleic acid for analyzing a polymorphism at the base number position −238 of the tumor necrosis factor-α gene;
(7) a nucleic acid for analyzing a polymorphism at the base number position 3494 of the insulin receptor substrate-1 gene; and
(8) a nucleic acid for analyzing a polymorphism at the base number position 1018 of the glycoprotein Iba gene.

BRIEF DESCRIPTION OF THE DRAWINGS

FIG. 1 is a table summarizing 112 gene polymorphisms examined in a screening association study in Examples.

FIG. 2 is also a table summarizing 112 gene polymorphisms examined in a screening association study in Examples.

FIG. 3 is a table summarizing primers (SEQ ID NOs: 16, 17, 18, 14, 15, 11, 12, 13, 8, 9, 10, 19, 20, 21, 22, 23, 24, 25, 26, 27, 28, 29 and 30 in this order from the top), probes (SEQ ID NOs: 31, 32, 33 and 34 in this order from the top) and other conditions used to determine the genotype in Examples. In FIG. 3, FITC denotes fluorescein isothiocyanate, TxR denotes Texas Red and Biotin denotes biotin, respectively.

FIG. 4 is a table summarizing single nucleotide polymorphisms examined in an association study in Examples.

FIG. 5 is a table summarizing the background data of 1107 lesions in men and 833 lesions in women examined in an association study in Examples. Each data of age, body mass index, systolic blood pressure, diastolic blood pressure, and serum creatinine is represented by means±standard deviation. In table, *1 denotes P<0.0001, *2 denotes P<0.001, and *3 denotes P<0.01, respectively.

FIG. 6 is a table summarizing gene polymorphisms and results of multivariate logistic regression analysis examined in the association study. In each SNP, smaller P value is expressed in boldface.

FIG. 7 is a view showing a distribution of genotype of gene polymorphisms associated with hypertension.

FIG. 8 is a table showing results of stepwise forward selection method of multivariate logistic regression analysis of gene polymorphisms associated with hypertension.

FIG. 9 is a table showing results of diagnosis of genetic risk for hypertension using a combination of four gene polymorphisms in men.

FIG. 10 is a table showing results of diagnosis of genetic risk for hypertension using a combination of four gene polymorphisms in women.

FIG. 11 is a graph showing a correlation between the cumulative odds ratio for hypertension and the number of single nucleotide polymorphisms. (A) shows the correlation in men and (B) shows the correlation in women. In (A), SNPs include: SNP1: GPIa (1648A→G) polymorphism, SNP 2: CCR2 (190G→A) polymorphism, SNP3: ApoC-III (1100C→T) polymorphism, and SNP4: GPβ3 (825C→T) polymorphism. In (B), SNPs include: SNP1: TNFa (−850C→T) polymorphism, SNP2: TNFa (−238G→A) polymorphism, SNP3: IRS-1 (3494G→A) polymorphism, and SNP4: GPIba (1018C→T) polymorphism.

BEST MODE FOR CARRYING OUT THE INVENTION

The first aspect of the present invention relates to a method of detecting the genotype in a nucleic acid sample. One embodiment of the present invention is featured by including the step of analyzing two or more polymorphisms selected from the group consisting of the following (1) to (4). Another embodiment is featured by including the step of analyzing two or more polymorphisms selected from the group consisting of the following (5) to (8). Note here that it is possible to determine, based on the information about polymorphisms which was obtained in the above-mentioned step, the genotype in the nucleic acid sample, and thereby to assess, based on the genotype determined, a genetic risk for hypertension.

(1) a polymorphism at the base number position 1648 of the glycoprotein Ia gene: 1648A→G (hereinafter, also referred to as "GPIa (1648A→G) polymorphism")

(2) a polymorphism at the base number position 190 of the chemokine receptor 2 gene: 190G→A (hereinafter, also referred to as "CCR2 (190G→A) polymorphism")

(3) a polymorphism at the base number position 1100 of the apolipoprotein C-III gene: 1100C→T (hereinafter, also referred to as "ApoC-III (1100C→T) polymorphism")

(4) a polymorphism at the base number position 825 of G-protein β3 subunit gene: 825C→T (hereinafter, also referred to as "GPβ3 (825C→T) polymorphism")

(5) a polymorphism at the base number position −850 of the tumor necrosis factor-α gene: −850C→T (hereinafter, also referred to as "TNFa (−850C→T) polymorphism")

(6) a polymorphism at the base number position −238 of the tumor necrosis factor-α gene: −238G→A (hereinafter, also referred to as "TNFa (−238G→A) polymorphism")

(7) a polymorphism at the base number position 3494 of the insulin receptor substrate-1 gene: 3494G→A (hereinafter, also referred to as "IRS-1 (3494G→A) polymorphism")

(8) a polymorphism at the base number position 1018 of the glycoprotein Iba gene: 1018C→T (hereinafter, also referred to as "GPIba (1018C→T) polymorphism")

In the above, description such as 1648A→G means that polymorphism at the relevant base number position consists of two genotypes, bases before and after the arrow.

The base number of each gene is expressed using as standards the known sequences which are registered in the public database, GenBank (NCBI). Note here that in the base sequence of SEQ ID NO: 1 (Accession No. X17033 M28249: Human mRNA for integrin alpha-2 subunit), the 1648th base corresponds to the base at position 1648 of the glycoprotein Ia gene. Similarly, in the base sequence of SEQ ID NO: 2 (Accession No. U95626: *Homo sapiens* ccr2b (ccr2), ccr2a (ccr2), ccr5 (ccr5) and ccr6(ccr6) genes, complete cds, and lactoferrin (lactoferrin) gene, partial cds, complete sequence (wherein, sequence of SEQ ID NO: 2 is a sequence to 50,000th base sequence)), the 46295th base corresponds to the base at position 190 of the chemokine receptor 2 gene; in the base sequence of SEQ ID NO: 3 (Accession No. X01392: Human apolipoprotein CIII gene and apo AI-apo CIII intergenic), the 1100th base corresponds to the base at position 1100 of the apolipoprotein C-III gene; in the base sequence of SEQ ID NO: 4 (Accession No. M31328: Human guanine nucleotide-binding protein beta-3 subunit mRNA, complete cds.), the 831st base corresponds to the base at position 825 of the G-protein β3 subunit gene; in the base sequence of SEQ ID NO: 5 (Accession No. L11698: *Homo sapiens* tumor necrosis factor alpha gene, promoter region.), the 203rd base corresponds to the base at position −850 of the tumor necrosis factor a gene; in the sequence of SEQ ID NO: 5 (Accession No. L11698: *Homo sapiens* tumor necrosis factor alpha gene, promoter region.), the 816th base corresponds to the base at position −238 of the tumor necrosis factor a gene; in the sequence of SEQ ID NO: 6 (Accession No. S85963: hIRS-1=rat insulin receptor substrate-1 homolog [human, cell line FOCUS, Genomic, 6152 nt]), the 3494th base corresponds to the base at position 3494 of the insulin receptor substrate-1 gene; and in the sequence of SEQ ID NO: 7 (Accession No. J02940: Human platelet glycoprotein Ib alpha chain mRNA, complete cds.), the 524th base corresponds to the base at position 1018 of the glycoprotein Iba gene.

In the present invention, "analyzing polymorphism" means the investigation as to what genotype a nucleic acid sample has in the gene polymorphism to be analyzed. It is the same meaning as the investigation on the base (base sequence) of the position in which the polymorphism exists. Typically, for example, in the case of the analysis of the GPIa (1648A→G) polymorphism, it refers to investigation on what genotype, i.e., AA (the base at position 1648 is a homozygote of allele A), AG (the base at position 1648 is a heterozygote of allele A and allele G) and GG (the base at position 1648 is a homozygote of allele G), the glycoprotein Ia gene in a nucleic acid sample has.

As shown in Examples mentioned below, the polymorphisms mentioned (1) to (4) above are polymorphisms that are recognized as being particularly effective to be used in determining genetic risk for hypertension in an analysis of Japanese male subjects. Therefore, analysis targeting these polymorphisms enables diagnosis with higher accuracy and with higher predictability when subjects are men (particularly, Japanese men).

Similarly, as shown in Examples mentioned below, the polymorphisms mentioned (5) to (8) above are polymorphisms that are recognized as being particularly effective to be used in determining genetic risk for hypertension in an analysis of Japanese female subjects. Therefore, analysis targeting these polymorphisms enables diagnosis with higher accuracy and with higher predictability when subjects are women (particularly, Japanese women).

Herein, in principle, in proportion to the increase in the number of polymorphisms to be analyzed, the genotypes of nucleic acid sample are classified more finely. Thereby, it is possible to diagnose a genetic risk for hypertension with higher predictability. From this viewpoint, it is preferable to detect the genotype by analyzing a larger number of polymorphisms in the above-mentioned polymorphisms (1) to (4). Therefore, it is the most preferable to analyze all of the polymorphisms (1) to (4). In the case where detection is carried out by combining three or less of polymorphisms, it is preferable to preferentially select the polymorphisms with higher odds ratios as in Examples mentioned below. For example, in the case where three polymorphisms are used in combination, it is preferable to select three polymorphisms with higher odds ratio, that is, to select (2), (3) and (4). Similarly, in the case where two polymorphisms are used in combination, it is preferable to select (2) and (4).

Similarly, in the case where two or more polymorphisms selected from the group consisting of polymorphisms (5) to (8), it is most preferable to analyze all these polymorphisms, that is, four polymorphisms. In the case where detection is carried out by combining three or less of polymorphisms, it is preferable to preferentially select the polymorphisms with higher odds ratios in Examples mentioned below. For example, in the case where three polymorphisms are used in combination, it is preferable to select (5), (7) and (8). Similarly, in the case where two polymorphisms are used in combination, it is preferable to select (5) and (7).

A method for analyzing each genetic polymorphism is not particularly limited and known method can be employed. The known methods may include, for example, amplification by PCR using an allele-specific primer (and probe), a method for analyzing polymorphism of amplified product by means of fluorescence or luminescence; a method using a PCR (polymerase chain reaction) method including a PCR-RFLP (polymerase chain reaction-restriction fragment length polymorphism) method, a PCR-SSCP (polymerase chain reaction-single strand conformation polymorphism) method (Orita, M. et al., Proc. Natl. Acad. Sci., U.S.A., 86, 2766-2770 (1989), etc.), and a PCR-SSO (specific sequence oligonucleotide) method, an ASO (allele specific oligonucleotide) hybridization method combining the PCR-SSO method and a dot hybridization method (Saiki, Nature, 324, 163-166 (1986), etc.), or a TaqMan-PCR method (Livak, K J, Genet Anal, 14, 143 (1999), Morris, T. et al., J. Clin. Microbiol., 34, 2933 (1996)), an Invader method (Lyamichev V et al., Nat Biotechnol, 17, 292 (1999)), a MALDI-TOF/MS (matrix) method using a primer extension method (Haff L A, Smirnov I P, Genome Res 7, 378 (1997)), a RCA (rolling cycle amplification) method (Lizardi P M et al., Nat Genet 19, 225 (1998)), a method using DNA microchip or micro-array (Wang D G et al., Science 280, 1077 (1998), etc.)), a primer extension method, a Southern blot hybridization method, a dot hybridization method (Southern, E., J. Mol. Biol. 98, 503-517 (1975)), etc.), or the like. Furthermore, an analysis may be made by direct sequencing of the portion of polymorphism which is subject to analysis. Note here that polymorphisms may be analyzed by combining these methods ad libitum.

In the case where the amount of nucleic acid sample is small, it is preferable to analyze it by a method using PCR (for example, PCR-RFLP method) from the viewpoint of detection sensitivity or accuracy. Furthermore, any of the above-mentioned analysis methods may be employed after nucleic acid sample is amplified in advance (including a partial region of nucleic acid sample) by a gene amplification such as PCR method or a method applying PCR method.

Meanwhile, in the case where a large number of nucleic acid samples are analyzed, it is particularly preferable to employ a method capable of analyzing a large number of samples in a relatively short period of time, for example, allele-specific PCR method, allele-specific hybridization method, TaqMan-PCR method, Invader method, MALDI-TOF/MS (matrix) method using a primary extension method, RCA (rolling cycle amplification) method, a method using a DNA chip or a micro-array, or the like.

The above methods use nucleic acids (also called "nucleic acid for analyzing polymorphism" in the present invention), e.g., primer and probe, in accordance with each method. An example of the nucleic acids for analyzing polymorphism may include a nucleic acid having a sequence complementary to a given region including the site of polymorphism (partial DNA region) in a gene which contains polymorphism to be analyzed, and a nucleic acid (primer) which has a sequence complementary to a given region including the site of polymorphism (partial DNA region) in a gene which contains polymorphism to be analyzed and which is designed to specifically amplify the DNA fragment containing the relevant site of polymorphism. In the case where polymorphism at position 1648 of the glycoprotein Ia gene is a subject to be analyzed, an example of such nucleic acids includes a nucleic acid having a sequence complementary to a partial DNA region including the position 1648 of the glycoprotein Ia gene whose base at position 1648 is A (adenine), or a nucleic acid having a sequence complementary to a partial DNA region including the position 1648 of the glycoprotein Ia gene whose base at position 1648 is G (guanine).

Other concrete examples of nucleic acids for analyzing polymorphism may include a set of nucleic acids which is designed to specifically amplify the partial DNA region that contains the relevant site of polymorphism only in the case where the site of polymorphism to be analyzed is a certain genotype. A more concrete example may include a set of nucleic acids which is designed to specifically amplify the partial DNA region including the site of polymorphism to be analyzed and which consists of a sense primer that specifically hybridizes the partial DNA region including the relevant site of polymorphism in an antisense strand whose site of polymorphism is a certain genotype and of an antisense primer that specifically hybridizes a partial region in the sense strand. In the case where a subject to the analysis is a polymorphism at position 1648 of the glycoprotein Ia gene, examples of such a set of nucleic acids include a set of nucleic acids which is designed to specifically amplify the partial DNA region including the base at position 1648 of the glycoprotein Ia gene and which consists of a sense primer that specifically hybridizes the partial DNA region containing the base at position 1648 in the antisense strand of the glycoprotein Ia gene whose base at position 1648 is A (adenine) and of an antisense primer that specifically hybridizes a partial region in the sense strand; or a set of nucleic acids which consists of a sense primer that specifically hybridizes the partial DNA region including the base at position 1648 in the antisense strand of the glycoprotein Ia gene whose base at position 1648 is G (guanine) and of an antisense primer that specifically hybridizes a partial region in the sense strand. The length of the partial DNA region to be amplified here is set accordingly in a range which is appropriate for its detection, and is for example, 50 bp to 200 bp, and preferably 80 bp to 150 bp. A more concrete example may include a set of nucleic acid primers for analyzing the GPIa (1648A→G) polymorphism containing the following sequences. Note here that an underlined part in the following sequences means a part corresponding to the polymorphism. Furthermore, in the sequence, N denotes any of A, T, C and G.

```
sense primer
GAGTCTACCTGTTTACTATCAANAA:,      SEQ ID NO: 8
or

GAGTCTACCTGTTTACTATCAANGA:       SEQ ID NO: 9 antisense primer
ACCAGTACTAAAGCAAATTAAACT:        SEQ ID NO: 10
```

Similarly, an example of a nucleic acid primer for analyzing the CCR2 (190G→A) polymorphism may include a set containing the following sequences.

```
antisense primer
GCAGTTTATTAAGATGAGGNCG:,         SEQ ID NO: 11
or

TTGCAGTTTATTAAGATGAGGNTG:        SEQ ID NO: 12 sense primer
GGTGCTCCCTGTCATAAATTTGA:         SEQ ID NO: 13
```

Similarly, an example of a nucleic acid primer for analyzing the ApoC-III (1100C→T) polymorphism may include a set containing the following sequences.

```
sense primer
CCTTCTCAGCTTCATGCAGG:,           SEQ ID NO: 14 antisense primer
GTCTTGGTGGCGTGCTTCA:             SEQ ID NO: 15
```

Similarly, an example of a nucleic acid primer for analyzing the GPβ3 (825C→T) polymorphism may include a set containing the following sequences.

```
sense primer
TCTGCGGCATCACGTNCG:,             SEQ ID NO: 16
or

TCTGCGGCATCACGTNTG:              SEQ ID NO: 17 antisense primer
GAATAGTAGGCGGCCACTGA:            SEQ ID NO: 18
```

Similarly, an example of a nucleic acid primer for analyzing the TNFa (−850C→T) polymorphism may include a set containing the following sequences.

```
antisense primer
TCTACATGGCCCTGTCTTNGT:,          SEQ ID NO: 19
or

CTCTACATGGCCCTGTCTTNAT:          SEQ ID NO: 20 sense primer
CTCTACATGGCCCTGTCTTTAT:          SEQ ID NO: 21
```

Similarly, an example of a nucleic acid primer for analyzing the TNFa (−238G→A) polymorphism may include a set containing the following sequences.

```
antisense primer
CCCCATCCTCCCTGCTNCG:,            SEQ ID NO: 22
or

CCCCATCCTCCCTGCTNTG:             SEQ ID NO: 23 sense primer
AGTCAGTGGCCCAGAAGACC:            SEQ ID NO: 24
```

Similarly, an example of a nucleic acid primer for analyzing the IRS-1 (3494G→A) polymorphism may include a set containing the following sequences.

```
sense primer
GGGCCCTGCACCTCCNGG:,             SEQ ID NO: 25
or

GGGCCCTGCACCTCCNAG:              SEQ ID NO: 26 antisense primer
GGGTAGGCCTGCAAATGCTA:            SEQ ID NO: 27
```

Similarly, an example of a nucleic acid primer for analyzing the GPIba (1018C→T) polymorphism may include a set containing the following sequences.

```
sense primer
CCCAGGGCTCCTGNCG:,               SEQ ID NO: 28
or

CCCCAGGGCTCCTGNTG:               SEQ ID NO: 29 antisense primer
TGAGCTTCTCCAGCTTGGGTG:           SEQ ID NO: 30
```

On the other hand, a concrete example of the probe can include:

as a probe for analyzing ApoC-III (1100C→T) polymorphism,

CAGCTTCATGCAGGGCTACA: SEQ ID NO: 31, or

CAGCTTCATGCAGGGTTACA: SEQ ID NO: 32 as a probe for analyzing TNFa (−850C→T) polymorphism,

ACATGGCCCTGTCTTNGTTAAG: SEQ ID NO: 33, or

ACATGGCCCTGTCTTNATTAAG: SEQ ID NO: 34 as a probe for analyzing IRS-1 (3494G→A) polymorphism,

CACCTCCNGGGGCTGCTAG: SEQ ID NO: 35, or

CACCTCCNAGGGCTGCTAG: SEQ ID NO: 36

The above nucleic acid primers and nucleic acid probes are mere examples. Nucleic acid primers may contain a partially modified base sequence as long as they can carry out the aimed amplification reaction without inconvenience, while nucleic acid probes may contain a partially modified base sequence as long as they can carry out the aimed hybridization reaction without inconvenience. "Partially modified" herein means that a part of bases is deleted, replaced, inserted, and/or added. The numbers of bases to be modified are, for example, one to seven, preferably one to five, and more preferably one to three. Note here that such a modification is made in the portions other than bases corresponding to the site of polymorphism, in principle.

As nucleic acids (probes or primers) for analyzing polymorphism, DNA fragments or RNA fragments are used accordingly in response to the analysis method employed. The base length of nucleic acids for analyzing polymorphism may be sufficient if it exerts respective functions of each nucleic acid. Base lengths in the case of use as primers are, for example, 10 bp to 50 bp, preferably 15 bp to 40 bp, and more preferably 15 bp to 30 bp.

Note here that in the case of use as primers, some mismatches to the sequence which constitutes the template may be admitted as long as the primer can specifically hybridize the subject for amplification and amplify the target DNA fragment. In the case of probes, some mismatches to the sequence which is subject to detection may be similarly admitted as long as the probe can specifically hybridize the sequence which is subject to detection. The numbers of mismatches are one to several, preferably one to five, and more preferably one to three.

Nucleic acids (primers and probes) for analyzing polymorphism can be synthesized in accordance with known methods, e.g., phosphodiester method. Note here that textbooks (e.g., Molecular Cloning, Third Edition, Cold Spring Harbor Laboratory Press, New York) can be referred with respect to design, synthesis, and others of nucleic acids for analyzing polymorphism.

Nucleic acids for analyzing polymorphism in the present invention can be labeled with labeling substances in advance. The use of such labeled nucleic acids allows, for example, the analysis of polymorphism by using the labeling amount in the product of amplification as a marker. Furthermore, by labeling two kinds of primers which were designed specifically amplify the partial DNA region in the gene of each genotype that constitute polymorphism with labeling substances that are different from each other, the genotype in a nucleic acid sample can be discriminated according to the labeling substance and labeling amount to be detected based on the product of amplification. Concrete examples of detection methods using these labeled primers may include: a method for detecting polymorphism, which includes labeling, with fluorescein isothiocyanate and Texas red, two kinds of nucleic acid primers (allele-specific sense primers) that respectively and specifically hybridize the sense strand of each genotype constituting polymorphism; amplifying the partial DNA region including the site of polymorphism by using these labeled primers and the antisense primers that specifically hybridize the antisense strand; and measuring the labeling amount of each fluorescent substance in the product of amplification obtained. Note here that labeling of the antisense primer herein with, for example, biotin allows the separation of the product of amplification by utilizing the specific binding between biotin and avidin.

Radioactive isotopes, for example, $^{32}P$, and fluorescent substance, for example, fluorescein isothiocyanate, tetramethylrhodamine isothiocyanate, and Texas red, etc. can be exemplified as labeling substances to be used in labeling nucleic acids for analyzing polymorphism. The 5' terminal labeling method using alkaline phosphatase and T4 polynucleotide kinase, the 3' terminal labeling method using T4 DNA polymerase and Klenow fragment, nicktranslation method, random primer method (Molecular Cloning, Third Edition, Chapter 9, Cold Spring Harbor Laboratory Press, New York), and the like can be exemplified as labeling methods.

The above-mentioned nucleic acids for analyzing polymorphism can be used also under a condition fixed to an insoluble support. Processing of an insoluble support to be used for the fixation to several forms such as chips and beads allows the more simplified analysis of polymorphism by using these fixed nucleic acids.

A nucleic acid sample can be prepared from blood, skin cells, mucous cells, hair, and others from the subject according to known extraction methods and purification methods. In the case of including the gene which is subject to the analysis of polymorphism, the genome DNA of arbitrary length can be used as a nucleic acid sample. Furthermore, it is not necessary to use a nucleic acid sample in which all genes subject to the analysis are present on one nucleic acid. That is to say, as a nucleic acid sample of the present invention, both material in which all genes subject to the analysis are present on one nucleic acid and material in which genes subject to the analysis are present separately on two or more nucleic acids can be used. Note here that material in a fragmented or partial condition may be accepted as long as the site of polymorphism to be analyzed is at least present, although genes subject to the analysis in a nucleic acid sample are not in a complete condition (i.e., a condition in which the full length of the gene is present).

Analysis of each gene polymorphism is carried out each by each of the gene polymorphism, or a plurality or entire gene polymorphisms are carried out simultaneously. In the former case, for example, nucleic acid sample collected from the subjects is divided in accordance with the number of polymorphisms to be analyzed, and analysis of polymorphism is carried out individually. In the latter case, for example, analysis of polymorphism can be carried out by DNA chip or micro-array. Note here that "simultaneously" herein not only imply that all operations of the analysis process are conducted simultaneously but also include the case in which part of operations (e.g., operation to amplify nucleic acid, hybridization or detection of the probe) is conducted simultaneously.

Polymorphism of each gene can be analyzed by using mRNA which is a product of transcription of the gene which is subject to the analysis. After extracting and purifying mRNA of the gene, which is subject to the analysis, from blood, urine, and others of the subject, for example, polymorphism can be analyzed with mRNA as a starting material by conducting methods, e.g., Northern blotting method (Molecular Cloning, Third Edition, 7.42, Cold Spring Harbor Laboratory Press, New York), dot blotting method (Molecular Cloning, Third Edition, 7.46, Cold Spring Harbor Laboratory Press, New York), RT-PCR method (Molecular Cloning, Third Edition, 8.46, Cold Spring Harbor Laboratory Press, New York), and methods using the DNA chip (DNA array), and the like.

In addition, in the above-mentioned polymorphism, polymorphism involved with changes in amino acids can be analyzed by using the expression product of gene that is a subject to analysis. In this case, material, even if it is partial protein or partial peptide, can be used as a sample for analysis as long as it contains amino acids which correspond to the site of polymorphism.

Analysis methods using these expression products of gene may include: a method for directly analyzing amino acids at the site of polymorphism, a method for immunologically analyzing utilizing changes of three-dimensional structure, or the like. As the former method, a well-known amino acid sequence analysis method (a method using Edman method) can be used. As the latter method, ELISA (enzyme-linked immunosorbent assay) using a monoclonal antibody or polyclonal antibody which has binding activity specific to the expression product of gene which has any of genotypes that constitute polymorphism; radioimmunoassay, immunoprecipitation method, immunodiffusion method, and the like, can be used.

Information about polymorphisms to be obtained by conducting the detection methods of the present invention described above can be used to diagnose a genetic risk for hypertension. That is to say, the present invention also provides a method for diagnosing a genetic risk for hypertension, which includes a step of determining the genotype in a nucleic acid sample based on information about polymorphisms obtained by the above-detection methods, and a step of assessing a genetic risk for hypertension based on the determined genotype in the nucleic acid sample. Herein, the determination of the genotype is typically to determine which genotype both alleles of nucleic acid samples have with respect to the polymorphism to be detected. In the case where the subject to be detected is, for example, GPIa (1648A→G) polymorphism, the detection of genotype is typically, an investigation on what genotype from AA (the base at position 1648 is a homozygote of allele A), AG (the base at position 1648 is a heterozygote of allele A and allele G) and GG (the base at position 1648 is a homozygote of allele G), the GPIa gene has in a nucleic acid sample.

By considering the results obtained in Example mentioned below, in order to enable a diagnosis of genetic risk for hypertension with high accuracy and high predictability, for example, in the case of the GPIa (1648A→G) polymorphism, it is determined whether the genotype in a nucleic acid sample is GG or, AA or AG. Similarly, in the case of the CCR2 (190G→A) polymorphism, it is determined whether the genotype is AA, or GG or GA; in the case of the ApoC-III (1100C→T) polymorphism, it is determined whether the genotype is TT, or CC or CT; in the case of the GPβ3 (825C→T) polymorphism, it is determined whether the genotype is CT or TT, or CC; in the case of the TNFa (−850C→T) polymorphism, it is determined whether the genotype is TT, or CC or CT; in the case of TNFa (−238G→A) polymorphism, it is determined whether the genotype is GA or AA, or GG; in the case of IRS-1 (3494G→A) polymorphism, it is determined whether the genotype is GA or AA, or GG; and in the case of GPIba (1018C→T) polymorphism, it is determined whether the genotype is CT or TT, or CC.

Diagnosis of a genetic risk for hypertension enables prediction of potentiality (likelihood of development) in that hypertension might be developed in future, that it to say, development risk (susceptibility to development). Furthermore, it becomes possible to carry out the recognition of hypertension based on the genotype that is an objective index or to understand conditions of the disease. In other words, the diagnosis method of the present invention makes it possible to evaluate the risk of development of hypertension, to recognize the development of hypertension, or to understand conditions of the disease. It is clinically significant that it is possible to assess the risk of development because having knowledge about the development risk in advance contributes to primary prevention of hypertension so as to makes it possible to take an appropriate prevention.

The information obtained by the diagnosis method of the present invention can be used for selecting an appropriate treatment, improvement of prognosis, improvement of QOL (quality of life) of patients, reduction of the risk of development, or the like.

By conducting the diagnosis method of the present invention, it is possible to monitor the development risk for hypertension, etc. As a result of such monitoring, when correlation between certain external factors (environment factor, administration of drugs, and the like) and the increase in the risk of development is found, the relevant external factors are recognized as risk factors and it can be thought that based on such information, the development risk etc. can be reduced.

The genetic information associated with the development of hypertension obtained by the present invention can be used for treatment of hypertension (including preventive treatment). For example, as a result of carrying out the diagnostic method of the present invention, when the polymorphism to be analyzed is a genotype to increase the risk of development of hypertension, by introducing a gene having a genotype with low risk of development into a living body and allowing the gene to express, the reduction of disease, suppression of development and reduction of development risk, and the like can be expected due to the expression of the gene. The same treatment effect can be expected by a method of introducing antisense strand with respect to mRNA of gene having a genotype with high risk of development and suppressing the expression of the mRNA.

The introduction of genes or antisense strand can be carried out by a method, for example, a method using a plasmid for gene introduction or a virus vector, electroporation (Potter, H. et al., Proc. Natl. Acad. Sci. U.S.A. 81, 7161-7165(1984)), an ultrasonic micro bubble (Lawrie, A., et al. Gene Therapy 7, 2023-2027 (2000)), lipofection (Felgner, P. L. et al., Proc. Natl. Acad. Sci. U.S.A. 84, 7413-7417 (1984)), microinjection (Graessmann, M. & Graessmann, A., Proc. Natl. Acad. Sci. U.S.A. 73,366-370(1976)), and the like. By utilizing these methods, desired genes, etc. can be directly introduced (in vivo method) or indirectly introduced (ex vivo method).

The second aspect of the present invention provides a kit (a kit for detecting the genotype or a kit for diagnosing hypertension) to be used in the above-mentioned detecting method or diagnostic method in the present invention. Such a kit contains nucleic acids (nucleic acids for analyzing polymorphism) for analyzing two or more polymorphisms selected from the group consisting of polymorphisms described in (1) to (4) above. As another embodiment, such a kit is constructed, which contains nucleic acids (nucleic acids for analyzing polymorphism) for analyzing two or more polymorphisms selected from the group consisting of polymorphisms described in (5) to (8) above.

Nucleic acids for analyzing polymorphism are designed as materials which can specifically amplifies (primer) or specifically detect (probe) the DNA region containing the polymorphism portion to be analyzed or mRNA which corresponds to the region in the analysis methods to be applied (a method which utilizes PCR using the above-mentioned allele-specific nucleic acids and the like, PCR-RFLP method, PCR-SSCP method, TaqMan-PCR method, Invader method, etc.). Concrete examples of kits to be provided according to the present invention are described below.

A kit for detecting the genotype, comprising two or more nucleic acids selected from the group consisting of the following (1) to (4):

(1) a nucleic acid having a sequence which is complementary to the partial DNA region containing the base at position 1648 of the glycoprotein Ia gene whose base at position 1648 is A, or a nucleic acid having a sequence which is complementary to the partial DNA region containing the base at position 1648 of the glycoprotein Ia gene whose base at position 1648 is G;

(2) a nucleic acid having a sequence which is complementary to the partial DNA region containing the base at position 190 of the chemokine receptor 2 gene whose base at position 190 is G, or a nucleic acid having a sequence which is complementary to the partial DNA region containing the base at position 190 of the chemokine receptor 2 gene whose base at position 190 is A;

(3) a nucleic acid having a sequence which is complementary to the partial DNA region containing the base at position 1100 of the apolipoproteins C-III gene whose base at position 1100 is C, or a nucleic acid having a sequence which is complementary to the partial DNA region containing the base at position 1100 of the apolipoproteins C-III gene whose base at position 1100 is T; and (4) a nucleic acid having a sequence which is complementary to the partial DNA region containing the base at position 825 of the G-protein β3 subunit gene whose base at position 825 is C, or a nucleic acid having a sequence which is complementary to the partial DNA region containing the base at position −482 of the G-protein β3 subunit gene whose base at position 825 is T.

In the above mention, kits are constructed by selecting two or more nucleic acids from the group consisting of (1) to (4). However, kits may be constructed by making a group consisting of two or more nucleic acids arbitrarily selected from (1) to (4) and selecting two or more nucleic acids from such a group. For example, kits may be constructed by selecting two or more nucleic acids from the group consisting of (2) to (4) (nucleic acids for analyzing polymorphisms with three highest odds ratio).

A kit for detecting the genotype, comprising two or more nucleic acids selected from the group consisting of the following (5) to (8):

(5) a nucleic acid having a sequence which is complementary to the partial DNA region containing the base at position −850 of the tumor necrosis factor-α gene whose base at position −850 is C, or a nucleic acid having a sequence which is complementary to the partial DNA region containing the base at position −850 of the tumor necrosis factor-α gene whose base at position −850 is T;

(6) a nucleic acid having a sequence which is complementary to the partial DNA region containing the base at position −238 of the tumor necrosis factor-α gene whose base at position −238 is Q or a nucleic acid having a sequence which is complementary to the partial DNA region containing the base at position −238 of the tumor necrosis factor-α gene whose base at position −238 is A;

(7) a nucleic acid having a sequence which is complementary to the partial DNA region containing the base at position 3494 of the insulin receptor substrate-1 gene whose base at position 3494 is G, or a nucleic acid having a sequence which is complementary to the partial DNA region containing the base at position 3494 of the insulin receptor substrate-1 gene whose base at position 3494 is A; and (8) a nucleic acid having a sequence which is complementary to the partial DNA region containing the base at position 1018 of the glycoprotein Ibα gene whose base at position 1018 is C, or a nucleic acid having a sequence which is complementary to the partial DNA region containing the base at position 1018 of the glycoprotein Ibα gene whose base at position 1018 is T.

In the above mention, kits are constructed by selecting two or more nucleic acids from the group consisting of (5) to (8). However, kits may be constructed by making a group consisting of two or more nucleic acids arbitrarily selected from (5) to (8) and selecting two or more nucleic acids from such a group. For example, kits may be constructed by selecting two or more nucleic acids from the group consisting of (5), (7) and (8) (nucleic acids for analyzing polymorphisms with three highest odds ratios in Example mentioned below).

A kit for detecting the genotype, comprising two or more sets of nucleic acids selected from the group consisting of the following (1) to (4):

(1) a set of nucleic acids which is designed to specifically amplify the partial DNA region containing the base at position 1648 of the glycoprotein Ia gene only in the case where the base at position 1648 of the glycoprotein Ia gene in a nucleic acid sample is A, or a set of nucleic acids which is designed to specifically amplify the partial DNA region containing the base at position 1648 of the glycoprotein Ia gene only in the case where the base at position 1648 of the glycoprotein Ia gene in a nucleic acid sample is G;

(2) a set of nucleic acids which is designed to specifically amplify the partial DNA region containing the base at position 190 of the chemokine receptor 2 gene only in the case where the base at position 190 of the chemokine receptor 2 gene in a nucleic acid sample is G, or a set of nucleic acids which is designed to specifically amplify the partial DNA region containing the base at position 190 of the chemokine receptor 2 gene only in the case where the base at position 190 of the chemokine receptor 2 gene in a nucleic acid sample is A;

(3) a set of nucleic acids which is designed to specifically amplify the partial DNA region containing the base at position 1100 of the apolipoprotein C-III gene only in the case where the base at position 1100 of the apolipoprotein C-III gene in a nucleic acid sample is C, or a set of nucleic acids which is designed to specifically amplify the partial DNA region containing the base at position 1100 of the apolipoprotein C-III gene only in the case where the base at position 1100 of the apolipoprotein C-III gene in a nucleic acid sample is T; and (4) a set of nucleic acids which is designed to specifically amplify the partial DNA region containing the base at position 825 of the G-protein β3 subunit gene only in the case where the base at position 825 of the G-protein β3 subunit gene in a nucleic acid sample is C, or a set of nucleic acids which is designed to specifically amplify the partial DNA region containing the base at position 825 of the G-protein β3 subunit gene only in the case where the base at position 825 of the G-protein β3 subunit gene in a nucleic acid sample is T.

In the above mention, kits are constructed by selecting two or more nucleic acids from the group consisting of (1) to (4). However, kits may be constructed by making a group consisting of two or more nucleic acids arbitrarily selected from (1) to (4) and selecting two or more nucleic acids from such a group. For example, kits may be constructed by selecting two or more nucleic acids from the group consisting of (2) to (4) (nucleic acids for analyzing polymorphisms with three highest odds ratio in Example mentioned below).

A kit for detecting the genotype, comprising two or more sets of nucleic acids selected from the group consisting of the following (5) to (8):

(5) a set of nucleic acids which is designed to specifically amplify the partial DNA region containing the base at position −850 of the tumor necrosis factor-α gene only in the case where the base at position −850 of the tumor necrosis factor-α gene in a nucleic acid sample is C, or a set of nucleic acids which is designed to specifically amplify the partial DNA region containing the base at position −850 of the tumor necrosis factor-α gene only in the case where the base at position −850 of the tumor necrosis factor-α gene in a nucleic acid sample is T;

(6) a set of nucleic acids which is designed to specifically amplify the partial DNA region containing the base at position −238 of the tumor necrosis factor-α gene only in the case where the base at position −238 of the tumor necrosis factor-α gene in a nucleic acid sample is G, or a set of nucleic acids which is designed to specifically amplify the partial DNA region containing the base at position −238 of the tumor necrosis factor-α gene only in the case where the base at position −238 of the tumor necrosis factor-α gene in a nucleic acid sample is A;

(7) a set of nucleic acids which is designed to specifically amplify the partial DNA region containing the base at position 3494 of the insulin receptor substrate-1 gene only in the case where the base at position 3494 of the insulin receptor substrate-1 gene in a nucleic acid sample is G, or a set of nucleic acids which is designed to specifically amplify the partial DNA region containing the base at position 3494 of the insulin receptor substrate-1 gene only in the case where the base at position 3494 of the insulin receptor substrate-1 gene in a nucleic acid sample is A; and (8) a set of nucleic acids which is designed to specifically amplify the partial DNA region containing the base at position 1018 of the glycoprotein Ibα gene only in the case where the base at position 1018 of the glycoprotein Ibα gene in a nucleic acid sample is C, or a set of nucleic acids which is designed to specifically amplify the partial DNA region containing the base at position 1018 of the glycoprotein Ibα gene only in the case where the base at position 1018 of the glycoprotein Ibα gene in a nucleic acid sample is T.

In the above mention, kits are constructed by selecting two or more nucleic acids from the group consisting of (5) to (8). However, kits may be constructed by making a group consisting of two or more nucleic acids arbitrarily selected from (5) to (8) and selecting two or more sets of nucleic acids from such a group. For example, kits may be constructed by selecting two or more nucleic acids from the group consisting of (5), (7) and (8) (nucleic acids for analyzing polymorphisms with three highest odds ratio in Example mentioned below).

A kit for detecting the genotype, comprising two or more sets of nucleic acids selected from the group consisting of the following (1) to (4):

(1) a set of nucleic acids which is designed to specifically amplify the partial DNA region containing the base at position 1648 of the glycoprotein Ia gene and which consists of a sense primer that specifically hybridizes the partial DNA region containing the base at position 1648 of the glycoprotein Ia gene whose base at position 1648 is A and/or a sense primer that specifically hybridizes the partial DNA region containing the base at position 1648 of the glycoprotein Ia gene whose gene at position 1648 is G and of an antisense primer that specifically hybridizes a partial region of the glycoprotein Ia gene;

(2) a set of nucleic acids which is designed to specifically amplify the partial DNA region containing the base at position 190 of the chemokine receptor 2 gene and which consists of an antisense primer that specifically hybridizes the partial DNA region containing the base at position 190 of the chemokine receptor 2 gene whose base at position 190 is G and/or an antisense primer that specifically hybridizes the partial DNA region containing the base at position 190 of the chemokine receptor 2 gene whose gene at position 190 is A and of a sense primer that specifically hybridizes a partial region of the chemokine receptor 2 gene;

(3) a set of nucleic acids which is designed to specifically amplify the partial DNA region containing the base at position 1100 of the apolipoprotein C-III gene; and (4) a set of nucleic acids which is designed to specifically amplify the partial DNA region containing the base at position 825 of the G-protein β3 subunit gene and which consists of a sense primer that specifically hybridizes the partial DNA region containing the base at position 825 of the G-protein β3 subunit gene whose base at position 825 is C and/or a sense primer that specifically hybridizes the partial DNA region containing the base at position 825 of the G-protein β3 subunit gene whose gene at position 825 is T and of an antisense primer that specifically hybridizes a partial region of the G-protein β3 subunit gene.

In the above mention, kits are constructed by selecting two or more nucleic acids from the group consisting of (1) to (4). However, kits may be constructed by making a group consisting of two or more nucleic acids arbitrarily selected from (1) to (4) and selecting two or more sets of nucleic acids from such a group. For example, kits may be constructed by selecting two or more nucleic acids from the group consisting of (2) to (4) (nucleic acids for analyzing polymorphisms with three highest odds ratios in Example mentioned below).

A kit for detecting the genotype, comprising two or more sets of nucleic acids selected from the group consisting of the following (5) to (8):

(5) a set of nucleic acids which is designed to specifically amplify the partial DNA region containing the base at position −850 of the tumor necrosis factor-α gene and which consists of an antisense primer that specifically hybridizes the partial DNA region containing the base at position −850 of the tumor necrosis factor-α gene whose base at position −850 is C and/or an antisense primer that specifically hybridizes the partial DNA region containing the base at position −850 of the tumor necrosis factor-α gene whose gene at position −850 is T and of a sense primer that specifically hybridizes a partial region of the tumor necrosis factor-α gene;

(6) a set of nucleic acids which is designed to specifically amplify the partial DNA region containing the base at position −238 of the tumor necrosis factor-α gene and which consists of an antisense primer that specifically hybridizes the partial DNA region containing the base at position −238 of the tumor necrosis factor-α gene whose base at position −238 is G and/or an antisense primer that specifically hybridizes the partial DNA region containing the base at position −238 of the tumor necrosis factor-α gene whose gene at position −238 is A and of a sense primer that specifically hybridizes a partial region of the tumor necrosis factor-α gene;

(7) a set of nucleic acids which is designed to specifically amplify the partial DNA region containing the base at position 3494 of the insulin receptor substrate-1 gene and which consists of a sense primer that specifically hybridizes the partial DNA region containing the base at position 3494 of the insulin receptor substrate-1 gene whose base at position 3494 is G and/or a sense primer that specifically hybridizes the partial DNA region containing the base at position 3494 of the insulin receptor substrate-1 gene whose gene at position 3494 is A and of an antisense primer that specifically hybridizes a partial region of the insulin receptor substrate-1 gene; and (8) a set of nucleic acids which is designed to specifically amplify the partial DNA region containing the base at position 1018 of the glycoprotein Ibα gene and which consists of a sense primer that specifically hybridizes the partial DNA region containing the base at position 1018 of the glycoprotein Ibα gene whose base at position 1018 is C and/or a sense primer that specifically hybridizes the partial DNA region containing the base at position 1018 of the glycoprotein Ibα gene whose gene at position 1018 is T and of an antisense primer that specifically hybridizes a partial region of the glycoprotein Ibα gene.

In the above mention, kits are constructed by selecting two or more nucleic acids from the group consisting of (5) to (8).

However, kits may be constructed by making a group consisting of two or more nucleic acids arbitrarily selected from (5) to (8) and selecting two or more sets of nucleic acids from such a group. For example, kits may be constructed by selecting two or more nucleic acids from the group consisting of (5), (7) to (8) (nucleic acids for analyzing polymorphisms with three highest odds ratio in Example mentioned below).

A kit for detecting the genotype comprising two or more sets of nucleic acids selected from the group consisting of the following (1) to (4);

(1) a set of nucleic acids which consists of a first nucleic acid that specifically hybridizes a partial region containing a base corresponding to the base at position 1648 in the antisense strand of the glycoprotein Ia gene whose base at position 1648 is A and that is labeled with a first labeling substance, of a second nucleic acid that specifically hybridizes a partial region containing a base corresponding to the base at position 1648 in the antisense strand of the glycoprotein Ia gene whose base at position 1648 is G and that is labeled with a second labeling substance, and of the third nucleic acid that specifically hybridizes a partial region in the sense strand of the glycoprotein Ia gene and that can specifically amplify the partial DNA region containing the base at position 1648 of the glycoprotein Ia gene in concurrent use with the above first or second nucleic acid;

(2) a set of nucleic acids which consists of a first nucleic acid that specifically hybridizes a partial region containing the base at position 190 in the sense strand of the chemokine receptor 2 gene whose base at position 190 is G and that is labeled with a first labeling substance, of a second nucleic acid that specifically hybridizes a partial region containing the base at position 190 in the sense strand of the chemokine receptor 2 gene whose base at position 190 is A and that is labeled with a second labeling substance, and of the third nucleic acid that specifically hybridizes a partial region in the antisense strand of the chemokine receptor 2 gene and that can specifically amplify the partial DNA region containing the base at position 190 of the chemokine receptor 2 in concurrent use with the above first or second nucleic acid;

(3) a set of nucleic acids which consists of first and second nucleic acids that are designed to specifically amplify the partial DNA region containing the base at position 1100 of the apolipoprotein C-III gene, of a third nucleic acid that specifically hybridizes the nucleic acid which is amplified by the use of the first and second nucleic acids using the apolipoprotein C-III gene in which the base at position 1100 is C as a template and which is labeled with a first labeling substance, and of a fourth nucleic acid that specifically hybridizes a nucleic acid which is amplified by the use of the first and second nucleic acids by using apolipoprotein C-III gene in which the base at position 1100 is T as a template and which is labeled with a second labeling substance; and (4) a set of nucleic acids which consists of a first nucleic acid that specifically hybridizes a partial region containing the base at position 825 in the antisense strand of the G-protein 13 subunit gene whose base at position 825 is C and that is labeled with a first labeling substance, of a second nucleic acid that specifically hybridizes a partial region containing the base at position 825 in the antisense strand of the G-protein β3 subunit gene whose base at position 825 is T and that is labeled with a second labeling substance, and of the third nucleic acid that specifically hybridizes a partial region in the sense strand of the G-protein β3 subunit gene and that can specifically hybridize the partial DNA region containing the base at position 825 of the G-protein β3 subunit gene in concurrent use with the above first or second nucleic acid.

In the above mention, kits are constructed by selecting two or more nucleic acids from the group consisting of (1) to (4). However, kits may be constructed by making a group consisting of two or more nucleic acids arbitrarily selected from (1) to (4) and selecting two or more nucleic acids from such a group. For example, kits may be constructed by selecting two or more nucleic acids from the group consisting of (2) to (4) (nucleic acids for analyzing polymorphisms with three highest odds ratios in Example mentioned below).

A kit for detecting the genotype comprising two or more sets of nucleic acids selected from the group consisting of the following (5) to (8);

(5) a set of nucleic acids which consists of a first nucleic acid that specifically hybridizes a partial region containing the base at position −850 in the sense strand of the tumor necrosis factor α gene whose base at position −850 is C and that is labeled with a first labeling substance, of a second nucleic acid that specifically hybridizes a partial region containing the base at position −850 in the sense strand of the tumor necrosis factor α gene whose base at position −850 is T and that is labeled with a second labeling substance, and of the third nucleic acid that specifically hybridizes a partial region in the antisense strand of the tumor necrosis factor α gene and that can specifically amplify the partial DNA region containing the base at position −850 of the tumor necrosis factor α in concurrent use with the above first or second nucleic acid;

(6) a set of nucleic acids which consists of a first nucleic acid that specifically hybridizes a partial region containing the base at position −238 in the sense strand of the tumor necrosis factor α gene whose base at position −238 is G and that is labeled with a first labeling substance, of a second nucleic acid that specifically hybridizes a partial region containing the base at position −238 in the sense strand of the tumor necrosis factor α gene whose base at position −238 is A and that is labeled with a second labeling substance, and of the third nucleic acid that specifically hybridizes a partial region in the antisense strand of the tumor necrosis factor α gene and that can specifically amplify the partial DNA region containing the base at position −238 of the tumor necrosis factor α in concurrent use with the above first or second nucleic acid;

(7) a set of nucleic acids which consists of a first nucleic acid that specifically hybridizes a partial region containing the base at position 3494 in the antisense strand of the insulin receptor substrate-1 gene whose base at position 3494 is G and that is labeled with a first labeling substance, of a second nucleic acid that specifically hybridizes a partial region containing the base at position 3494 in the antisense strand of the insulin receptor substrate-1 gene whose base at position 3494 is A and that is labeled with a second labeling substance, and of the third nucleic acid that specifically hybridizes a partial region in the sense strand of the insulin receptor substrate-1 gene and that can specifically amplify the partial DNA region containing the base at position 3494 of the insulin receptor substrate-1 gene in concurrent use with the above first or second nucleic acid; and (8) a set of nucleic acids which consists of a first nucleic acid that specifically hybridizes a partial region containing the base at position 1018 in the antisense strand of the glycoprotein Iba gene whose base at position 1018 is C and that is labeled with a first labeling substance, of a second nucleic acid that specifically hybridizes a partial region containing the base at position 1018 in the antisense strand of the glycoprotein Iba gene whose base at position 1018 is T and that is labeled with a second labeling substance, and of the third nucleic acid that specifically hybridizes a partial region in the sense strand of the glycoprotein Iba gene and that can specifically amplify the partial DNA region containing the base at position 1018 of the glycoprotein Iba gene in concurrent use with the above first or second nucleic acid.

In the above mention, kits are constructed by selecting two or more nucleic acids from the group consisting of (5) to (8). However, kits may be constructed by making a group consisting of two or more nucleic acids arbitrarily selected from (5) to (8) and selecting two or more nucleic acids from such a group. For example, kits may be constructed by selecting two or more nucleic acids from the group consisting of (5), (7) to (8) (nucleic acids for analyzing polymorphisms with three highest odds ratios in Example mentioned below).

In the above-mentioned kits, one or two or more of reagents (buffer, reagent for reaction, and reagent for detection, etc.) may be combined in response to the usage of the kit.

The present invention is hereinafter described in more detail by way of Examples.

EXAMPLE 1

Selection of Gene Polymorphism

By using several kinds of public databases including PubMed [National Center for Biological Information (NCBI)], Online Mendelian inheritance in Men (NCBI), Single Nucleotide Polymorphism (NCBI), etc., from a comprehensive viewpoint including vascular biology, platelet-leukocyte biology, coagulation and fibrinolysis system, a metabolic factor such as lipid, sugar, etc., 71 genes which were estimated to be associated with coronary arteriosclerosis, coronary artery spasm, hypertension, diabetes mellitus, hyperlipidemia, etc. were extracted from genes which had been previously reported. Furthermore, among the polymorphisms existing in these genes, 112 polymorphisms including polymorphisms which exist in promoter regions or exons, or polymorphisms which were located in splice donor sites or acceptor sites and expected to be associated with the functional changes of gene products were selected (FIGS. 1 and 2).

EXAMPLE 2

Determination of Gene Polymorphism

The study population comprised 1940 Japanese individuals (1107 men and 833 women) who either visited outpatient clinics of or were admitted to one of the 15 participating hospitals between July 1994 and December 2001. A total of 1067 subjects (574 men and 493 women) either had hypertension [systolic blood pressure of ≧140 mmHg or diastolic blood pressure of ≧90 mmHg, or both] or had taken antihypertensive drugs. Cases with coronary artery disease, valvular heart disease, congenital malformations of the heart or vessels, or renal or endocrinologic diseases that cause secondary hypertension were excluded from the study. The 873 control subjects (533 men and 340 women) with normal blood pressure (systolic blood pressure of <140 mmHg and diastolic blood pressure of <90 mmHg) were recruited from individuals who were found to have at least one of the conventional risk factors for coronary artery disease, including habitual cigarette smoking (≧10 cigarettes daily), obesity [body mass index of >26 kg/m$^2$], diabetes mellitus (fasting blood glucose of >126 mg/dL or hemoglobin $A_{1c}$ of >6.5%, or both), hypercholesterolemia (serum total cholesterol of >220 mg/dL), and hyperuricemia (serum uric acid of >7.7 mg/dL for men or >5.5 mg/dL for women), but who had no history of coronary artery disease. These controls showed normal resting electrocardiogram, and also in exercise tolerance test, no myocardial ischemic change was shown. Blood pressure was measured with subjects in the seated position according to the guidelines of the American Heart Association (Perloff D, Grim C, Flack J, Frohlich E D, Hill M, McDonald M, Morgenstern B Z. Human blood pressure determination by sphygmomanometry. Circulation. 1993; 88: 2640-2470.).

From each of the subjects, 7 mL of venous blood was collected in a tube containing 50 mmol/L EDTA-2Na and genome DNA was extracted by using a DNA extraction kit (Qiagen, Chatsworth, Calif.). Genotypes of single nucleotide polymorphisms were determined with a fluorescence- or colorimetry-based allele-specific primer-probe assay system (Toyobo Gene Analysis, Tsuruga, Japan) (see FIG. 3). DNA fragment containing a polymorphism site was amplified by polymerase chain reaction (PCR) by using two kinds of allele specific sense primers (or antisense primers) whose 5' end were labeled with fluorescein isothiocyanate (FITC) or Texas red (TxR) and an antisense primer (or a sense primer) whose 5' end was labeled with biotin. Alternatively, DNA fragment containing polymorphism site was amplified by PCR by using two kinds of allele specific sense (or antisense) primers and an antisense (or a sense) primer whose 5' end was labeled with biotin, or by using a sense primer and an antisense primer whose 5' end was labeled with biotin. The reaction solution (25 μL) contained 20 ng of DNA, 5 pmol of each primer, 0.2 mmol/L of each deoxynucleoside triphosphate, 1 to 4 mmol/L of $MgCl_2$, 1 U of DNA polymerase (rTaq or KODplus; Toyobo Co., Ltd. Osaka, Japan) in corresponding DNA polymerase buffer. The amplification protocol comprised an initial denaturation at 95° C. for 5 minutes; 35 to 45 cycles of denaturation at 95° C. for 30 seconds, annealing at 55 to 67.5° C. for 30 seconds, extension at 72° C. for 30 seconds, and a final extension at 72° C. for 2 minutes.

For determination of genotype by fluorescence, amplified DNA was incubated with a solution containing streptavidin-conjugated magnetic beads in 96-well plates at room temperature. The plates were placed on a magnetic stand, supernatants were collected from the wells and then transferred to the wells of a 96-well plate containing 0.01 M NaOH, followed by measuring fluorescence by microplate reader at excitation wavelength and fluorescence wavelength of 485 nm and 538 nm for FITC and at excitation wavelength and fluorescence wavelength of 584 nm and 612 nm for TxR. Furthermore, for determination of genotype by colorimetry, amplified DNA was denatured with 0.3 M NaOH and then subjected to hybridization at 37° C. for 30 min in hybridization buffer containing 35 to 40% formamide with any of allele-specific capture probes fixed to the bottom of the wells of a 96-well plate. After thorough washing of the wells, alkaline phosphatase-conjugated streptavidin was added to each well and the plate was shaken at 37° C. for 15 min. The wells were again washed, and, after the addition of a solution containing 0.8 mM 2-(4-iodophenyl)-3-(4-nitrophenyl)-5-(2,4-disulfophenyl)-2H-tetrazolium (monosodium salt) and 0.4 mM 5-bromo-4-chloro-3-indolyl phosphate p-toluidine salt, the absorbance at 450 nm was measured.

To confirm the accuracy of genotyping by this method, DNA samples of 50 people were selected at random, and the samples were subjected to PCR-restriction fragment length polymorphism method or direct sequencing method of PCR products. In any samples, the genotype determined by the allele specific primer-probe measurement system was identical to that determined by PCR-restriction fragment length polymorphism method or direct sequencing method.

Statistical analysis in the following association study was carried out as follows. Quantitative clinical data were compared between patients with hypertension and controls by the unpaired Student's t test or the Mann-Whitney U test. Qualitative data were compared by the chi-square test. Allele frequencies were estimated by the gene counting method, and the chi-square test was used to identify significant departures from Hardy-Weinberg equilibrium. The present inventors performed multivariate logistic regression analysis to adjust risk factors, with hypertension as a dependent variable and independent variables including age, body mass index (BMI), smoking status (0=nonsmoker, and 1=smoker), metabolic variables (0=no history of diabetes mellitus, hypercholesterolemia, or hyperuricemia; and 1=positive history), and genotype of each polymorphism. Each genotype was assessed according to dominant, recessive, and additive genetic models, and the P value, odds ratio, and 95% confidence interval were calculated. For combined genotype analyses, the present inventors performed the stepwise forward selection method of multivariate logistic regression to calculate odds ratios for each combined genotype.

EXAMPLE 3

Selection of Polymorphism Associated with Hypertension and Development of Method for Diagnosing Hypertension The present inventors performed an association study of the 112 polymorphisms of the 71 candidate genes with myocardial infarction in 451 men (myocardial infarction: 219, control: 232) and in 458 women (myocardial infarction: 226, control: 232) in the previous report (Yamada Y, Izawa H, Ichihara S, et al. Prediction of the risk of myocardial infarction from polymorphisms in candate genes. N Engl J Med. in press). In this study, the present inventors have found that 19 and 18 single nucleotide polymorphisms were associated with the development of myocardial infarction in men and women, respectively, which included candidate genes of hypertension (see FIGS. 1, 2 and 4). In this Example, a large scale association study on the association of these single nucleotide polymorphisms with hypertension was carried out in total 1940 cases.

The background data of all 1940 participants (1107 men and 833 women) are shown in FIG. 5. For men, age, BMI, the prevalence of hyperuricemia, and the serum concentration of creatinine as well as systolic and diastolic blood pressure were significantly greater, and the prevalence of smoking was significantly lower, in subjects with hypertension than in controls. For women, age, BMI, and the prevalence of hypercholesterolemia and hyperuricemia as well as systolic and diastolic blood pressure were significantly greater in subjects with hypertension than in controls.

Multivariate logistic regression analysis with adjustment for age, BMI, and the prevalence of smoking, diabetes mellitus, hypercholesterolemia, and hyperuricemia revealed that 4 of the 19 polymorphisms examined for men and 4 of the 18 polymorphisms examined for women were significantly associated with hypertension (P<0.05 in either a dominant or recessive genetic model) (see FIG. 6). The genotype distributions of these polymorphisms are shown (see FIG. 7).

The present inventors performed the stepwise forward selection method of multivariate logistic regression analysis (see FIG. 8) with either a dominant or recessive model for each polymorphism based on the P value (the lower P value) for association with hypertension shown in FIG. 6. The chromosomal loci of the corresponding genes are also shown in FIG. 8.

The −850C→T and −238G→A polymorphisms of the tumor necrosis factor-α gene were not in linkage disequilibrium [pairwise linkage disequilibrium coefficient, D'(D/$D_{max}$), of −0.310 and standardized linkage disequilibrium coefficient, r, of −0.020; P=0.613, chi-square test]. Odds ratios for susceptibility to hypertension based on combined genotypes with the stepwise forward selection method for men and women separately are shown in FIGS. 9 and 11(A) and in FIGS. 10 and 11(B), respectively. For men, combined genotype analysis of the four polymorphisms (GPIa (1648A→G) polymorphism, CCR2 (190G→A) polymorphism, ApoC-III (1100C→T) polymorphism, GPβ3 (825C→T) polymorphism) revealed that the maximal odds ratio was 5.34 (FIGS. 9 and 11(A)). For women, combined genotype analysis of the four polymorphisms (TNFa (−850C→T) polymorphism, TNFa (−238G→A) polymorphism, IRS-1 (3494G→A) polymorphism, GPIba (1018C→T) polymorphism) revealed that the maximal odds ratio was 46.86 (FIGS. 10 and 11(B)).

As mentioned above, multivariate logistic regression analysis revealed that four SNPs related to hypertension in men and women, respectively. That is to say, the relation of hypertension to 19 SNPs for men and 18 SNPs for women was examined in a large-scale association study with 1940 individuals, and four each of the polymorphism related to hypertension development in men and women were identified. Furthermore, the present inventors developed a genetic risk diagnosis system for hypertension based on the combined genotypes for these SNPs that yielded maximal odds ratios of 5.34 for men and 46.86 for women by the stepwise forward selection method of multivariate logistic regression analysis.

The regulation of blood pressure involves both the integration of a variety of biological systems that control the structure and tone of the vasculature and the volume and composition of body fluid, as well as the adaptation of these systems to constantly changing physiological needs (Laouel J-M, Rohrwasser A. Development of genetic hypotheses in essential hypertension. J Hum Genet. 2001; 46: 299-306). The relation of hypertension to 19 SNPs for men and 18 SNPs for women examined for men and women, respectively, in the present study were selected on the basis of a comprehensive overview of vascular biology, platelet-leukocyte biology, the fibrinolysis system, as well as lipid and glucose metabolism and other metabolic factors. Actually, the genes now shown to be associated with hypertension may play roles in diverse aspects of the etiology of this condition, including vascular biology (G protein β3 subunit), inflammation (tumor necrosis factor-α), monocyte and lymphocyte biology (chemokine receptor 2), platelet function (glycoproteins Ia and Ibα), lipid metabolism (apolipoprotein C-III), and insulin and glucose metabolism (insulin receptor substrate-1). The maximal odds ratios obtained with the genetic risk diagnosis system for hypertension developed by the present inventors (5.34 for men and 46.86 for women) appear to be the highest such values reported by large-scale association studies of hypertension particularly in women. Among the eight polymorphisms associated with hypertension, the −850C→T and −238G→A polymorphisms of the tumor necrosis factor-α gene yielded the highest odds ratio for predisposition to hypertension in women. The tumor necrosis factor-α gene locus was previously shown to be associated with obesity-related hypertension in French Canadian (Pausova Z, Deslauriers B, Gaudet D, Tremblay J, Kotchen T A, Larochelle P, Cowley A W, Hamet P. Role of tumor necrosis factor-α gene locus in obesity and obesity-associated hypertension in French Canadians. Hypertension. 2000; 36: 14-19). Furthermore, a −308A→G polymorphism of the tumor necrosis factor-α gene also previously showed a tendency to associate with essential hypertension, although statistical significance was not achieved (Frossard P M, Gupta A, Pravica V, Perry C, Hutchinson I V, Lukic M L. A study of five human cytokine genes in human essential hypertension. Mol Immunol. 2002; 38: 969-976.). The serum concentration of this the tumor necrosis factor-α was associated with systolic blood pressure and insulin resistance in a native Canadian population (Zinman B, Hanley A J G, Harris S B, Kwan J, Fantus I G. Circulating tumor necrosis factor-α concentrations in a native Canadian population with high rates of type 2 diabetes mellitus. J Clin Endocrinol Metab. 1999; 84: 272-278.). Tumor necrosis factors stimulates the production of the potent vasoconstrictor endothelin-1 (Kahaleh M B, Fan P S. Effect of cytokines on the production of endothelin by endothelial cells. Clin Exp Rheumatol. 1997; 15: 163-167.) and the serum concentrations of these two agents were positively correlated in subjects with obesity (Winkler G, Lakatos P, Salamon F, Nagy Z, Speer Q Kovacs M, Harmos G, Dworak O, Cseh K. Elevated serum TNF-a level as a link between endothelial dysfunction and insulin resistance in normotensive obese patients. Diabetes Med. 1999; 16: 207-211.). These findings and the above-mentioned results by the present inventors suggest that the tumor necrosis factor-α gene is a candidate locus for susceptibility to hypertension. With regard to the other six polymorphisms associated with hypertension in the present study, the 825C→T polymorphism of the G protein β3 subunit gene was previously associated with hypertension (Siffert W, Rosskop D, Siffert G, Busch S, Moritz A, Erbel R, Sharma A M, Ritz E, Wichmann H-E, Jakobs K H, Horsthemke B. Association of a human G-protein 13 subunit variant with hypertension. Nat Genet. 1998; 18: 45-48.), and a polymorphism of the apolipoprotein C-III gene was also reported to be associated with blood pressure (Tas S, Abdella N A. Blood pressure, coronary artery disease, and glycaemic control in type 2 diabetes mellitus: relation to apolipoprotein-CIII gene polymorphism. Lancet. 1994; 343: 1994-1995.). Chemokine receptor 2 and insulin receptor substrate-1 genes have been shown to contribute to the development of hypertension (Bush E, Maeda N, Kuziel W A, Dawson T C, Wilcox J N, DeLeon H, Taylor W R. CC chemokine receptor 2 is required for macrophage infiltration and vascular hypertrophy in angiotensin II-induced hypertension. Hypertension. 2000; 36: 360-363., Abe H, Yamada N, Kamata K, Kuwaki T, Shimada M, Osuga J, Shionoiri F, Yahagi N, Kadowaki T, Tamemoto H, Ishibashi S, Yazaki Y, Makuuchi M. Hypertension, hypertriglyceridemia, and impaired endothelium-dependent vascular relaxation in mice lacking insulin receptor substrate-1. J Clin Invest. 1998; 101: 1784-1788.). Furthermore, platelet activation may be important in the etiology of essential hypertension (Andrioli G, Ortolani R, Fontana L, Gaino S, Bellavite P, Lechi C, Minuz P, Manzato F, Tridente G, Lechi A. Study of platelet adhesion in patients with uncomplicated hypertension. J Hypertens. 1996; 14: 1215-1221., Dockrell M E, Walker B R, Noon J P, Watt G C, Williams B C, Webb D J. Platelet aggregation in young men contrasting predisposition to high blood pressure. Am J Hypertens. 1999; 12: 115-119., Bereczki C, Tur S, Nemeth I, Sallai E, Torday C, Nagy E, Haszon I, Papp F. The roles of platelet function, thromboxane, blood lipids, and nitric oxide in hypertension of children and adolescents. Prostaglandins Leukot Essent Fatty Acids. 2000; 62: 293-297.); although the polymorphisms in the glycoprotein Ia and glycoprotein Iba genes studied here have been associated with coronary artery disease (Kroll H, Gardemann A, Fechter A, Haberbosch W, Santoso S. The impact of the glycoprotein Ia collagen receptor subunit A1648G gene polymorphism on coronary artery disease and acute myocardial infarction. Thromb Haemost. 2000; 83: 392-396., Murata M, Matsubara Y, Kawano K, et al. Coronary artery disease and polymorphisms in a receptor mediating shear stress-dependent platelet activation. Circulation. 1997; 96: 3281-6.), they have not previously been associated with hypertension.

It is possible that some of the polymorphisms examined in the present Examples are in linkage disequilibrium with polymorphisms of other nearby genes that are actually responsible for the development of hypertension. The present results indicate, however, that glycoprotein Ia, chemokine receptor 2, apolipoprotein C-III, and the G protein β3 subunit are susceptibility loci for hypertension in Japanese men, and that tumor necrosis factor-α, insulin receptor substrate-1, and glycoprotein Iba constitute such loci in Japanese women. Moreover, the combined genotypes for these polymorphisms may prove informative for determination of the genetic risk for hypertension. The genetic diagnosis system by the present inventors should therefore contribute to the primary prevention of hypertension and of cardiovascular diseases, stroke, or renal diseases induced by this condition.

The present invention is not limited to the description of the above embodiments. A variety of modifications, which are within the scopes of the following claims and which are achieved easily by a person skilled in the art, are included in the present invention.

INDUSTRIAL APPLICABILITY

According to the present invention, gene polymorphisms associated with hypertension are analyzed and the genotype in a nucleic acid sample is detected. By using the information about the polymorphisms obtained by the detection of the genotype, diagnosis of the risk for hypertension with high accuracy and high predictability can be carried out. Therefore, the present invention provides an effective means for understanding in advance the risk of development of hypertension, so that it can be expected that the means should therefore contribute to the primary prevention of hypertension as well as to contribute the prevention of cardiovascular diseases, stroke, renal diseases, or the like, induced by hypertension. Furthermore, according to the present invention, auxiliary information useful for the diagnosis of hypertension can be obtained so as to enable an appropriate treatment and therefore prognosis can be improved. Furthermore, since the present invention provides useful information in elucidating the development mechanism of hypertension, it also provides an extremely important means for establishing a preventing method for hypertension.

The invention claimed is:
1. A method for assessing the genetic risk for hypertension in a human male subject, the method comprising the following steps (i) to (iii):
   (i) analyzing the following polymorphisms (1) to (3) in a nucleic acid sample from the human male subject:
   (1) a polymorphism at the base number position 1648 of the glycoprotein Ia (GpIa) gene, wherein the polymorphism is A1648G;
   (2) a polymorphism at the base number position 190 of the chemokine receptor 2 (CCR2) gene, wherein the polymorphism is G190A; and
   (3) a polymorphism at the base number position 1100 of the apolipoprotein C-III (apo CIII) gene, wherein the polymorphism is C1100T;
   (ii) determining, based on the information about polymorphisms which was obtained in the step (i), the genotype of the nucleic acid sample from the human male subject; and
   (iii) assessing, based on the genotype determined, a genetic risk for hypertension in the human male subject, wherein a genotype including A at position 1648 of the GpIa gene, A at position 190 of the CCR2 gene, and C at position 1100 of the apo CIII gene indicates a genetic risk for hypertension in the human male subject.

* * * * *